(12) United States Patent
Longo et al.

(10) Patent No.: US 11,660,218 B2
(45) Date of Patent: May 30, 2023

(54) DELIVERY DEVICE AND METHOD OF DELIVERY

(71) Applicant: Intact Vascular, Inc., Wayne, PA (US)

(72) Inventors: Michael Longo, Glenmoore, PA (US); Michael Horzewski, San Jose, CA (US)

(73) Assignee: INTACT VASCULAR, INC., Wayne, PA (US)

( * ) Notice: Subject to any disclaimer, the term of this patent is extended or adjusted under 35 U.S.C. 154(b) by 185 days.

(21) Appl. No.: 16/632,841

(22) PCT Filed: Jul. 24, 2018

(86) PCT No.: PCT/US2018/043528
§ 371 (c)(1),
(2) Date: Jan. 21, 2020

(87) PCT Pub. No.: WO2019/023258
PCT Pub. Date: Jan. 31, 2019

(65) Prior Publication Data
US 2020/0155332 A1 May 21, 2020

Related U.S. Application Data

(63) Continuation-in-part of application No. 15/705,793, filed on Sep. 15, 2017, now abandoned.
(Continued)

(51) Int. Cl.
A61F 2/958 (2013.01)
A61F 2/962 (2013.01)
(Continued)

(52) U.S. Cl.
CPC .............. A61F 2/958 (2013.01); A61F 2/915 (2013.01); A61F 2/962 (2013.01); A61M 25/01 (2013.01);
(Continued)

(58) Field of Classification Search
CPC .............. A61F 2/958; A61F 2250/0098; A61F 2002/826; A61F 2/962; A61F 2/915;
(Continued)

(56) References Cited

U.S. PATENT DOCUMENTS 3,051,172 A 8/1962 Bruchhaus
3,221,746 A 12/1965 Noble
(Continued)

FOREIGN PATENT DOCUMENTS

AU 2008335140 11/2012
AU 2011274392 11/2013
(Continued)

OTHER PUBLICATIONS

Bosiers, M. et al., "Results from the Tack Optimized Balloon Angioplasty (TOBA) study demonstrate the benefits of minimal metal implants for dissection repair after angioplasty", Journal of Vascular Surgery, vol. 64, Jul. 2016, in 8 pages.
(Continued)

Primary Examiner — Kathleen S Holwerda
Assistant Examiner — Serenity A Miller

(57) ABSTRACT

A delivery device can provide sequential delivery of a plurality of intraluminal devices held in a compressed state on the delivery device. Delivery platforms on the delivery device can hold an intraluminal device in a compressed position and be positioned between pusher bands that may also be radiopaque markers. A post deployment dilation device can be included. The post deployment dilation device can be a plurality of expansion filaments, a bellows, or a balloon. An intravascular device deployment method can include allowing a self-expanding intravascular device to expand, aligning the post deployment dilation device under
(Continued)

the intravascular device, and causing the post deployment dilation device to expand radially to push outward on the intravascular device.

14 Claims, 28 Drawing Sheets

Related U.S. Application Data

(60) Provisional application No. 62/536,987, filed on Jul. 26, 2017.

(51) Int. Cl.
  *A61F 2/915* (2013.01)
  *A61M 25/01* (2006.01)

(52) U.S. Cl.
  CPC .......... *A61F 2002/91575* (2013.01); *A61F 2250/0098* (2013.01); *A61M 2025/0183* (2013.01)

(58) Field of Classification Search
  CPC ........ A61F 2002/91575; A61F 2/2433; A61M 25/01; A61M 2025/1059; A61M 2025/1081; A61M 2025/1084; A61M 25/1006; A61M 2025/0183
  USPC .................................................. 623/1.12, 1.11
  See application file for complete search history.

(56) References Cited

U.S. PATENT DOCUMENTS

| | | | |
|---|---|---|---|
| 3,635,223 A | 1/1972 | Klieman | |
| 4,024,873 A | 5/1977 | Antoshkiw et al. | |
| 4,292,974 A | 10/1981 | Fogarty et al. | |
| 4,446,867 A | 5/1984 | Leveen et al. | |
| 4,465,072 A | 8/1984 | Taheri | |
| 4,515,587 A | 5/1985 | Schiff | |
| 4,545,367 A | 10/1985 | Tucci | |
| 4,545,390 A | 10/1985 | Leary | |
| 4,552,127 A | 11/1985 | Schiff | |
| 4,576,591 A | 3/1986 | Kay et al. | |
| 4,589,412 A | 5/1986 | Kensey | |
| 4,641,654 A | 2/1987 | Samson et al. | |
| 4,651,738 A | 3/1987 | Demer et al. | |
| 4,687,465 A | 8/1987 | Prindle et al. | |
| 4,723,550 A | 2/1988 | Bales et al. | |
| 4,723,936 A | 2/1988 | Buchbinder et al. | |
| 4,723,938 A | 2/1988 | Goodin et al. | |
| 4,726,374 A | 2/1988 | Bales et al. | |
| 4,758,223 A | 7/1988 | Rydell | |
| 4,762,130 A | 8/1988 | Fogarty et al. | |
| 4,781,192 A | 11/1988 | Demer | |
| 4,784,636 A | 11/1988 | Rydell | |
| 4,846,174 A | 7/1989 | Willard et al. | |
| 4,848,342 A | 7/1989 | Kaltenbach | |
| RE33,166 E | 2/1990 | Samson | |
| 4,921,484 A | 5/1990 | Hillstead | |
| 4,994,065 A | 2/1991 | Gibbs et al. | |
| 5,009,659 A | 4/1991 | Hamlin et al. | |
| 5,024,668 A | 6/1991 | Peters et al. | |
| 5,042,707 A | 8/1991 | Taheri | |
| 5,047,015 A | 9/1991 | Foote et al. | |
| 5,102,390 A | 4/1992 | Crittenden et al. | |
| 5,160,341 A | 11/1992 | Brenneman et al. | |
| 5,190,058 A | 3/1993 | Jones et al. | |
| 5,196,024 A | 3/1993 | Barath | |
| 5,201,757 A | 4/1993 | Heyn et al. | |
| 5,242,452 A | 9/1993 | Inoue | |
| 5,246,420 A | 9/1993 | Kraus et al. | |
| 5,250,029 A | 10/1993 | Lin et al. | |
| 5,250,060 A | 10/1993 | Carbo et al. | |
| 5,261,878 A | 11/1993 | Galindo | |
| 5,263,962 A | 11/1993 | Johnson et al. | |
| 5,269,758 A | 12/1993 | Taheri | |
| 5,304,121 A | 4/1994 | Sahatjian | |
| 5,318,529 A | 6/1994 | Kontos | |
| 5,336,234 A | 8/1994 | Virgil et al. | |
| 5,344,397 A | 9/1994 | Heaven et al. | |
| 5,383,890 A | 1/1995 | Miraki et al. | |
| 5,397,305 A | 3/1995 | Kawula et al. | |
| 5,397,355 A | 3/1995 | Marin et al. | |
| 5,421,955 A | 6/1995 | Lau et al. | |
| 5,423,851 A | 6/1995 | Samuels | |
| 5,423,885 A | 6/1995 | Williams | |
| 5,443,477 A | 8/1995 | Marin et al. | |
| 5,484,449 A * | 1/1996 | Amundson | A61F 2/958 606/198 |
| 5,489,295 A | 2/1996 | Piplani et al. | |
| 5,501,689 A | 3/1996 | Green et al. | |
| 5,534,007 A | 7/1996 | St. Germain et al. | |
| 5,536,252 A | 7/1996 | Imran et al. | |
| 5,540,659 A | 7/1996 | Teirstein | |
| 5,545,135 A | 8/1996 | Iacob et al. | |
| 5,562,728 A | 10/1996 | Lazarus et al. | |
| 5,569,272 A | 10/1996 | Reed et al. | |
| 5,571,135 A | 11/1996 | Fraser et al. | |
| 5,591,197 A | 1/1997 | Orth et al. | |
| 5,593,417 A | 1/1997 | Rhodes | |
| 5,601,568 A | 2/1997 | Chevillon et al. | |
| 5,616,149 A | 4/1997 | Barath | |
| 5,618,300 A | 4/1997 | Marin et al. | |
| 5,632,771 A | 5/1997 | Boatman et al. | |
| 5,634,928 A | 6/1997 | Fischell et al. | |
| 5,643,312 A | 7/1997 | Fischell et al. | |
| 5,645,559 A | 7/1997 | Hachtman et al. | |
| 5,665,116 A | 9/1997 | Chaisson et al. | |
| 5,681,346 A | 10/1997 | Orth et al. | |
| 5,704,913 A | 1/1998 | Abele et al. | |
| 5,707,376 A | 1/1998 | Kavteladze et al. | |
| 5,725,572 A | 3/1998 | Lam et al. | |
| 5,728,158 A | 3/1998 | Lau et al. | |
| 5,741,270 A | 4/1998 | Hansen et al. | |
| 5,743,874 A | 4/1998 | Fischell et al. | |
| 5,746,716 A | 5/1998 | Vigil et al. | |
| 5,746,764 A | 5/1998 | Green et al. | |
| 5,776,161 A | 7/1998 | Globerman | |
| 5,797,951 A | 8/1998 | Mueller | |
| 5,800,526 A | 9/1998 | Anderson et al. | |
| 5,807,398 A | 9/1998 | Shaknovich | |
| 5,813,977 A | 9/1998 | Hinchliffe et al. | |
| 5,817,152 A | 10/1998 | Birdsall et al. | |
| 5,829,662 A | 11/1998 | Allen et al. | |
| 5,833,694 A | 11/1998 | Poncet | |
| 5,843,033 A | 12/1998 | Ropiak | |
| 5,843,090 A | 12/1998 | Schuetz | |
| 5,911,725 A | 6/1999 | Boury | |
| 5,925,038 A | 7/1999 | Panescu et al. | |
| 5,925,061 A | 7/1999 | Ogi et al. | |
| 5,928,247 A | 7/1999 | Barry et al. | |
| 5,944,727 A | 8/1999 | Ahari et al. | |
| 5,954,742 A | 9/1999 | Osypka | |
| 5,957,949 A | 9/1999 | Leonhardt et al. | |
| 5,968,052 A | 10/1999 | Sullivan, III et al. | |
| 5,968,068 A | 10/1999 | Dehdashtian et al. | |
| 5,968,088 A | 10/1999 | Hansen et al. | |
| 5,972,023 A | 10/1999 | Tanner et al. | |
| 5,980,552 A | 11/1999 | Pinchasik et al. | |
| 6,004,328 A | 12/1999 | Solar | |
| 6,007,543 A | 12/1999 | Ellis et al. | |
| 6,009,614 A | 1/2000 | Morales | |
| 6,013,854 A | 1/2000 | Moriuchi | |
| 6,022,374 A | 2/2000 | Imran | |
| 6,036,725 A | 3/2000 | Avellanet | |
| 6,048,360 A | 4/2000 | Khosravi et al. | |
| 6,053,941 A | 4/2000 | Lindenberg et al. | |
| 6,053,943 A | 4/2000 | Edwin et al. | |
| 6,080,177 A | 6/2000 | Igaki | |
| 6,090,135 A | 7/2000 | Plaia et al. | |
| 6,102,904 A | 8/2000 | Vigil et al. | |
| 6,110,198 A | 8/2000 | Fogarty et al. | |
| 6,123,722 A | 9/2000 | Fogarty et al. | |
| 6,126,685 A | 10/2000 | Lenker et al. | |

(56) References Cited

U.S. PATENT DOCUMENTS

| | | |
|---|---|---|
| 6,129,754 A | 10/2000 | Kanesaka et al. |
| 6,139,573 A | 10/2000 | Sogard et al. |
| 6,143,016 A | 11/2000 | Bleam et al. |
| 6,146,358 A | 11/2000 | Rowe |
| 6,152,937 A | 11/2000 | Peterson et al. |
| 6,157,852 A | 12/2000 | Selmon et al. |
| 6,165,199 A | 12/2000 | Barbut |
| 6,187,034 B1 | 2/2001 | Frantzen |
| 6,197,013 B1 | 3/2001 | Reed |
| 6,197,103 B1 | 3/2001 | Davies et al. |
| 6,200,336 B1 | 3/2001 | Pavcnik et al. |
| 6,203,550 B1 | 3/2001 | Olson |
| 6,203,568 B1 | 3/2001 | Lombardi et al. |
| 6,203,569 B1 | 3/2001 | Wijay |
| 6,221,102 B1 | 4/2001 | Baker et al. |
| 6,238,402 B1 | 5/2001 | Sullivan et al. |
| 6,241,667 B1 | 6/2001 | Vetter et al. |
| 6,254,628 B1 | 7/2001 | Wallace et al. |
| 6,258,117 B1 | 7/2001 | Camrud et al. |
| 6,266,550 B1 | 7/2001 | Selmon et al. |
| 6,270,524 B1 | 8/2001 | Kim |
| 6,273,909 B1 | 8/2001 | Kugler et al. |
| 6,290,728 B1 | 9/2001 | Phelps et al. |
| 6,312,444 B1 | 11/2001 | Barbut |
| 6,312,460 B2 | 11/2001 | Drasler et al. |
| 6,325,824 B2 | 12/2001 | Limon |
| 6,331,189 B1 | 12/2001 | Wolinsky et al. |
| 6,338,739 B1 | 1/2002 | Datta et al. |
| 6,344,053 B1 | 2/2002 | Boneau |
| 6,364,901 B1 | 4/2002 | Inoue |
| 6,364,904 B1 | 4/2002 | Smith |
| 6,371,962 B1 | 4/2002 | Ellis et al. |
| 6,387,113 B1 | 5/2002 | Hawkins et al. |
| 6,391,050 B1 | 5/2002 | Broome |
| 6,402,760 B1 | 6/2002 | Fedida |
| 6,402,777 B1 | 6/2002 | Globerman |
| 6,409,752 B1 | 6/2002 | Boatman et al. |
| 6,409,863 B1 | 6/2002 | Williams et al. |
| 6,425,915 B1 | 7/2002 | Khosravi et al. |
| 6,428,550 B1 | 8/2002 | Vargas et al. |
| 6,428,566 B1 | 8/2002 | Holt |
| 6,451,047 B2 | 9/2002 | Edwin et al. |
| 6,458,151 B1 | 10/2002 | Saltiel |
| 6,475,237 B2 | 11/2002 | Drasler et al. |
| 6,485,507 B1 | 11/2002 | Walak et al. |
| 6,485,508 B1 | 11/2002 | McGuinness |
| 6,485,510 B1 | 11/2002 | Camrud et al. |
| 6,491,707 B2 | 12/2002 | Makower et al. |
| 6,508,822 B1 | 1/2003 | Peterson et al. |
| 6,514,228 B1 | 2/2003 | Hamilton et al. |
| 6,514,261 B1 | 2/2003 | Randall et al. |
| 6,517,573 B1 | 2/2003 | Pollock et al. |
| 6,520,934 B1 | 2/2003 | Lee et al. |
| 6,520,983 B1 | 2/2003 | Colgan et al. |
| 6,520,984 B1 | 2/2003 | Garrison et al. |
| 6,527,800 B1 | 3/2003 | McGuckin, Jr. et al. |
| 6,547,817 B1 | 4/2003 | Fischell et al. |
| 6,551,353 B1 | 4/2003 | Baker et al. |
| 6,599,296 B1 | 7/2003 | Gillick et al. |
| 6,602,226 B1 | 8/2003 | Smith et al. |
| 6,607,551 B1 | 8/2003 | Sullivan et al. |
| 6,623,521 B2 | 9/2003 | Steinke et al. |
| 6,629,994 B2 | 10/2003 | Gomez et al. |
| 6,635,083 B1 | 10/2003 | Cheng et al. |
| 6,648,911 B1 | 11/2003 | Sirhan et al. |
| 6,660,031 B2 | 12/2003 | Tran et al. |
| 6,676,698 B2 | 1/2004 | McGuckin, Jr. et al. |
| 6,692,504 B2 | 2/2004 | Kurz et al. |
| 6,699,274 B2 | 3/2004 | Stinson |
| 6,699,277 B1 | 3/2004 | Freidberg et al. |
| 6,702,843 B1 | 3/2004 | Brown et al. |
| 6,706,061 B1 | 3/2004 | Fischell et al. |
| 6,716,240 B2 | 4/2004 | Fischell et al. |
| 6,719,775 B2 | 4/2004 | Slaker et al. |
| 6,723,119 B2 | 4/2004 | Pinchasik et al. |
| 6,730,116 B1 | 5/2004 | Wolinsky et al. |
| 6,746,475 B1 | 6/2004 | Rivelli, Jr. |
| 6,752,828 B2 | 6/2004 | Thornton |
| 6,755,854 B2 | 6/2004 | Gillick et al. |
| 6,786,922 B2 | 9/2004 | Schaeffer |
| 6,790,221 B2 | 9/2004 | Monroe et al. |
| 6,790,227 B2 | 9/2004 | Burgermeister |
| 6,810,882 B2 | 11/2004 | Langberg et al. |
| 6,814,752 B1 | 11/2004 | Chuter |
| 6,827,731 B2 | 12/2004 | Armstrong et al. |
| 6,843,400 B1 | 1/2005 | Lee |
| 6,846,323 B2 | 1/2005 | Yip et al. |
| 6,849,087 B1 | 2/2005 | Chuter |
| 6,863,685 B2 | 3/2005 | Davila et al. |
| 6,866,669 B2 | 3/2005 | Buzzard et al. |
| 6,896,697 B1 | 5/2005 | Yip et al. |
| 6,899,718 B2 | 5/2005 | Gifford, III et al. |
| 6,899,914 B2 | 5/2005 | Schaldach et al. |
| 6,911,039 B2 | 6/2005 | Shiu et al. |
| 6,913,600 B2 | 7/2005 | Valley et al. |
| 6,942,680 B2 | 9/2005 | Grayzel et al. |
| 6,942,689 B2 | 9/2005 | Majercak |
| 6,945,992 B2 | 9/2005 | Goodson, IV et al. |
| 6,951,554 B2 | 10/2005 | Johansen et al. |
| 6,986,784 B1 | 1/2006 | Weiser et al. |
| 6,989,021 B2 | 1/2006 | Bosma et al. |
| 7,001,422 B2 | 2/2006 | Escamilla et al. |
| 7,001,424 B2 | 2/2006 | Patel et al. |
| 7,007,698 B2 | 3/2006 | Thornton |
| 7,018,402 B2 | 3/2006 | Vito et al. |
| 7,025,791 B2 | 4/2006 | Levine et al. |
| 7,037,330 B1 | 5/2006 | Rivelli, Jr. et al. |
| 7,041,130 B2 | 5/2006 | Santini, Jr. et al. |
| 7,052,511 B2 | 5/2006 | Weldon |
| 7,087,088 B2 | 8/2006 | Berg et al. |
| 7,105,016 B2 | 9/2006 | Shiu et al. |
| 7,122,043 B2 | 10/2006 | Greenhalgh et al. |
| 7,137,993 B2 | 11/2006 | Acosta et al. |
| 7,147,655 B2 | 12/2006 | Chermoni |
| 7,147,656 B2 | 12/2006 | Andreas et al. |
| 7,147,661 B2 | 12/2006 | Chobotov et al. |
| 7,150,745 B2 | 12/2006 | Stern et al. |
| 7,160,312 B2 | 1/2007 | Saadat |
| 7,163,552 B2 | 1/2007 | Diaz |
| 7,166,125 B1 | 1/2007 | Baker et al. |
| 7,169,158 B2 | 1/2007 | Sniffin et al. |
| 7,169,163 B2 | 1/2007 | Becker |
| 7,172,617 B2 | 2/2007 | Colgan et al. |
| 7,175,654 B2 | 2/2007 | Bonsignore et al. |
| 7,179,284 B2 | 2/2007 | Khosravi et al. |
| 7,182,779 B2 | 2/2007 | Acosta et al. |
| 7,186,237 B2 | 3/2007 | Meyer et al. |
| 7,192,440 B2 | 3/2007 | Andreas et al. |
| 7,201,770 B2 | 4/2007 | Johnson et al. |
| 7,208,002 B2 | 4/2007 | Shelso |
| 7,211,101 B2 | 5/2007 | Carley et al. |
| 7,243,408 B2 | 7/2007 | Vietmeier |
| 7,258,697 B1 | 8/2007 | Cox et al. |
| 7,261,731 B2 | 8/2007 | Patel et al. |
| 7,267,684 B2 | 9/2007 | Rolando et al. |
| 7,270,668 B2 | 9/2007 | Andreas et al. |
| 7,270,673 B2 | 9/2007 | Yee et al. |
| 7,273,492 B2 | 9/2007 | Cheng et al. |
| 7,279,007 B2 | 10/2007 | Nikolic et al. |
| 7,294,146 B2 | 11/2007 | Chew et al. |
| 7,296,577 B2 | 11/2007 | Lashinski et al. |
| 7,300,456 B2 | 11/2007 | Andreas et al. |
| 7,303,572 B2 | 12/2007 | Meisheimer et al. |
| 7,303,580 B2 | 12/2007 | Parker |
| 7,306,617 B2 | 12/2007 | Majercak |
| 7,309,341 B2 | 12/2007 | Ortiz et al. |
| 7,309,350 B2 | 12/2007 | Landreville et al. |
| 7,309,353 B2 | 12/2007 | Krivoruchko |
| 7,316,711 B2 | 1/2008 | Allen et al. |
| 7,320,702 B2 | 1/2008 | Hammersmark et al. |
| 7,323,006 B2 | 1/2008 | Andreas et al. |
| 7,323,007 B2 | 1/2008 | Sano |
| 7,326,203 B2 | 2/2008 | Papineau et al. |
| 7,326,236 B2 | 2/2008 | Andreas et al. |

(56) References Cited

U.S. PATENT DOCUMENTS

| | | |
|---|---|---|
| 7,329,279 B2 | 2/2008 | Haug et al. |
| 7,331,987 B1 | 2/2008 | Cox |
| 7,331,990 B2 | 2/2008 | Gianotti |
| 7,331,992 B2 | 2/2008 | Randall et al. |
| 7,351,255 B2 | 4/2008 | Andreas |
| 7,399,307 B2 | 7/2008 | Evans et al. |
| 7,402,168 B2 | 7/2008 | Sanderson et al. |
| 7,419,501 B2 | 9/2008 | Chiu et al. |
| 7,431,729 B2 | 10/2008 | Chanduszko |
| 7,445,631 B2 | 11/2008 | Salaheih et al. |
| 7,476,245 B2 | 1/2009 | Abbate |
| 7,479,158 B2 | 1/2009 | Gregorich |
| 7,500,986 B2 | 3/2009 | Lye et al. |
| 7,510,575 B2 | 3/2009 | Spenser et al. |
| 7,524,330 B2 | 4/2009 | Berreklouw |
| 7,537,607 B2 | 5/2009 | Gerberding |
| 7,550,001 B2 | 6/2009 | Dorn et al. |
| 7,553,324 B2 | 6/2009 | Andreas et al. |
| 7,556,647 B2 | 7/2009 | Drews et al. |
| 7,578,840 B2 | 8/2009 | Schaeffer |
| 7,591,848 B2 | 9/2009 | Allen |
| 7,604,662 B2 | 10/2009 | Cambronne et al. |
| 7,611,497 B2 | 11/2009 | Wollschlager |
| 7,617,007 B2 | 11/2009 | Williams et al. |
| 7,618,432 B2 | 11/2009 | Pedersen et al. |
| 7,618,447 B2 | 11/2009 | Case et al. |
| 7,625,398 B2 | 12/2009 | Clifford et al. |
| 7,625,399 B2 | 12/2009 | Case et al. |
| 7,628,803 B2 | 12/2009 | Pavcnik et al. |
| 7,637,935 B2 | 12/2009 | Pappas et al. |
| 7,655,033 B2 | 2/2010 | Fearnot et al. |
| 7,655,034 B2 | 2/2010 | Mitchell et al. |
| 7,658,759 B2 | 2/2010 | Case et al. |
| 7,666,216 B2 | 2/2010 | Hogendijk et al. |
| 7,674,282 B2 | 3/2010 | Wu et al. |
| 7,686,824 B2 | 3/2010 | Konstantino et al. |
| 7,686,843 B2 | 3/2010 | Moore |
| 7,695,507 B2 | 4/2010 | Rivelli, Jr. et al. |
| 7,720,521 B2 | 5/2010 | Chang et al. |
| 7,736,387 B2 | 6/2010 | Pollock et al. |
| 7,758,594 B2 | 7/2010 | Lamson et al. |
| 7,758,625 B2 | 7/2010 | Wu et al. |
| 7,758,627 B2 | 7/2010 | Richter |
| 7,758,632 B2 | 7/2010 | Hojeibane et al. |
| 7,763,063 B2 | 7/2010 | Arbefeuille et al. |
| 7,780,716 B2 | 8/2010 | Pappas et al. |
| 7,794,489 B2 | 9/2010 | Shumer et al. |
| 7,799,065 B2 | 9/2010 | Pappas |
| 7,806,918 B2 | 10/2010 | Nissl et al. |
| 7,810,223 B2 | 10/2010 | Hemerick et al. |
| 7,828,834 B2 | 11/2010 | Garbe |
| 7,833,262 B2 | 11/2010 | McGuckin, Jr. et al. |
| 7,842,080 B2 | 11/2010 | Chouinard |
| 7,846,194 B2 | 12/2010 | Hartley et al. |
| 7,867,267 B2 | 1/2011 | Sullivan et al. |
| 7,871,431 B2 | 1/2011 | Gurm et al. |
| 7,883,537 B2 | 2/2011 | Grayzel et al. |
| 7,896,911 B2 | 3/2011 | Schneider et al. |
| 7,905,913 B2 | 3/2011 | Chew et al. |
| 7,918,880 B2 | 4/2011 | Austin |
| 7,922,755 B2 | 4/2011 | Acosta et al. |
| 7,933,660 B2 | 4/2011 | Carr |
| 7,938,851 B2 | 5/2011 | Olson et al. |
| 7,942,920 B2 | 5/2011 | Majercak |
| 7,955,315 B2 | 6/2011 | Feinberg et al. |
| 7,963,987 B2 | 6/2011 | Meisheimer et al. |
| 7,967,855 B2 | 6/2011 | Furst et al. |
| 7,971,333 B2 | 7/2011 | Gale et al. |
| 7,972,373 B2 | 7/2011 | Contiliano et al. |
| 7,981,149 B2 | 7/2011 | Contiliano et al. |
| 7,993,383 B2 | 8/2011 | Hartley et al. |
| 8,002,725 B2 | 8/2011 | Hogendijk |
| 8,016,870 B2 | 9/2011 | Chew et al. |
| 8,016,872 B2 | 9/2011 | Parker |
| 8,024,851 B2 | 9/2011 | Barr et al. |
| 8,034,099 B2 | 10/2011 | Pellegrini |
| 8,043,354 B2 | 10/2011 | Greenberg et al. |
| 8,043,357 B2 | 10/2011 | Hartley |
| 8,048,151 B2 | 11/2011 | O'Brien et al. |
| 8,052,738 B2 | 11/2011 | Craven |
| 8,057,543 B2 | 11/2011 | O'Brien et al. |
| 8,062,344 B2 | 11/2011 | Dorn et al. |
| 8,075,607 B2 | 12/2011 | Meisheimer et al. |
| 8,092,468 B2 | 1/2012 | Hansen |
| 8,100,958 B2 | 1/2012 | Fischer et al. |
| 8,127,422 B2 | 3/2012 | Wu |
| 8,128,677 B2 | 3/2012 | Schneider et al. |
| 8,157,851 B2 | 4/2012 | Andreas |
| 8,157,857 B2 | 4/2012 | Case et al. |
| 8,177,831 B2 | 5/2012 | Andreas |
| 8,221,489 B2 | 7/2012 | Issenmann et al. |
| 8,236,044 B2 | 8/2012 | Robaina |
| 8,236,045 B2 | 8/2012 | Benichou et al. |
| 8,292,938 B2 | 10/2012 | Case |
| 8,308,790 B2 | 11/2012 | Arbefeuille et al. |
| 8,317,859 B2 | 11/2012 | Snow et al. |
| 8,323,243 B2 | 12/2012 | Schneider et al. |
| 8,328,864 B2 | 12/2012 | Niermann |
| 8,353,945 B2 | 1/2013 | Andreas et al. |
| 8,366,766 B2 | 2/2013 | Berreklouw |
| 8,382,813 B2 | 2/2013 | Shumer |
| 8,394,139 B2 | 3/2013 | Roeder et al. |
| 8,403,978 B2 | 3/2013 | Schlun et al. |
| 8,409,267 B2 | 4/2013 | Berez et al. |
| 8,414,636 B2 | 4/2013 | Nabulsi et al. |
| 8,414,637 B2 | 4/2013 | Chouinard |
| 8,460,357 B2 | 6/2013 | McGarry et al. |
| 8,460,368 B2 | 6/2013 | Taylor et al. |
| 8,474,460 B2 | 7/2013 | Barrett et al. |
| 8,486,128 B2 | 7/2013 | Jen et al. |
| 8,486,132 B2 | 7/2013 | Snow et al. |
| 8,496,698 B2 | 7/2013 | Abunassar |
| 8,500,787 B2 | 8/2013 | Simpson et al. |
| 8,500,789 B2 | 8/2013 | Wuebbeling et al. |
| 8,523,935 B2 | 9/2013 | Fliedner |
| 8,540,760 B2 | 9/2013 | Paul, Jr. et al. |
| 8,585,747 B2 | 11/2013 | Andreas et al. |
| 8,636,793 B2 | 1/2014 | Hoerstrup et al. |
| 8,641,755 B2 | 2/2014 | Davis et al. |
| 8,652,198 B2 | 2/2014 | Andreas et al. |
| 8,663,310 B2 | 3/2014 | Greenberg et al. |
| 8,667,838 B2 | 3/2014 | Hoem et al. |
| 8,734,502 B2 | 5/2014 | Orr |
| 8,740,973 B2 | 6/2014 | Furst et al. |
| 8,745,842 B2 | 6/2014 | Wu |
| 8,771,335 B2 | 7/2014 | Griego et al. |
| 8,778,010 B2 | 7/2014 | Venturelli et al. |
| 8,784,467 B2 | 7/2014 | Connelly et al. |
| 8,784,468 B2 | 7/2014 | Gerdts et al. |
| 8,821,563 B2 | 9/2014 | Orr et al. |
| 8,834,556 B2 | 9/2014 | Papp et al. |
| 8,864,811 B2 | 10/2014 | Kao |
| 8,888,834 B2 | 11/2014 | Hansen et al. |
| 8,888,841 B2 | 11/2014 | Pandelidis et al. |
| 8,900,289 B2 | 12/2014 | Thompson |
| 8,911,487 B2 | 12/2014 | Bennett et al. |
| 8,926,689 B2 | 1/2015 | Bogert |
| 8,956,398 B2 | 2/2015 | George et al. |
| 8,961,583 B2 | 2/2015 | Hojeibane et al. |
| 8,966,736 B2 | 3/2015 | Wu |
| 8,968,383 B1 | 3/2015 | Johnson et al. |
| 8,986,362 B2 | 3/2015 | Snow et al. |
| 9,005,265 B2 | 4/2015 | Lootz et al. |
| 9,005,274 B2 | 4/2015 | Seguin et al. |
| 9,023,095 B2 | 5/2015 | Bueche et al. |
| 9,050,181 B2 | 6/2015 | Hartley |
| 9,056,351 B2 | 6/2015 | Krivoruchko et al. |
| 9,095,461 B2 | 8/2015 | Schaeffer |
| 9,101,500 B2 | 8/2015 | Feld et al. |
| 9,101,503 B2 | 8/2015 | Lowe et al. |
| 9,101,506 B2 | 8/2015 | Arbefeuille et al. |
| 9,113,999 B2 | 8/2015 | Taylor et al. |
| 9,119,717 B2 | 9/2015 | Wang et al. |
| 9,125,765 B2 | 9/2015 | Melsheimer |

(56) References Cited

U.S. PATENT DOCUMENTS

| | | |
|---|---|---|
| 9,149,379 B2 | 10/2015 | Keady et al. |
| 9,192,492 B2 | 11/2015 | Seguin et al. |
| 9,192,496 B2 | 11/2015 | Robinson |
| 9,192,500 B1 | 11/2015 | Longo et al. |
| 9,198,783 B2 | 12/2015 | Douk et al. |
| 9,216,082 B2 | 12/2015 | Von Segesser et al. |
| 9,237,959 B2 | 1/2016 | Cage |
| 9,241,702 B2 | 1/2016 | Maisano et al. |
| 9,295,571 B2 | 3/2016 | Newell et al. |
| 9,301,864 B2 | 4/2016 | Kao |
| 9,314,327 B2 | 4/2016 | Orr |
| 9,314,360 B2 | 4/2016 | Kao |
| 9,339,404 B2 | 5/2016 | Snow et al. |
| 9,345,597 B2 | 5/2016 | Pacetti |
| 9,364,350 B2 | 6/2016 | Pacetti et al. |
| 9,370,437 B2 | 6/2016 | Chuter et al. |
| 9,375,327 B2 | 6/2016 | Giasolli et al. |
| 9,375,336 B1 | 6/2016 | Longo et al. |
| 9,398,967 B2 | 7/2016 | Cornelius |
| 9,408,731 B2 | 8/2016 | Hartley et al. |
| 9,421,115 B2 | 8/2016 | Wübbeling et al. |
| 9,427,340 B2 | 8/2016 | Yadin |
| 9,433,520 B2 | 9/2016 | Longo |
| 9,439,795 B2 | 9/2016 | Wang et al. |
| 9,445,929 B2 | 9/2016 | Longo et al. |
| 9,452,067 B2 | 9/2016 | Wu |
| 9,480,826 B2 | 11/2016 | Schneider et al. |
| 9,498,296 B2 | 11/2016 | Hingston et al. |
| 9,498,322 B2 | 11/2016 | Thomas |
| 9,539,130 B2 | 1/2017 | Farag et al. |
| 9,545,322 B2 | 1/2017 | Schneider et al. |
| 9,566,179 B2 | 2/2017 | Andreas et al. |
| 9,585,777 B2 | 3/2017 | Pacetti |
| 9,597,213 B2 | 3/2017 | Green |
| 9,603,696 B2 | 3/2017 | Hartley et al. |
| 9,603,730 B2 | 3/2017 | Giasolli et al. |
| 9,603,980 B2 | 3/2017 | Zhao |
| 9,662,231 B2 | 5/2017 | Ngo et al. |
| 9,668,892 B2 | 6/2017 | Shalev et al. |
| 9,700,448 B2 | 7/2017 | Snow et al. |
| 9,707,115 B2 | 7/2017 | Masakazu |
| 9,724,224 B2 | 8/2017 | Gillick et al. |
| 9,730,818 B2 | 8/2017 | Giasolli et al. |
| 9,737,368 B2 | 8/2017 | Lumauig |
| 9,867,699 B2 | 1/2018 | Straubinger et al. |
| 9,877,828 B2 | 1/2018 | Straubinger et al. |
| 9,895,243 B2 | 2/2018 | Kariniemi et al. |
| 9,908,297 B2 | 3/2018 | Pacetti et al. |
| 9,918,835 B2 | 3/2018 | Guyenot et al. |
| 9,931,193 B2 | 4/2018 | Cully et al. |
| 9,943,428 B2 | 4/2018 | Burkart et al. |
| 9,974,670 B2 | 5/2018 | Schneider et al. |
| 9,987,154 B2 | 6/2018 | Pacetti et al. |
| 10,016,292 B2 | 7/2018 | Senness et al. |
| 10,022,250 B2 | 7/2018 | Giasolli et al. |
| 10,098,764 B2 | 10/2018 | Pacetti |
| 10,111,741 B2 | 10/2018 | Michalak |
| 10,117,762 B2 | 11/2018 | Giasolli et al. |
| 10,137,013 B2 | 11/2018 | Giasolli et al. |
| 10,166,127 B2 | 1/2019 | Giasolli et al. |
| 10,188,533 B2 | 1/2019 | Schneider et al. |
| 10,231,853 B2 | 3/2019 | Weber |
| 10,231,854 B2 | 3/2019 | Wack |
| 10,238,339 B2 | 3/2019 | Dlugach et al. |
| 10,245,167 B2 | 4/2019 | Longo |
| 10,245,168 B2 | 4/2019 | Amendt et al. |
| 10,271,970 B2 | 4/2019 | Paul et al. |
| 10,271,973 B2 | 4/2019 | Giasolli et al. |
| 10,278,839 B2 | 5/2019 | Giasolli et al. |
| 10,285,831 B2 | 5/2019 | Giasolli et al. |
| 10,292,845 B2 | 5/2019 | Higashi et al. |
| 10,299,945 B2 | 5/2019 | Schneider et al. |
| 10,390,977 B2 | 8/2019 | Giasolli et al. |
| 10,660,771 B2 | 5/2020 | Giasolli et al. |
| 10,702,679 B2 | 7/2020 | Chanduszko et al. |
| 2002/0052640 A1* | 5/2002 | Bigus ............ A61F 2/07 623/1.11 |
| 2002/0120323 A1 | 8/2002 | Thompson |
| 2002/0123790 A1 | 9/2002 | White et al. |
| 2002/0165599 A1 | 11/2002 | Nasralla |
| 2002/0169495 A1 | 11/2002 | Gifford et al. |
| 2003/0055480 A1 | 3/2003 | Fischell et al. |
| 2003/0055491 A1 | 3/2003 | Schwartz et al. |
| 2003/0069630 A1 | 4/2003 | Burgermeister et al. |
| 2003/0074049 A1 | 4/2003 | Hoganson et al. |
| 2003/0130720 A1 | 7/2003 | DePalma et al. |
| 2003/0220683 A1 | 11/2003 | Minasian et al. |
| 2003/0225446 A1 | 12/2003 | Hartley |
| 2003/0225448 A1 | 12/2003 | Gerberding |
| 2004/0010307 A1 | 1/2004 | Grad et al. |
| 2004/0186551 A1 | 9/2004 | Kao et al. |
| 2004/0215324 A1 | 10/2004 | Vonderwalde et al. |
| 2004/0267281 A1 | 12/2004 | Harari et al. |
| 2004/0267348 A1 | 12/2004 | Gunderson et al. |
| 2005/0010275 A1 | 1/2005 | Sahatjian et al. |
| 2005/0021123 A1 | 1/2005 | Dorn et al. |
| 2005/0096731 A1 | 5/2005 | Looi et al. |
| 2005/0149163 A1 | 7/2005 | Sahota |
| 2005/0246008 A1 | 11/2005 | Hogendijk et al. |
| 2005/0251164 A1 | 11/2005 | Gifford, III et al. |
| 2005/0273151 A1 | 12/2005 | Fulkerson |
| 2005/0278011 A1 | 12/2005 | Peckham |
| 2005/0288764 A1 | 12/2005 | Snow et al. |
| 2005/0288766 A1 | 12/2005 | Plain et al. |
| 2006/0069424 A1 | 3/2006 | Acosta et al. |
| 2006/0074478 A1 | 4/2006 | Feller, III |
| 2006/0111769 A1 | 5/2006 | Murray |
| 2006/0184225 A1 | 8/2006 | Pryor |
| 2006/0184227 A1 | 8/2006 | Rust |
| 2006/0206190 A1 | 9/2006 | Chermoni |
| 2006/0248698 A1 | 11/2006 | Hanson et al. |
| 2006/0265040 A1 | 11/2006 | Murray |
| 2006/0282149 A1 | 12/2006 | Kao |
| 2007/0088420 A1 | 4/2007 | Andreas et al. |
| 2007/0093744 A1 | 4/2007 | Elmaleh |
| 2007/0142892 A1 | 6/2007 | Dave et al. |
| 2007/0156223 A1 | 7/2007 | Vaughan |
| 2007/0156224 A1 | 7/2007 | Cioanta et al. |
| 2007/0156225 A1 | 7/2007 | George et al. |
| 2007/0156226 A1 | 7/2007 | Chew et al. |
| 2007/0179587 A1 | 8/2007 | Acosta et al. |
| 2007/0191926 A1 | 8/2007 | Nikanorov et al. |
| 2008/0033522 A1 | 2/2008 | Grewe et al. |
| 2008/0051867 A1 | 2/2008 | Davila et al. |
| 2008/0077229 A1 | 3/2008 | Andres et al. |
| 2008/0082154 A1 | 4/2008 | Tseng et al. |
| 2008/0132999 A1 | 6/2008 | Mericle et al. |
| 2008/0188207 A1 | 8/2008 | Lee |
| 2008/0208327 A1 | 8/2008 | Rowe |
| 2008/0221658 A1 | 9/2008 | Martin et al. |
| 2008/0255653 A1 | 10/2008 | Schkolnik |
| 2008/0264102 A1 | 10/2008 | Berra |
| 2008/0269865 A1 | 10/2008 | Snow et al. |
| 2008/0319528 A1 | 12/2008 | Yribarren et al. |
| 2009/0048654 A1 | 2/2009 | Chmura et al. |
| 2009/0069878 A1 | 3/2009 | Weber et al. |
| 2009/0076594 A1 | 3/2009 | Sabaria |
| 2009/0082841 A1 | 3/2009 | Zacharias et al. |
| 2009/0099641 A1 | 4/2009 | Wu et al. |
| 2009/0149943 A1 | 6/2009 | Tower |
| 2009/0216284 A1 | 8/2009 | Chin et al. |
| 2009/0248141 A1 | 10/2009 | Shandas et al. |
| 2009/0270965 A1 | 10/2009 | Sinha et al. |
| 2009/0270967 A1 | 10/2009 | Fleming, III et al. |
| 2009/0276031 A1* | 11/2009 | Kao ............ A61F 2/958 623/1.11 |
| 2010/0049292 A1 | 2/2010 | Fiorella |
| 2010/0131045 A1 | 5/2010 | Globerman et al. |
| 2010/0137966 A1 | 6/2010 | Magnuson |
| 2010/0145431 A1 | 6/2010 | Wu et al. |
| 2010/0228333 A1 | 9/2010 | Drasler et al. |
| 2010/0318173 A1 | 12/2010 | Kolandaivelu et al. |
| 2011/0077731 A1 | 3/2011 | Lee et al. |
| 2011/0190864 A1 | 8/2011 | McClain et al. |

(56) References Cited

U.S. PATENT DOCUMENTS

| | | |
|---|---|---|
| 2011/0230954 A1 | 9/2011 | Schneider et al. |
| 2012/0016457 A1 | 1/2012 | Chobotov et al. |
| 2012/0041469 A1 | 2/2012 | Fischell et al. |
| 2012/0065722 A1 | 3/2012 | Pacetti |
| 2012/0172963 A1 | 7/2012 | Ryan et al. |
| 2012/0191176 A1 | 7/2012 | Nagi et al. |
| 2012/0226343 A1 | 9/2012 | Vo et al. |
| 2012/0283811 A1 | 11/2012 | Neilan |
| 2012/0302952 A1* | 11/2012 | Kitada ............... A61M 25/0043 604/525 |
| 2013/0116655 A1* | 5/2013 | Bacino ............ A61M 25/10184 604/509 |
| 2014/0088565 A1 | 3/2014 | Vongphakdy et al. |
| 2014/0094929 A1 | 4/2014 | Shin et al. |
| 2014/0107761 A1 | 4/2014 | Gale et al. |
| 2014/0194967 A1 | 7/2014 | Schneider et al. |
| 2014/0214068 A1 | 7/2014 | Zhu et al. |
| 2016/0192942 A1 | 7/2016 | Strauss et al. |
| 2016/0242943 A1 | 8/2016 | Riedy et al. |
| 2016/0374839 A1 | 12/2016 | Longo et al. |
| 2017/0112647 A1 | 4/2017 | Sachar |
| 2017/0113025 A1 | 4/2017 | Chanduszko et al. |
| 2017/0181873 A1 | 6/2017 | Schneider et al. |
| 2017/0231751 A1 | 8/2017 | Barthold et al. |
| 2017/0281375 A1 | 10/2017 | Longo et al. |
| 2017/0296366 A1 | 10/2017 | Giasolli et al. |
| 2017/0319364 A1 | 11/2017 | Jung et al. |
| 2017/0367856 A1 | 12/2017 | Tanaka et al. |
| 2018/0000619 A1 | 1/2018 | Longo et al. |
| 2018/0008444 A1* | 1/2018 | Merk ..................... A61F 2/82 |
| 2018/0028306 A1 | 2/2018 | Gonzalez et al. |
| 2018/0154123 A1 | 6/2018 | Werneth et al. |
| 2018/0207008 A1 | 7/2018 | Giasolli et al. |
| 2018/0272044 A1 | 9/2018 | Hossainy et al. |
| 2018/0318116 A1 | 11/2018 | Eli et al. |
| 2019/0008667 A1 | 1/2019 | Longo |
| 2019/0069985 A1 | 3/2019 | Nennig et al. |
| 2019/0070025 A1 | 3/2019 | Fu et al. |
| 2019/0192319 A1 | 6/2019 | Giasolli et al. |
| 2019/0192321 A1 | 6/2019 | Schneider et al. |
| 2019/0282381 A1 | 9/2019 | Giasolli et al. |
| 2019/0298555 A1 | 10/2019 | Longo |

FOREIGN PATENT DOCUMENTS

| | | |
|---|---|---|
| AU | 2014201067 | 3/2014 |
| AU | 2010259907 | 8/2015 |
| AU | 2013212056 | 7/2016 |
| AU | 2015207895 | 5/2017 |
| AU | 2014280976 | 7/2017 |
| CA | 2705275 | 7/2013 |
| CN | 1856280 | 11/2006 |
| CN | 101102728 | 1/2008 |
| CN | 101262835 | 9/2008 |
| CN | 101754727 | 6/2010 |
| CN | 101909552 | 12/2010 |
| CN | 102164565 | 8/2011 |
| CN | 102292036 | 12/2011 |
| CN | 102573701 | 7/2012 |
| CN | 102724931 | 10/2012 |
| CN | 104042380 | 9/2014 |
| CN | 103313682 | 8/2016 |
| CN | 104220026 | 9/2016 |
| CN | 106466205 | 3/2017 |
| CN | 106473786 | 3/2017 |
| CN | 106473849 | 3/2017 |
| CN | 107028691 | 8/2017 |
| CN | 107157632 | 9/2017 |
| CN | 107205834 | 9/2017 |
| CN | 107405208 | 11/2017 |
| CN | 104887365 | 12/2017 |
| CN | 107427375 | 12/2017 |
| DE | 60030705 | 5/2007 |
| DE | 10 2009 041 025 | 3/2011 |
| DE | 20 2011 107 781 | 12/2011 |
| DE | 20 2011 110 714 | 12/2015 |
| DE | 10 2014 016 588 | 5/2016 |
| DE | 20 2011 110818 | 9/2016 |
| DK | 2775968 | 12/2017 |
| EP | 0497620 | 8/1992 |
| EP | 0714640 | 6/1996 |
| EP | 0855883 | 8/1998 |
| EP | 0812580 | 2/2004 |
| EP | 1393766 | 3/2004 |
| EP | 1236446 | 8/2005 |
| EP | 1787593 | 5/2007 |
| EP | 1803423 | 7/2007 |
| EP | 1894545 | 3/2008 |
| EP | 1452151 | 10/2008 |
| EP | 1567093 | 1/2009 |
| EP | 1378212 | 9/2009 |
| EP | 2219535 | 8/2010 |
| EP | 2440155 | 4/2012 |
| EP | 1729682 | 4/2013 |
| EP | 1786367 | 4/2013 |
| EP | 1973502 | 4/2014 |
| EP | 2806826 | 12/2014 |
| EP | 2881086 | 6/2015 |
| EP | 2699207 | 10/2015 |
| EP | 2590602 | 12/2015 |
| EP | 3015078 | 5/2016 |
| EP | 3058900 | 8/2016 |
| EP | 1689327 | 9/2016 |
| EP | 3072463 | 9/2016 |
| EP | 3187222 | 7/2017 |
| EP | 2775968 | 9/2017 |
| EP | 3217927 | 9/2017 |
| EP | 2967830 | 11/2017 |
| EP | 3250159 | 12/2017 |
| EP | 3421010 | 1/2019 |
| FR | 2714816 | 7/1995 |
| GB | 201106757 | 6/2011 |
| JP | H06-000221 | 1/1994 |
| JP | H08-332229 | 12/1996 |
| JP | H11-501526 | 2/1999 |
| JP | H11-506665 | 6/1999 |
| JP | 2002-513298 | 5/2002 |
| JP | 2007-503923 | 3/2007 |
| JP | 2007-504897 | 3/2007 |
| JP | 2007-508112 | 4/2007 |
| JP | 2008-504078 | 2/2008 |
| JP | 2008-507376 | 3/2008 |
| JP | 2008-510587 | 4/2008 |
| JP | 2008-246214 | 10/2008 |
| JP | 2008-537891 | 10/2008 |
| JP | 2009-532115 | 9/2009 |
| JP | 2010-516333 | 5/2010 |
| JP | 2012-523922 | 10/2012 |
| JP | 2016-135278 | 7/2016 |
| JP | 2016-147051 | 8/2016 |
| JP | 6006808 | 10/2016 |
| KR | 10-2017-0084214 | 7/2017 |
| WO | WO-9508965 A1 * | 4/1995 ............ A61F 2/958 |
| WO | WO 1996/002211 | 2/1996 |
| WO | WO 1996/009013 | 3/1996 |
| WO | WO 1996/037167 | 11/1996 |
| WO | WO 1998/007390 | 2/1998 |
| WO | WO 1999/048440 | 9/1999 |
| WO | WO 1999/049440 | 9/1999 |
| WO | WO 2000/066034 | 11/2000 |
| WO | WO 2001/076509 | 10/2001 |
| WO | WO 2002/034163 | 5/2002 |
| WO | WO 2003/047651 | 6/2003 |
| WO | WO 2003/101310 | 12/2003 |
| WO | WO 2004/006983 | 1/2004 |
| WO | WO 2004/032799 | 4/2004 |
| WO | WO 2004/091441 | 10/2004 |
| WO | WO 2005/039449 | 5/2005 |
| WO | WO 2006/005082 | 1/2006 |
| WO | WO 2006/014767 | 2/2006 |
| WO | WO 2006/026371 | 3/2006 |
| WO | WO 2006/026377 | 3/2006 |
| WO | WO 2006/110258 | 10/2006 |

(56) References Cited

FOREIGN PATENT DOCUMENTS

| WO | WO 2007/088549 | 8/2007 | | |
|---|---|---|---|---|
| WO | WO 2007/109621 | 9/2007 | | |
| WO | WO 2007/118005 | 10/2007 | | |
| WO | WO 2009/076517 | 6/2009 | | |
| WO | WO 2010/037141 | 4/2010 | | |
| WO | WO 2010/044874 | 4/2010 | | |
| WO | WO 2010/118432 | 10/2010 | | |
| WO | WO 2010/144845 | 12/2010 | | |
| WO | WO-2011103107 A1 | * | 8/2011 | ............ A61F 2/2433 |
| WO | WO 2011/153110 | 12/2011 | | |
| WO | WO 2012/006602 | 1/2012 | | |
| WO | WO 2012/143731 | 10/2012 | | |
| WO | WO 2013/068127 | 5/2013 | | |
| WO | WO 2013/112768 | 8/2013 | | |
| WO | WO 2013/118362 | 8/2013 | | |
| WO | WO 2016/074799 | 5/2016 | | |
| WO | WO 2016/122947 | 8/2016 | | |
| WO | WO 2017/117391 | 7/2017 | | |
| WO | WO 2018/175048 | 9/2018 | | |
| WO | WO 2019/023258 | 1/2019 | | |

OTHER PUBLICATIONS

Colombo, A. et al., "Intravascular Ultrasound-Guided Percutaneous Transluminal Coronary Angioplasty With Provisional Spot Stenting for Treatment of Long Coronary Lesions", Journal of the American College of Cardiology, vol. 38, No. 5, Nov. 1, 2001, in 9 pages.

Kokkinidis, D. et al., "Emerging and Future Therapeutic Options for Femoropopliteal and Infrapopliteal Endovascular Intervention", Interventional Cardiology Clinics, vol. 6, 2017, in 17 pages.

Mosseri, M. et al., "New Indicator for Stent Covering Area", in Catheterization and Cardiovascular Diagnosis, 1998, vol. 44, in 5 pages.

Shishehbor, M. et al., "Endovascular Treatment of Femoropopliteal Lesions", Journal of the American College of Cardiology, vol. 66, 2015, in 4 pages.

Zeller, T. et al., "Novel Approaches to the Management of Advanced Peripheral Artery Disease: Perspectives on Drug-Coated Balloons, Drug-Eluting Stents, and Bioresorbable Scaffolds", Current Cardiology Reports, vol. 17, Sep. 2015, in 6 pages.

International Search Report and Written Opinion, re PCT Application No. PCT/US2010/038379, dated Feb. 25, 2011.

International Search Report and Written Opinion, re PCT Application No. PCT/US2011/038468, dated Jan. 18, 2012.

International Search Report and Written Opinion, re PCT Application No. PCT/US2013/023030, dated Apr. 16, 2013.

International Search Report and Written Opinion, re PCT Application No. PCT/US2016/014161, dated Apr. 12, 2016.

International Search Report and Written Opinion, re PCT Application PCT/US2008/086396, dated Jul. 27, 2009.

International Search Report and Written Opinion, re PCT Application PCT/US2011/043471, dated Feb. 9, 2012.

International Search Report and Written Opinion, re PCT Application No. PCT/US2018/043528, dated Sep. 26, 2018.

International Search Report and Written Opinion, re PCT Application No. PCT/US2016/069211, dated Mar. 27, 2017.

* cited by examiner

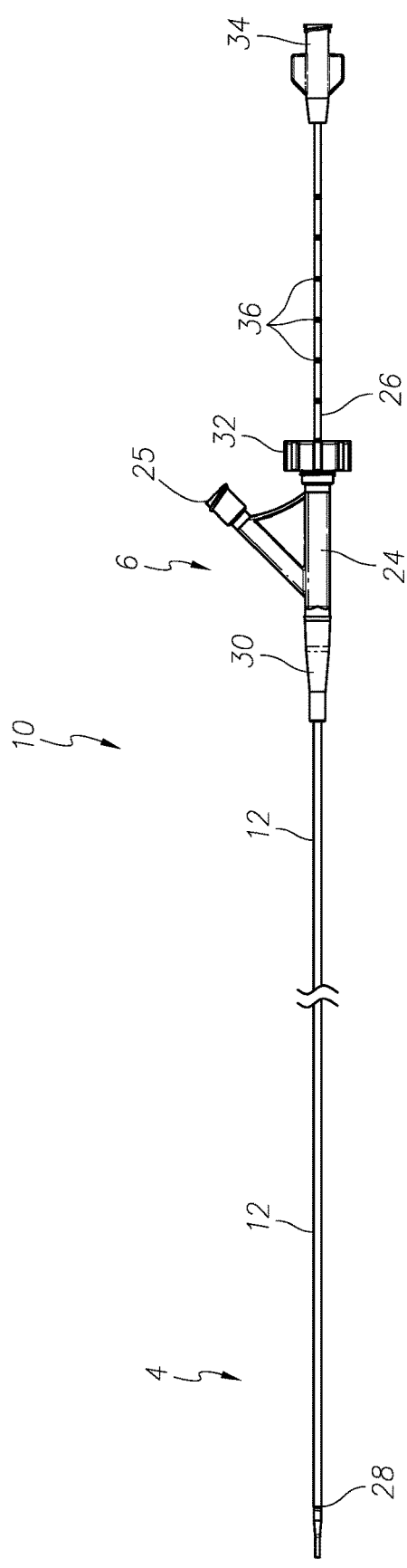
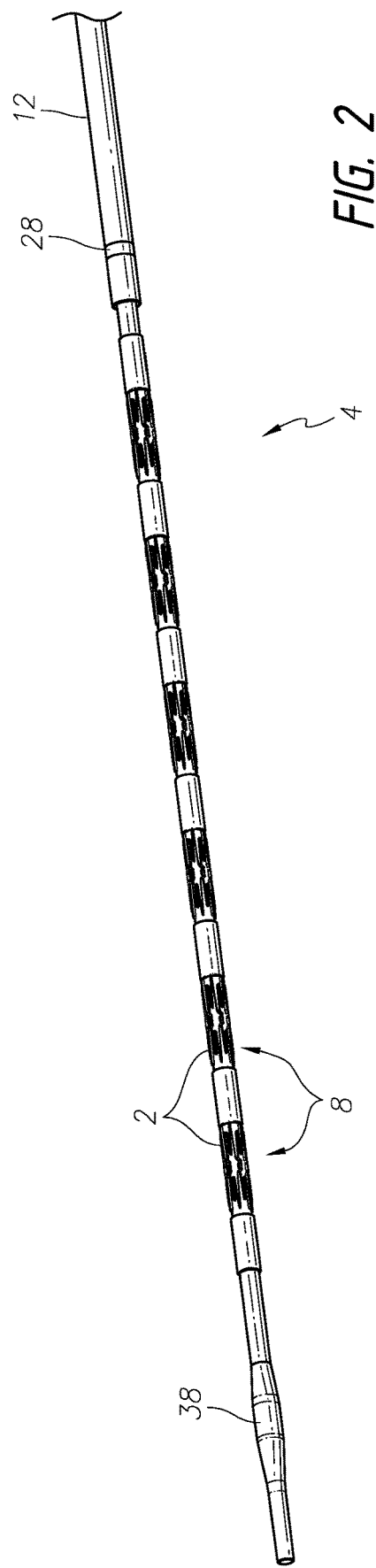

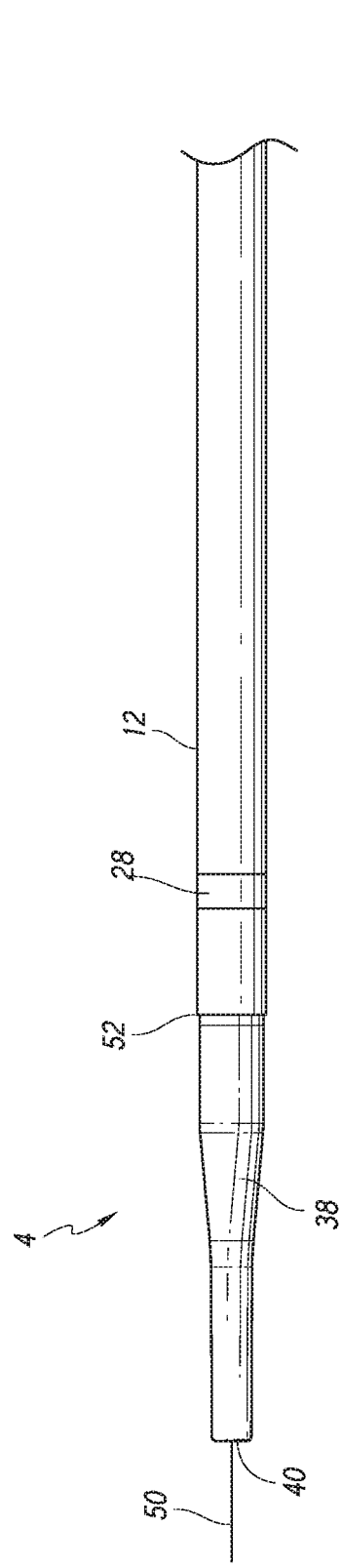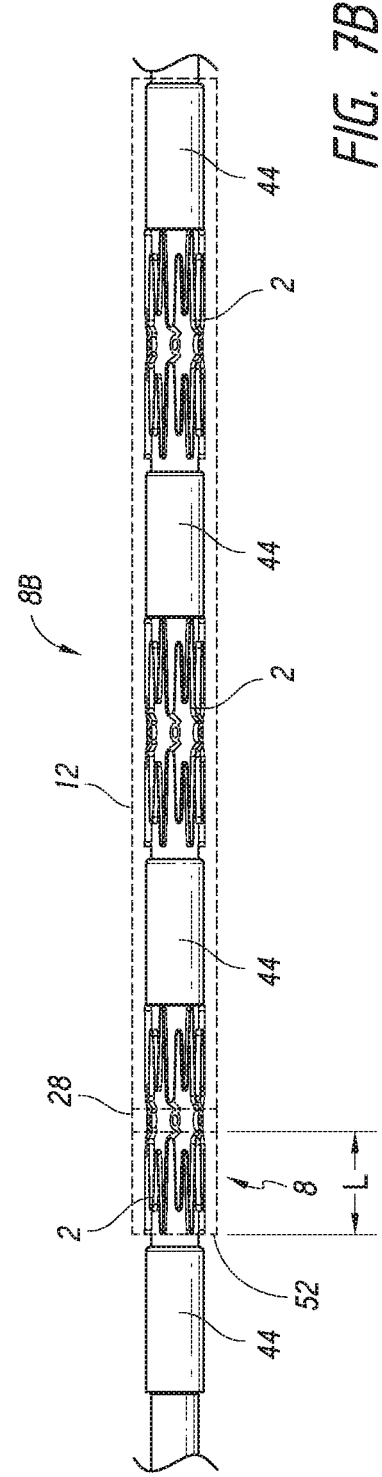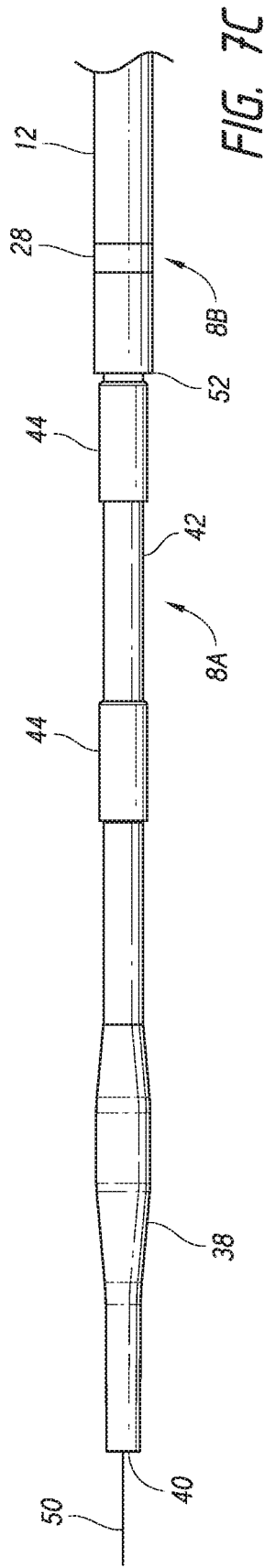

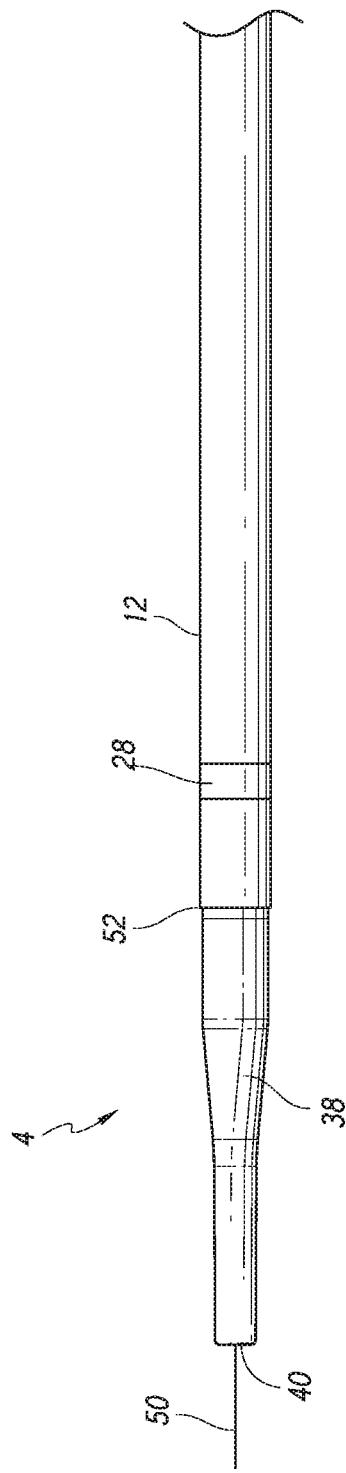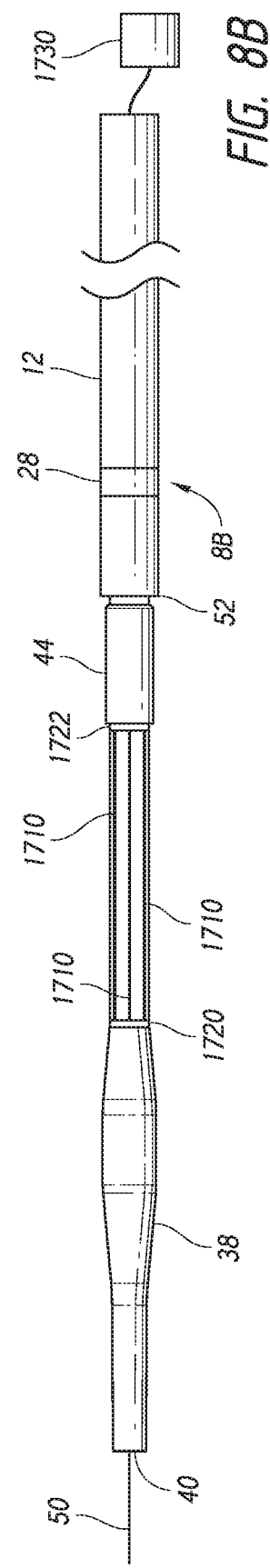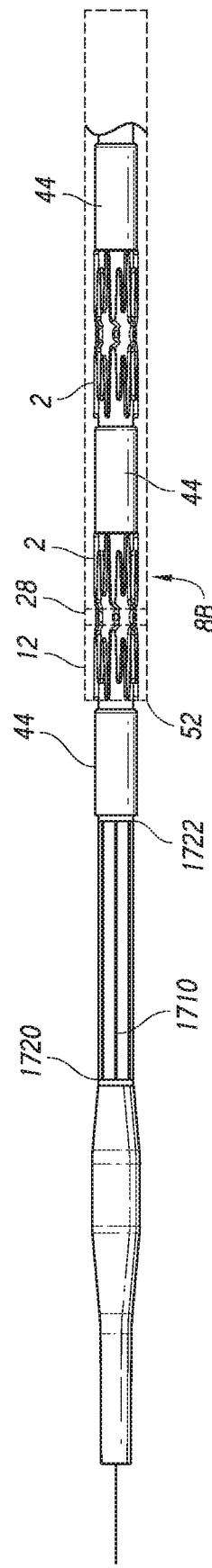

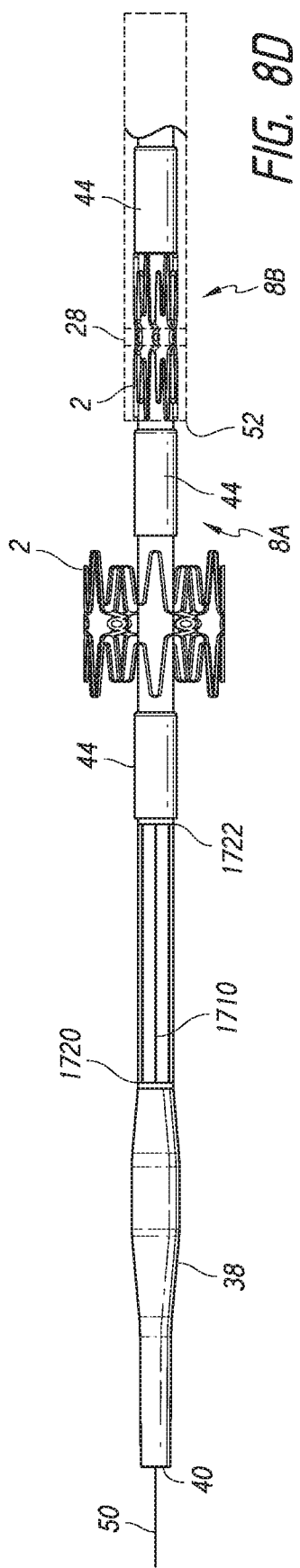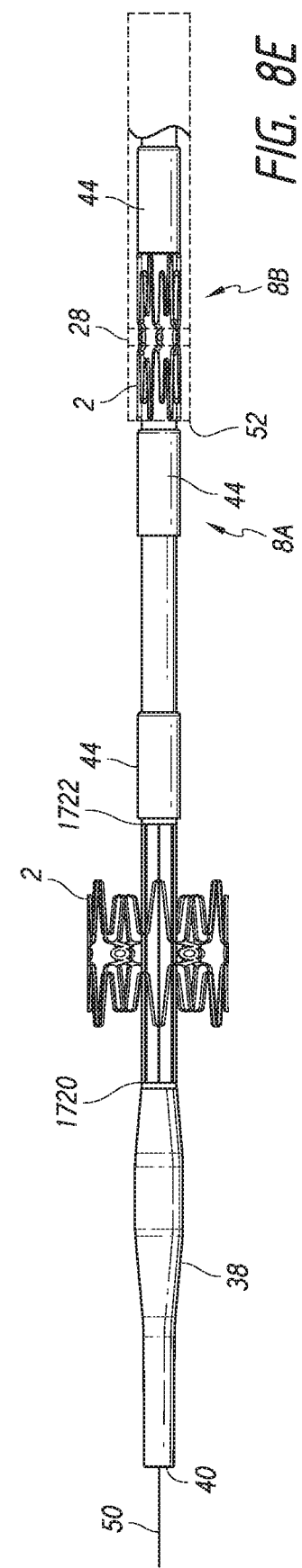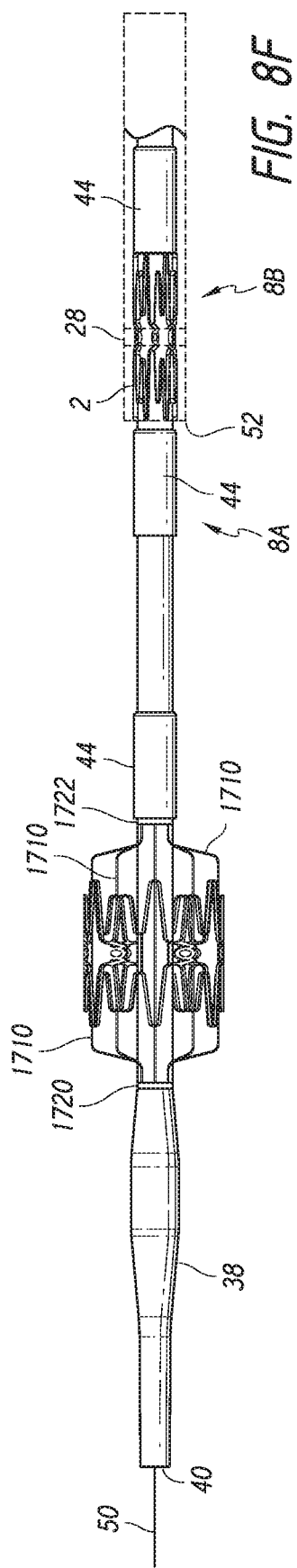

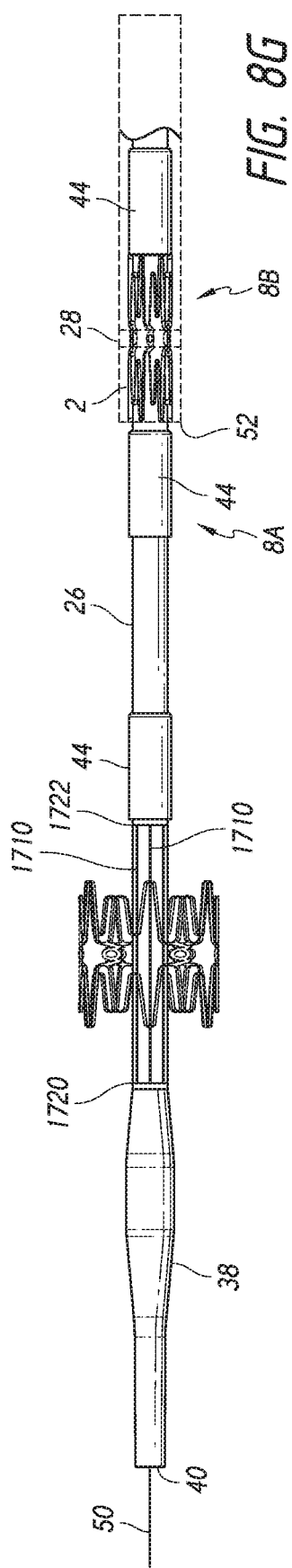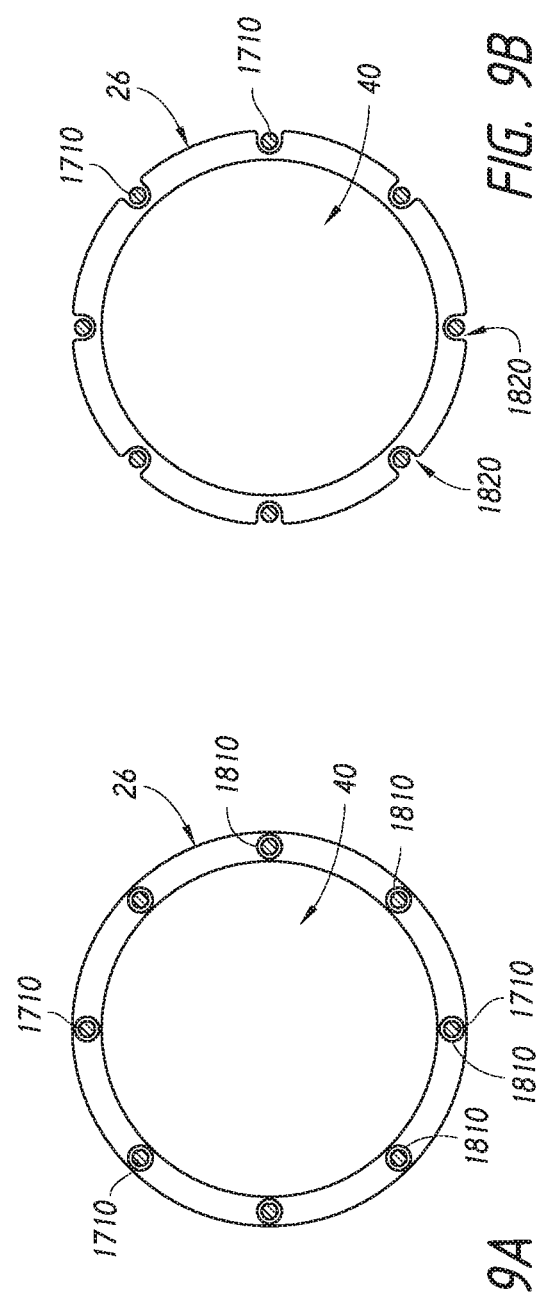

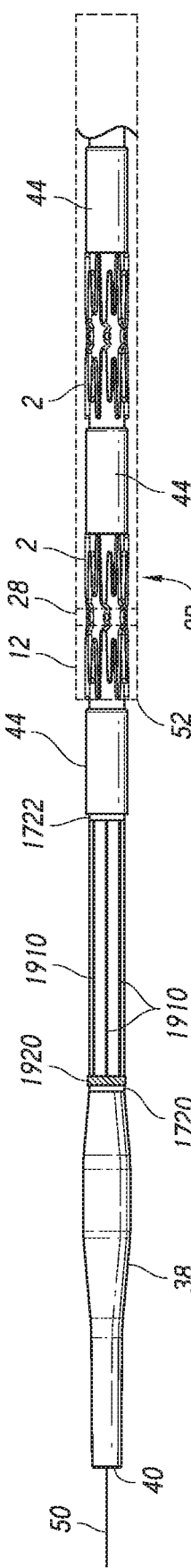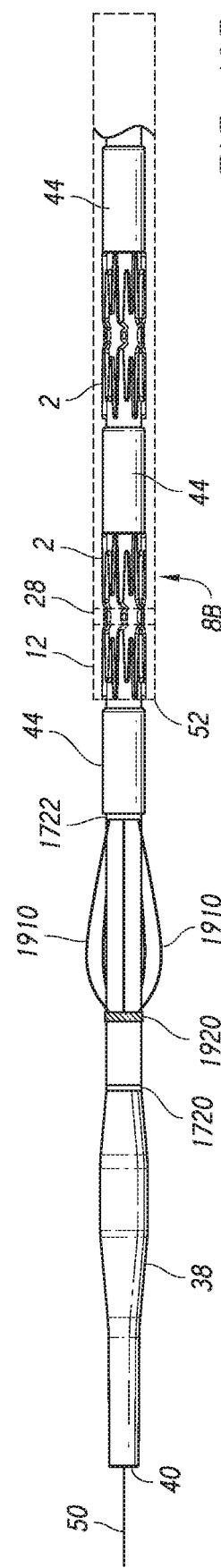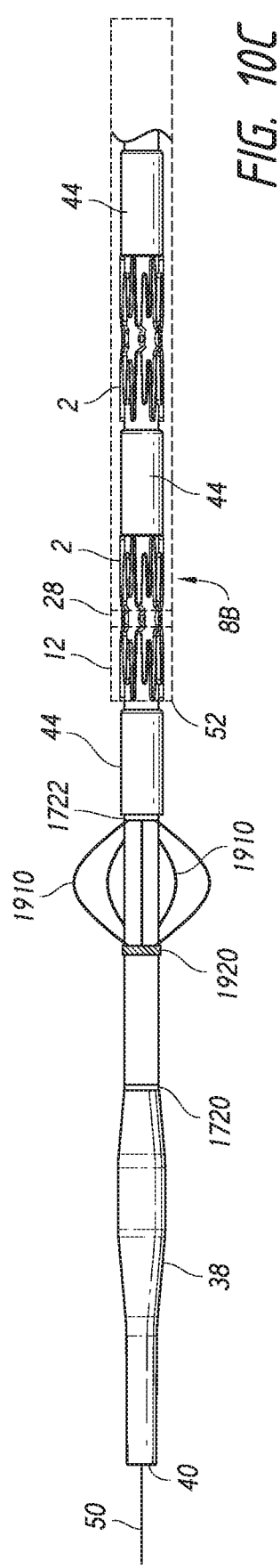

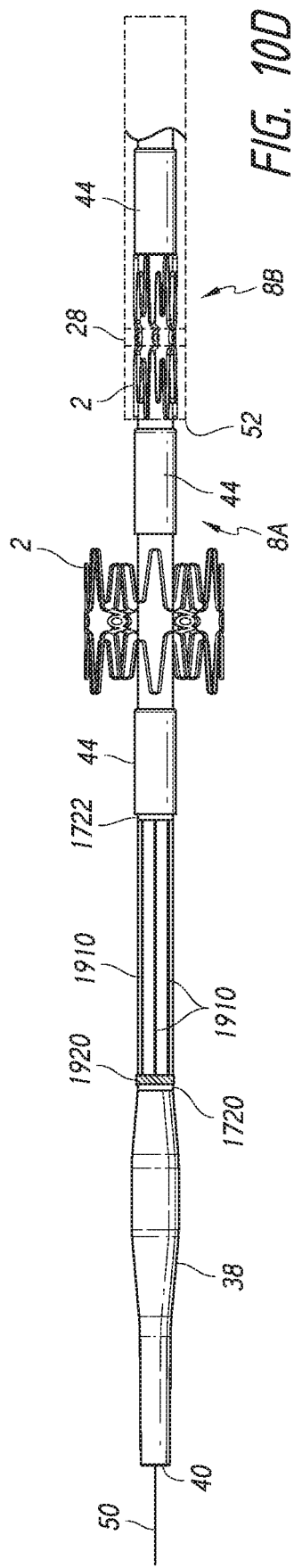
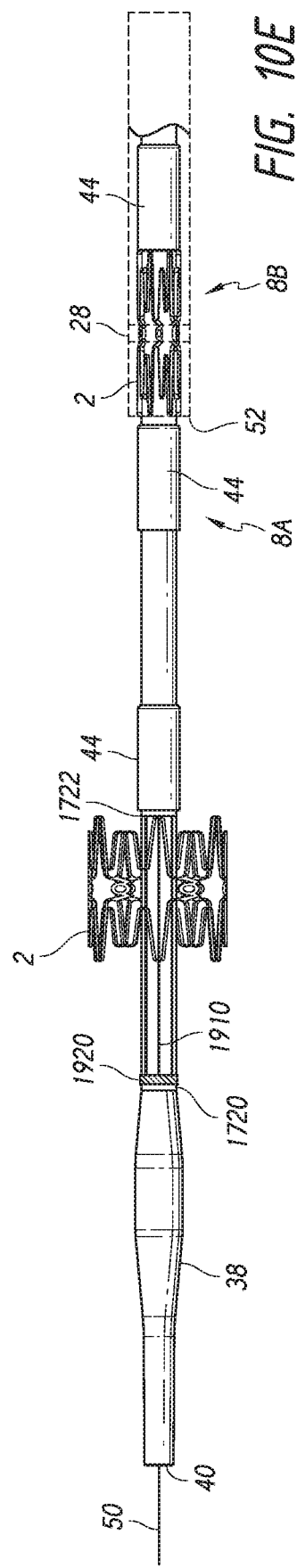
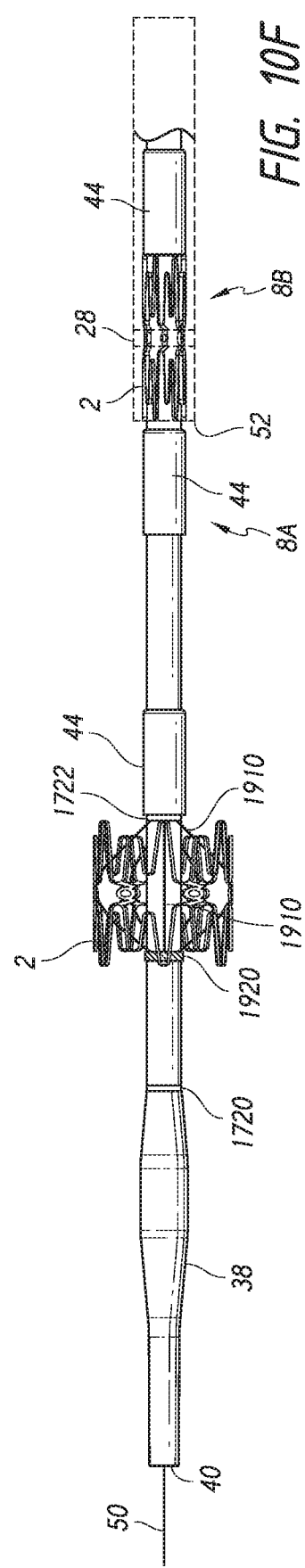

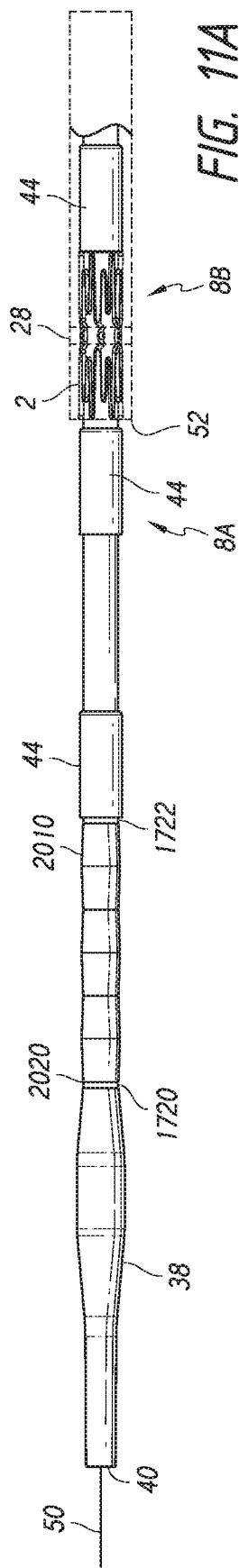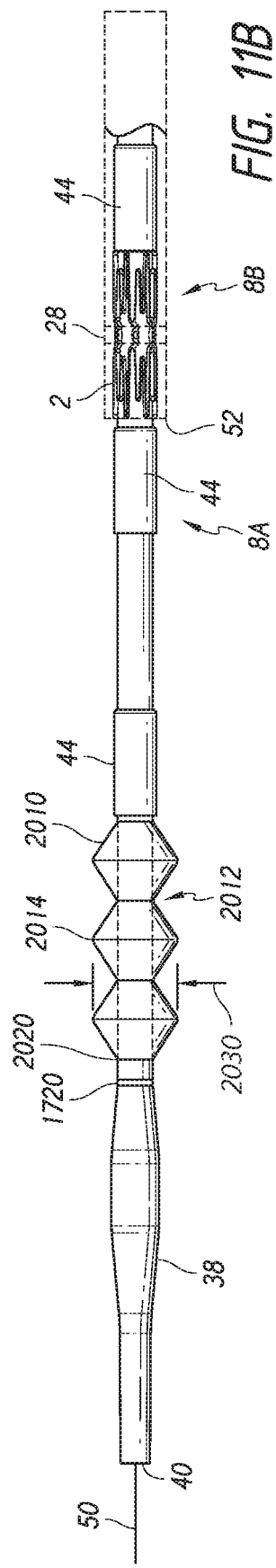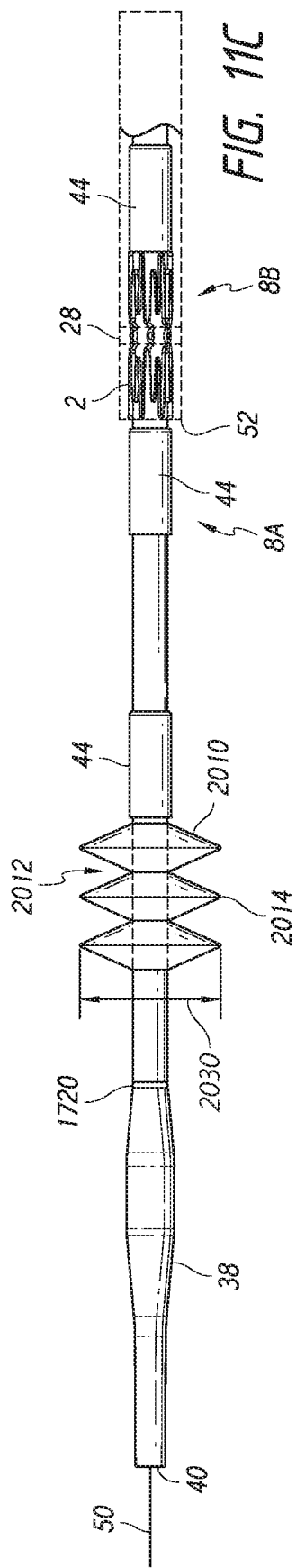

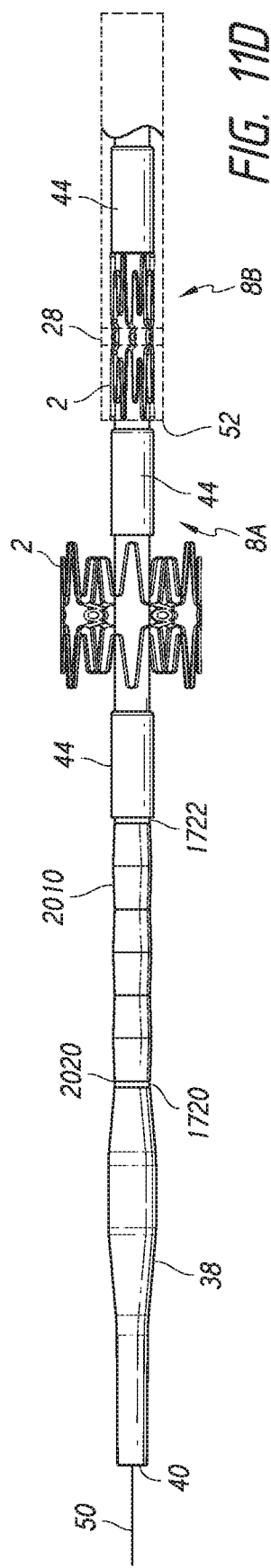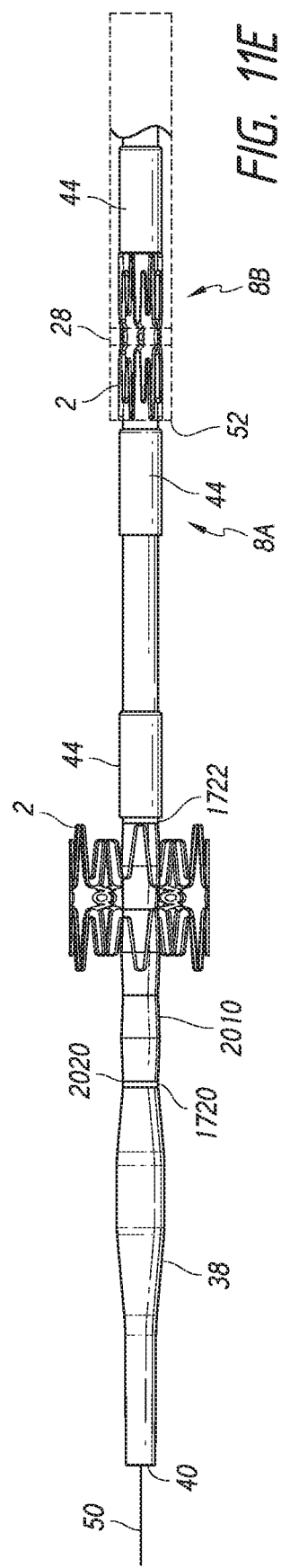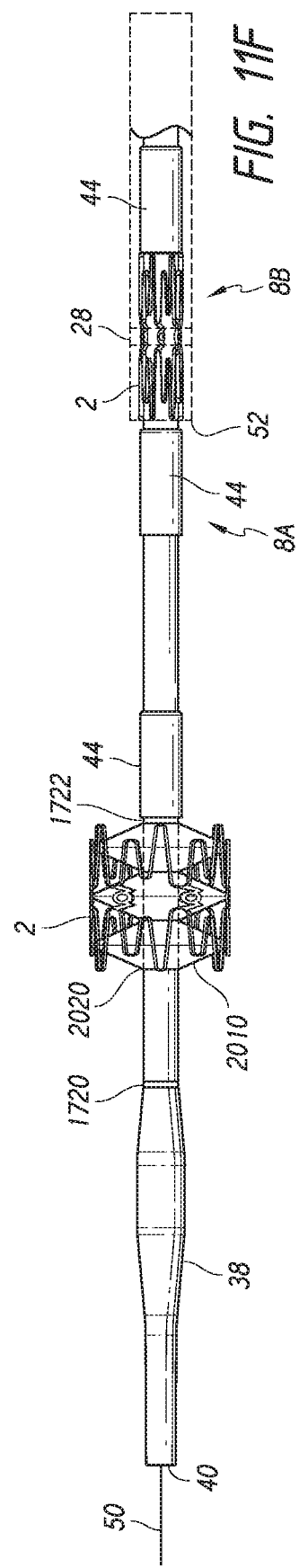

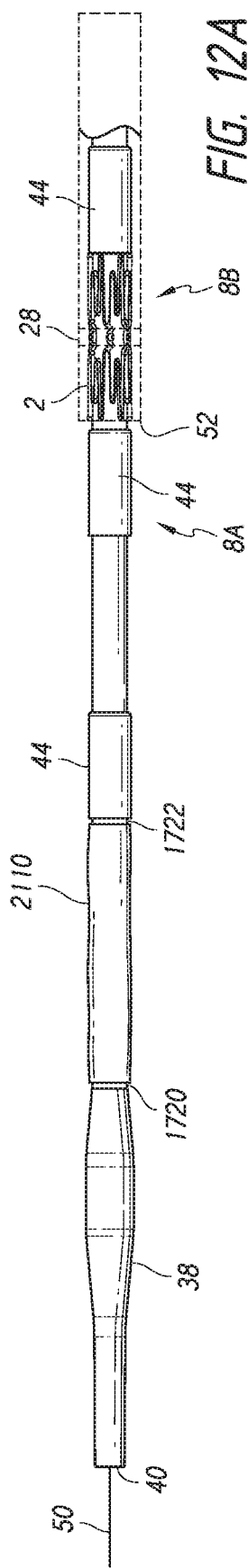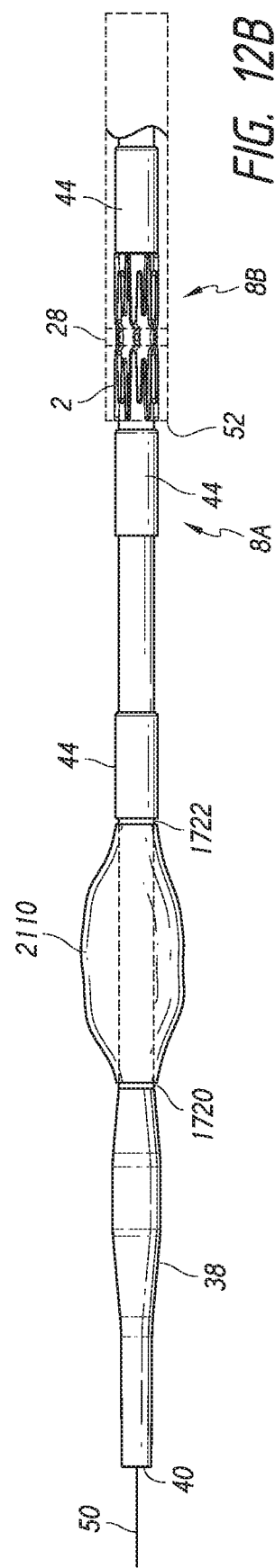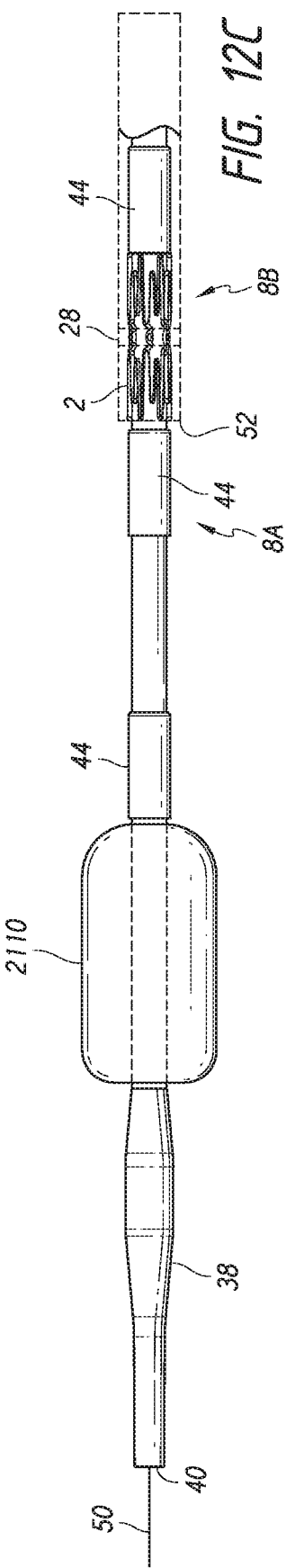

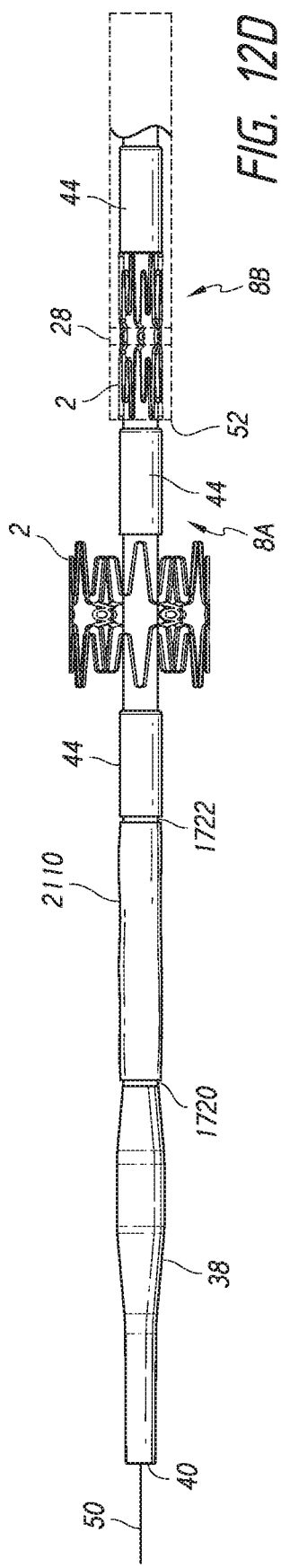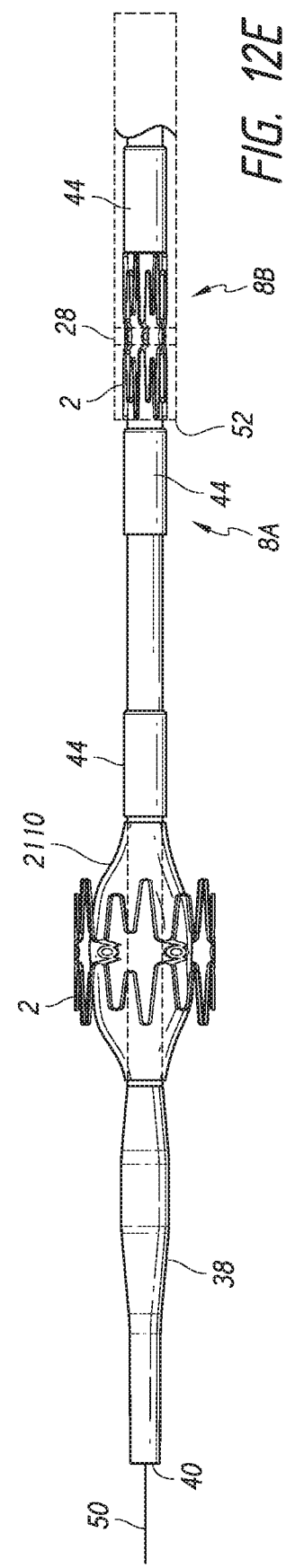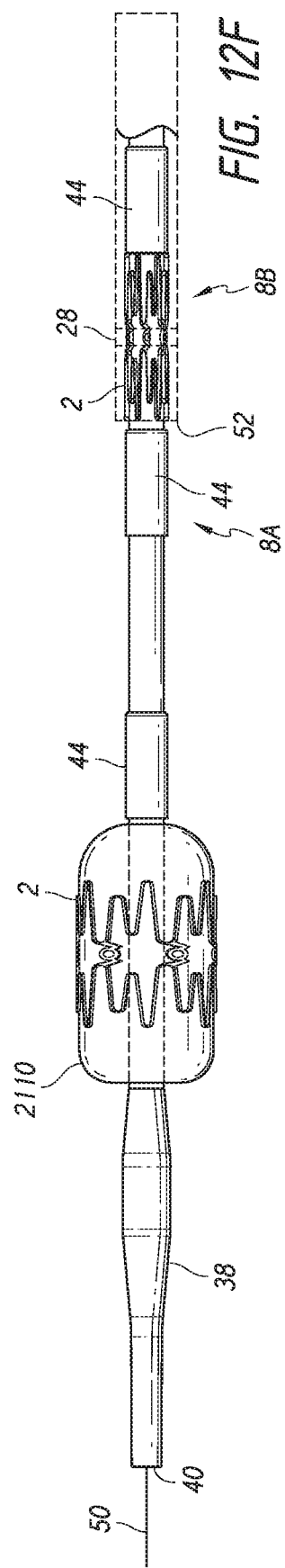

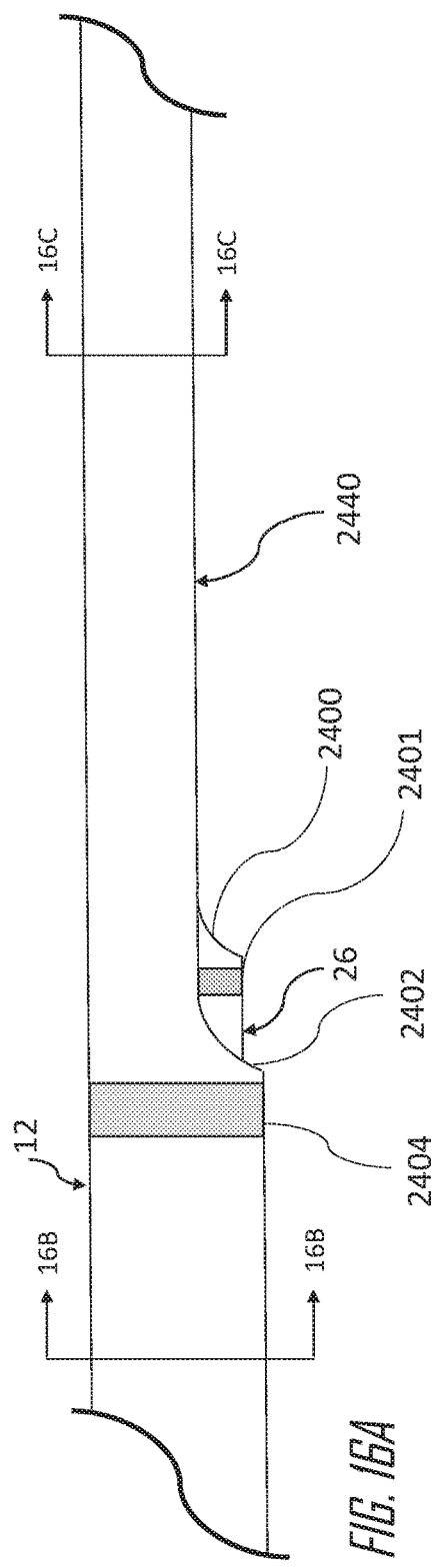
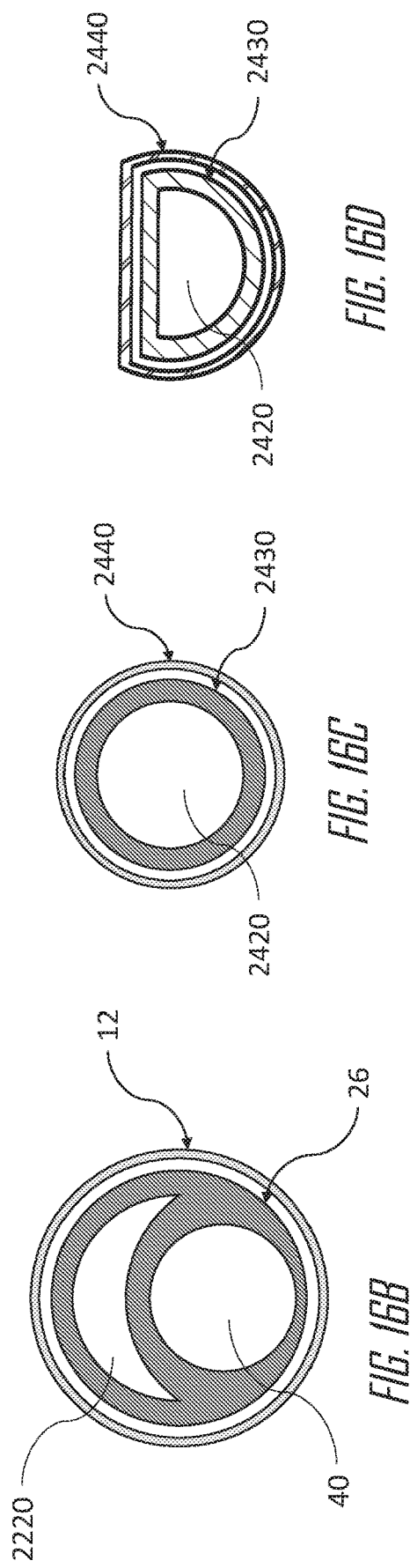

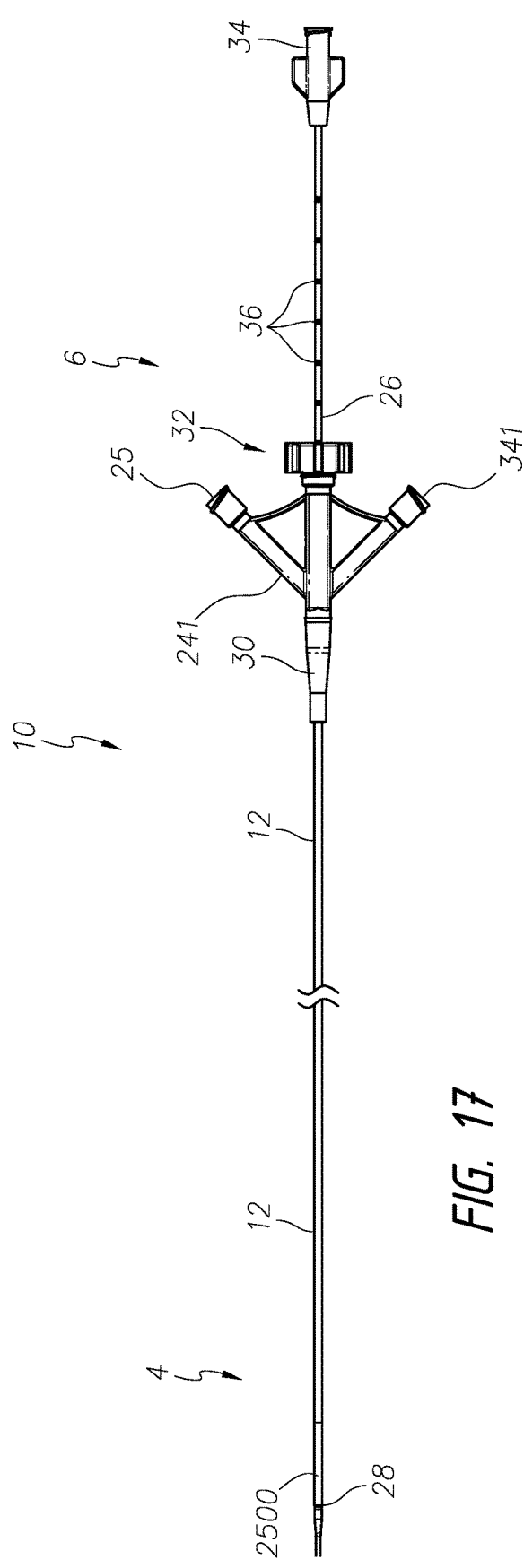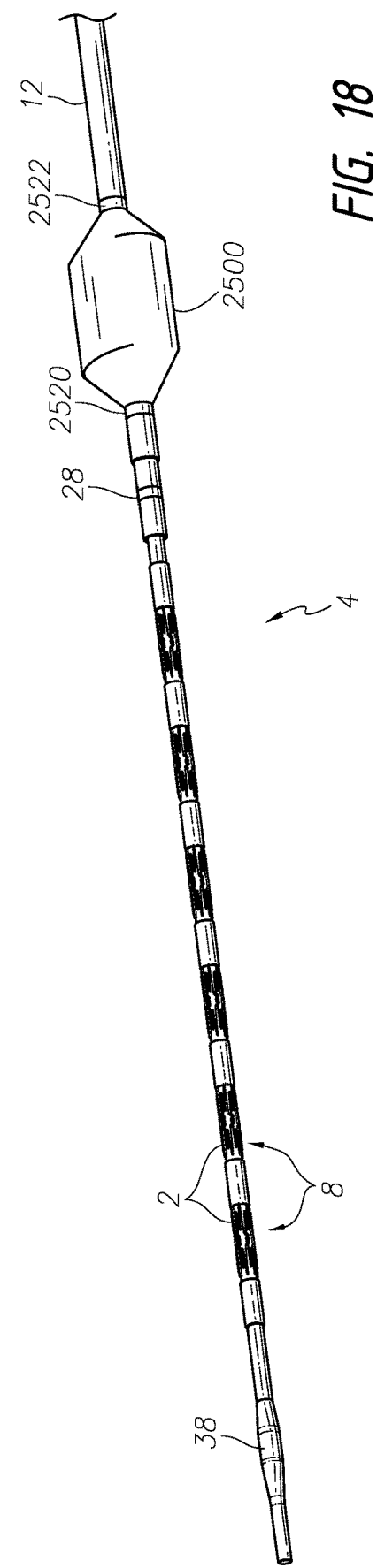

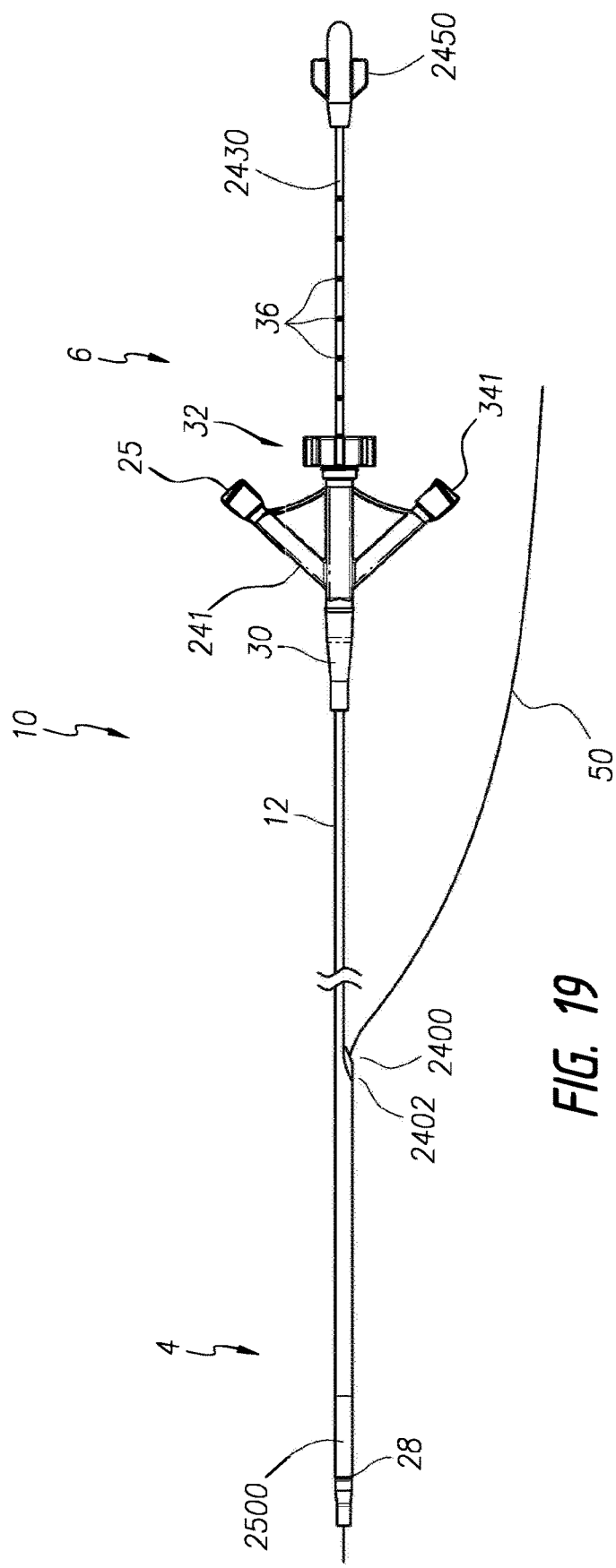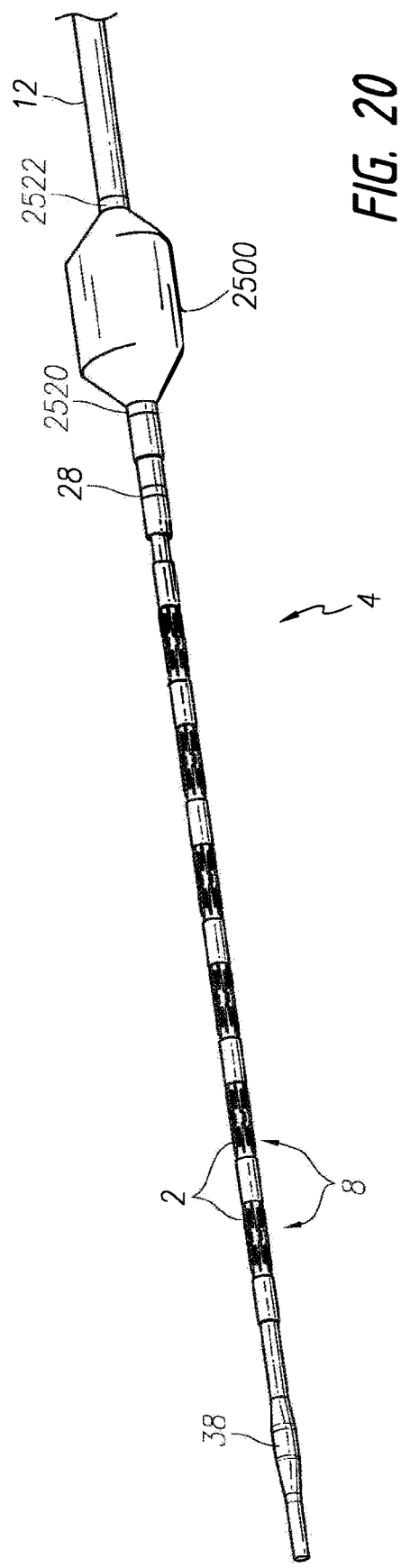

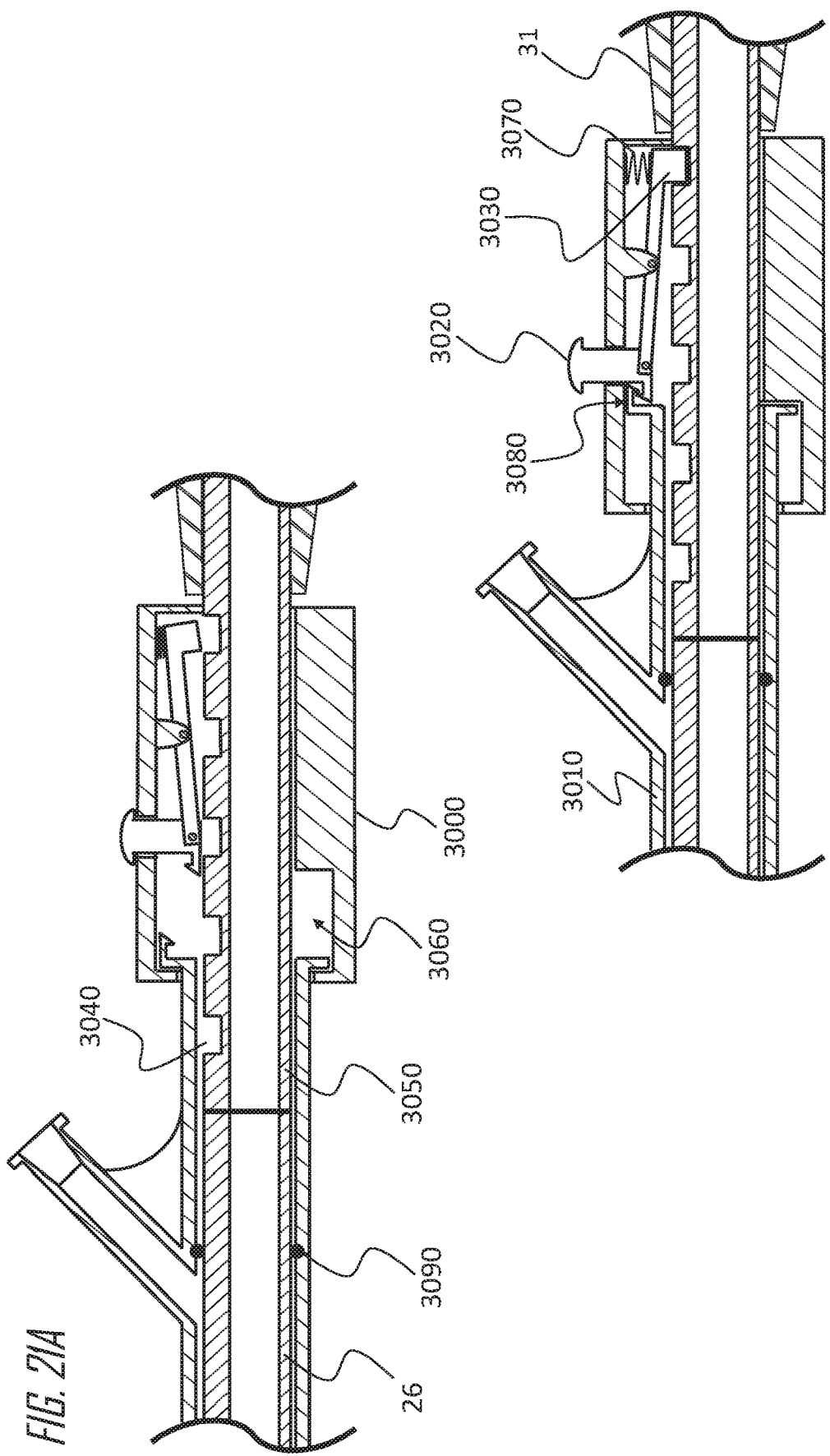

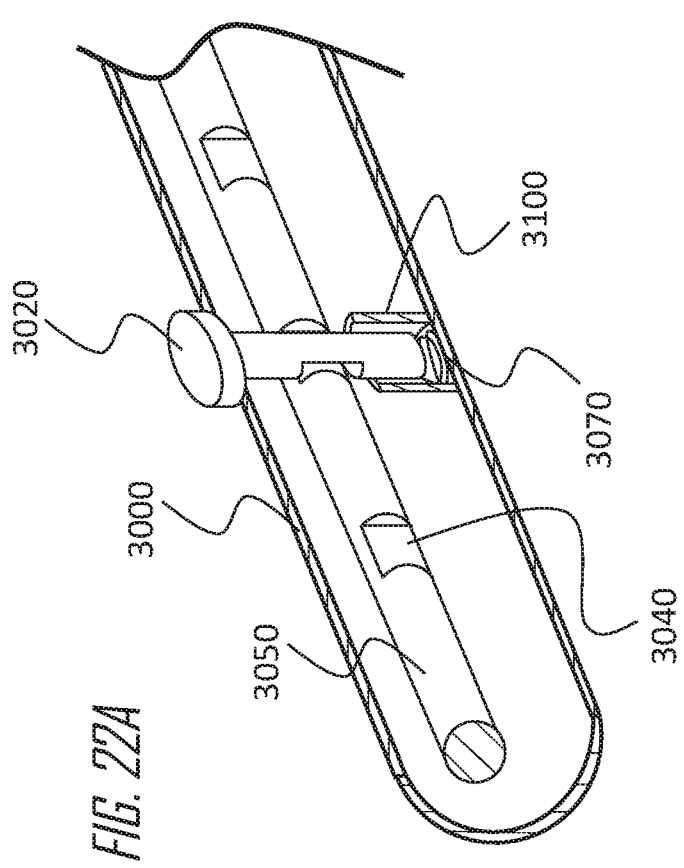
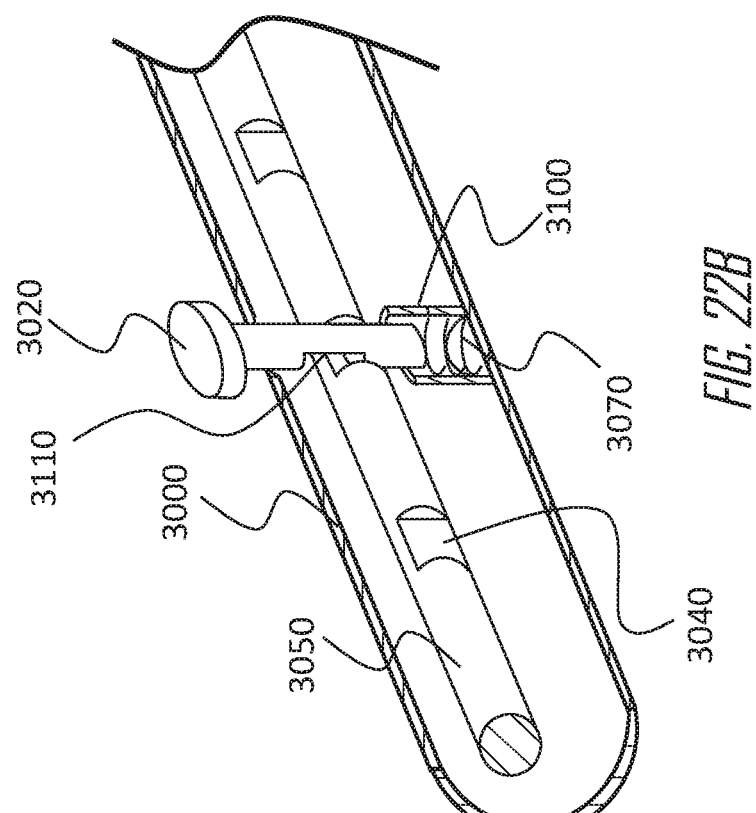

DELIVERY DEVICE AND METHOD OF DELIVERY

INCORPORATION BY REFERENCE

This application claims priority benefit of U.S. patent application Ser. No. 15/705,793, filed Sep. 15, 2017, and U.S. Provisional Pat. Appl. No. 62/536,987, filed Jul. 26, 2017, each of which is incorporated herein by reference in its entirety for all purposes.

BACKGROUND

Field of the Invention

Disclosed herein are delivery devices and methods of delivery. Certain embodiments are described with reference to sequential delivery of multiple intraluminal devices from a delivery device. The delivery devices and methods can be used in procedures where it may be desirable to deploy one or more intraluminal devices, including those procedures which treat atherosclerotic occlusive and vascular disease, though they are not limited to these procedures.

Description of the Related Art

There are a number of medical conditions and procedures in which a device such as a stent is placed in the body to create or maintain a passage. There are a wide variety of stents used for different purposes, from expandable coronary, vascular and biliary stents, to plastic stents used to allow the flow of urine between kidney and bladder.

Stents are often placed in the vascular system after a medical procedure, such as balloon angioplasty. Balloon angioplasty is often used to treat atherosclerotic occlusive disease. Atherosclerotic occlusive disease is the primary cause of stroke, heart attack, limb loss, and death in the US and the industrialized world. Atherosclerotic plaque forms within an artery and can be comprised of calcium, cholesterol, compacted thrombus and cellular debris. As the atherosclerotic disease progresses, the blood supply intended to pass through a specific blood vessel is diminished or even prevented by the occlusive process. One of the most widely utilized methods of treating clinically significant atherosclerotic plaque is balloon angioplasty, which may be followed with stent placement.

SUMMARY

Currently available stents and stent delivery systems have many limitations and drawbacks. For example, they may not be suitable or optimal for all medical procedures, such as for treating dissections, very short lesions, and/or where a high degree of deployed diameter range is desired. There exists a continuing need for improvement in intraluminal devices and associated delivery devices.

According to certain embodiments, a delivery device is provided for sequential delivery of a plurality of intraluminal devices (e.g., stents, tacks, staples, etc.) held in a compressed state on the delivery device. For purposes of this disclosure, the figures depict a tack, which is merely representative of and may be used to describe one of the many different intraluminal devices which can be deployed from a delivery device. The intraluminal devices disclosed herein, e.g., tacks, can include one or more radiopaque markers. The delivery device(s) disclosed herein can comprise a plurality of delivery platforms, the delivery platforms configured for holding one or more intraluminal devices (e.g., tacks) in a compressed position on the delivery device and having a unique shape, such as a non-constant outer diameter, an hourglass shape, a tapered proximal half, ridges, dimples, etc. This unique shape can be positioned between pusher bands, e.g., annular pusher bands, which may also be radiopaque markers.

In some embodiments, the unique shape of the delivery platform(s) is provided by a sleeve of flexible material with the unique shape as part of an inner shaft (e.g., surrounding a harder inner shaft). In some embodiments, at least a portion of at least one of the pusher bands is radiopaque. Radiopaque pusher bands can be made of any of a number of materials that is at least partially radiopaque, including, for example, certain plastics, metals, wires, etc. Additionally, pusher bands may be rigid or they may be a material configured to be bendable/flexible (such as laser cut tubing), or a length or sections of material to provide bendability/flexibility to the delivery device. In some embodiments, the pusher bands are annular, e.g., completely surrounding the inner shaft. In some embodiments, the pusher bands do not completely encircle the inner shaft. For example, the pusher bands may comprise one or more elements (e.g., strips, semi-circles, etc.) positioned about or around the inner shaft to increase the distance from the central longitudinal axis of the inner shaft, e.g., the pusher band may have a larger outer diameter by comparison compared to the outer diameter of the inner shaft. As used herein, pusher bands can be annular or any other shape that is configured to satisfy one or more of the structural and/or functional requirements of the pusher bands discussed herein.

In some embodiments, the delivery device comprises a plurality of delivery platforms, each of the delivery platforms configured to hold an intraluminal device in a compressed position on the delivery device and having at least one unique material property. For example, a portion of the delivery platform may be made of a material (or coated with a material) having a different coefficient of friction than at least one other portion of the delivery platform. This material or coating can be positioned between pusher bands, which, as discussed herein, may be or contain radiopaque markers.

An intraluminal device deployment method can include alignment of radiopaque markers on the outer sheath and the intraluminal device to be deployed, e.g., a tack or a plurality of tacks, prior to deployment. As will be readily understood, the term "intraluminal device" used herein encompasses, but is not limited to, vascular tacks.

A method of marker band alignment and intraluminal device or intraluminal device delivery can be performed. The method can include: advancing a delivery device with a plurality of intraluminal devices in a compressed state to a treatment area; each intraluminal device comprising a plurality of struts and a radiopaque marker positioned in a central region of the intraluminal device, each intraluminal device being a same size with the radiopaque marker positioned in a same location; the delivery device comprising an inner core having a plurality of delivery platforms, each delivery platform having one of the plurality of intraluminal devices, and an outer sheath covering at least a portion of the inner core and delivery platforms, the outer sheath having a radiopaque marker (e.g., a radiopaque marker band) positioned at or proximally from a distal end; retracting (e.g., withdrawing) the outer sheath until the radiopaque marker on the outer sheath and radiopaque marker on a first intraluminal device to be delivered are aligned; aligning these two radiopaque markers with a treatment area—such as a tissue dissection or lesion to be treated before release of the intraluminal device; then retracting the outer sheath to release the intraluminal device.

In some embodiments, a delivery device comprises an inner shaft, a delivery platform and an outer sheath. The delivery platform can include a pair of pusher bands (e.g., annular bands) about/around the inner shaft, each of the pusher bands having an outer diameter (e.g., first outer diameter), which may or may not be the same, and a sleeve. In some embodiments, the sleeve is secured to the inner shaft and positioned between the pusher bands. In some embodiments, the sleeve extends under at least one pusher band. In some embodiments, the sleeve and the pusher band comprise one component made of one or more elements. The sleeve can have a higher coefficient of friction (e.g., can comprise a lower durometer material) than the inner shaft and optimally also a higher coefficient of friction than the pair of pusher bands. The sleeve can further have a non-constant outer diameter. For example, at least a portion of the sleeve has a diameter that is less than an outer diameter of at least one or both of the pusher bands. The delivery platform can be configured to receive an intraluminal device for deployment from the delivery device into a vessel and to receive the intraluminal device between the pusher bands and on (e.g., contacting) at least a portion of the sleeve. The outer sheath can be positioned about and movable with respect to (e.g., slidable over) at least a portion of the inner shaft and the delivery platform, the outer sheath having a pre-deployment position covering at least a portion of the delivery platform and at least one delivery position where the outer sheath is retracted (e.g., withdrawn), exposing at least one of the pusher bands and at least a portion of the sleeve of the delivery platform.

According to some embodiments, a plurality of additional delivery platforms are included for sequential delivery of a plurality of intraluminal devices. Each additional delivery platform can comprise an additional sleeve and an additional pusher band. Each of the pusher bands can have a radius on one or more of its end(s) or edges. The pusher bands can be made of, from, or using, for example, a radiopaque component (e.g., a radiopaque helical coil), e.g., a radiopaque component encased in a polymer, a radiopaque polymer (e.g., having a lower coefficient of friction (e.g., made out of a higher durometer material)) than a material, such as a polymer, that forms at least a portion of the sleeve.

The sleeve can include any number of different shapes, sizes, and/or materials, and can include surface modification or texturing, e.g., ridges, dots, dimples, coatings, multiple materials, etc.

In some embodiments, a delivery device is configured as an over-the-wire or rapid exchange style device.

In some embodiments, a delivery device comprises an inner shaft, the inner shaft having a nose cone on the distal tip; a delivery platform; and an outer sheath. The delivery platform can comprise a pair of pusher bands secured to the inner shaft, both of the pusher bands having a first outer diameter; and a sleeve secured to the inner shaft and positioned between the pusher bands. The sleeve can have a higher coefficient of friction (e.g., a lower durometer) than the inner shaft and optionally also the pair of pusher bands. The sleeve may further have a first outer diameter section (e.g., a first constant outer diameter section) and a second outer diameter section (e.g., a second constant outer diameter section). The second outer diameter section of the sleeve may have a larger outer diameter than the first outer diameter section of the sleeve, but less than the first outer diameter of the pusher bands. The second outer diameter section of the sleeve may having a shorter axial length than the first outer diameter section of the sleeve. The sleeve may have a tapered transition between the first and second outer diameter sections of the sleeve, which may be smooth. The outer diameter sections of the sleeve may be or have a constant diameter, stepped, tapered, etc. The delivery platform can be configured to receive an intraluminal device for deployment from the delivery device into a vessel and configured to receive the intraluminal device between the pusher bands and on or in contact with the sleeve. The outer sheath can be positioned about and movable with respect to (or slidable over) at least a portion of the inner shaft and the delivery platform. The outer sheath can have a pre-deployment position covering at least a portion of the delivery platform and at least one delivery position where the outer sheath is retracted exposing at least one of the pusher bands and at least a portion of the sleeve of the delivery platform.

In some embodiments, a delivery device can comprise an inner shaft, a distal pusher band, a proximal pusher band, a delivery platform, an outer sheath, and a post deployment dilation device. The distal pusher band and the proximal pusher band can be surrounding and directly or indirectly fixed to the inner shaft. The inner shaft can have a first diameter and the distal pusher band and the proximal pusher band can have a second diameter (or diameters) that is (or are) larger than the first diameter (of the inner shaft). The delivery platform can be defined by a proximal end of the distal pusher band and a distal end of the proximal pusher band. The delivery platform can be configured to receive a self-expanding intraluminal device between the distal pusher band and the proximal pusher band and around the inner shaft for deployment from the delivery device into a vessel. The outer sheath can be positioned about and movable with respect to, e.g., slidable over, at least a portion of the inner shaft and the delivery platform. The outer sheath can have a pre-deployment position, covering at least a portion of the delivery platform, and at least one delivery position, where the outer sheath is retracted exposing at least a portion of the delivery platform. In some embodiments, the delivery position of the outer sheath exposes at least one of the distal annular band and the proximal annular band. The post deployment dilation device can comprise a deployment platform and a plurality of expansion filaments. The deployment platform can be fixed with respect to the inner shaft. The plurality of expansion filaments can be radially spaced around the inner shaft. Further, each expansion filament of the plurality of expansion filaments can have a first end fixed with respect to an end of the deployment platform. The plurality of expansion filaments can have a pre-actuated position (or configuration), having a pre-deployment diameter, and an actuated position (or configuration), having a deployment diameter or deployment diameter range larger than the pre-deployment diameter. The post deployment dilation device can be configured to apply a radial force to an inner surface of the self-expanding intraluminal device after deployment of the self-expanding intraluminal device so as to improve at least one of expansion of the self-expanding intraluminal device and seating of the self-expanding intraluminal device in the vessel.

A delivery device can comprise an inner shaft, a delivery platform, an outer sheath, and a post deployment dilation device. The inner shaft can have a nose cone on the distal tip. The delivery platform can be fixed in position on the inner shaft with respect to the nose cone. Furthermore, the delivery platform can comprise a pair of pusher bands directly or indirectly fixed (e.g., secured) to the inner shaft and a middle portion. Both of the pusher bands can have a first outer diameter and the middle portion can have a second outer diameter. The second diameter can be smaller than the first outer diameter. The delivery platform can be configured to receive an intraluminal device for deployment from the delivery device into a vessel. More specifically, the delivery platform can be configured to receive the intraluminal device between the pusher bands and on the inner shaft. The outer sheath can be positioned about and movable with respect to (e.g., withdrawn, retracted, slidable over, etc.) at least a portion of the inner shaft and the delivery platform. The outer sheath can have a pre-deployment position, covering at least a portion of the delivery platform, and at least one delivery position, where the outer sheath is retracted exposing at least one of the pusher bands and at least a portion of the sleeve of the delivery platform. The post deployment dilation device can be positioned between the nose cone and the delivery platform and can comprise a plurality of expansion filaments. The expansion filaments can be configured to be radially expanded upon actuation so as to generate an outward radial force on an inner surface of the intraluminal device after release of the intraluminal device.

A delivery device can comprise an inner shaft, at least one delivery platform, an outer sheath, and a post deployment dilation device. The inner shaft can have a nose cone on its distal tip. The at least one delivery platform can be fixed in position on the inner shaft with respect to the nose cone. Furthermore, each delivery platform of the at least one delivery platform can comprise a pair of pusher bands secured to the inner shaft, and a middle portion. Both of the pusher bands can have a first outer diameter and the middle portion can have a second outer diameter. The second diameter, e.g., of the middle portion, can be smaller than the first outer diameter, e.g., of the pusher band(s). The delivery platform can be configured to receive an intraluminal device for deployment from the delivery device into a vessel. More specifically, the delivery platform can be configured to receive the intraluminal device between the pusher bands and on the inner shaft. The outer sheath can be movable with respect to and positioned about at least a portion of the inner shaft and the delivery platform. The outer sheath can have a pre-deployment position, in which it is covering at least a portion of the delivery platform, and at least one delivery position, in which the outer sheath is retracted, thereby exposing at least one of the pusher bands and at least a portion of the delivery platform (e.g., a sleeve of the delivery platform). The post deployment dilation device can be positioned about the outer sheath and can comprise a plurality of expansion filaments. The expansion filaments can be configured to be radially expanded upon actuation so as to generate an outward radial force on an inner surface of an intraluminal device after release of the intraluminal device (e.g., an intraluminal device delivered using the delivery device).

A delivery device can comprise an inner shaft, at least one delivery platform, an outer sheath, and a post deployment dilation device. The inner shaft can have a nose cone on its distal tip. The at least one delivery platform can be fixed in position on the inner shaft with respect to (e.g., relative to) the distal end of the inner shaft, e.g., the nose cone. Furthermore, each delivery platform of the at least one delivery platform can comprise a pair of pusher bands secured to the inner shaft, and a middle portion. Both of the pusher bands can have a first outer diameter and the middle portion can have a second outer diameter. The second diameter can be smaller than the first outer diameter. The at least one delivery platform can be configured to receive an intraluminal device for deployment from the delivery device into a vessel or volume, e.g., a blood vessel. More specifically, the at least one delivery platform can be configured to receive the intraluminal device between the pusher bands and on the inner shaft. The outer sheath can be positioned about and movable with respect to (e.g., withdrawn, retracted, slidable over, etc.) at least a portion of the inner shaft and the delivery platform. The outer sheath can have a pre-deployment position, covering at least a portion of a distal-most delivery platform of the at least one delivery platform, and at least one delivery position, where the outer sheath is retracted exposing at least one of the pusher bands and at least a portion of the distal-most delivery platform of the at least one delivery platform, e.g., of the sleeve of the delivery platform. The post deployment dilation device can be positioned between the nose cone and the delivery platform and can comprise a balloon or inflatable member. The balloon or inflatable member can be configured to be activated, e.g., inflated, so as to generate an outward radial force on an inner surface of the intraluminal device after release of the intraluminal device.

A delivery device can comprise an inner shaft, a delivery platform (e.g., at least one delivery platform), an outer sheath, and a post deployment dilation device. The inner shaft can have a nose cone on or at its distal tip. The delivery platform can be fixed in position on the inner shaft with respect to the distal end of the inner shaft, e.g., the nose cone. Furthermore, the delivery platform can comprise a pair of pusher bands secured to the inner shaft and a middle portion disposed between the pair of pusher bands. Both of the pusher bands can have a first outer diameter and the middle portion can have a second outer diameter. The second diameter can be smaller than the first outer diameter. The delivery platform can be configured to receive an intraluminal device for deployment from the delivery device into a vessel. More specifically, the delivery platform can be configured to receive the intraluminal device between the pusher bands and on or about the inner shaft. The outer sheath can be positioned about and movable with respect to (e.g., slidable over) at least a portion of the inner shaft and the delivery platform. The outer sheath can have a pre-deployment position, covering at least a portion of the delivery platform, and at least one delivery position, in which the outer sheath is retracted to expose at least a portion of the delivery platform (e.g., the sleeve of the delivery platform). The post deployment dilation device can be positioned about or around the outer sheath and can comprise a balloon or inflatable member. The balloon or inflatable member can be configured to be activated or actuated, e.g., inflated, so as to generate an outward radial force on an inner surface of the intraluminal device after release of the intraluminal device.

In some embodiments, the delivery device may incorporate an integrated or attachable or detachable deployment mechanism (e.g., a handle). The deployment mechanism can allow a user the ability to deploy one intraluminal device at a time. The deployment mechanism can enable the outer sheath to be moved (e.g., withdrawn, retracted, etc.) with respect to at least one delivery platform(s). The movement of the outer sheath can be a predetermined distance, for example, to prepare an intraluminal device for delivery or sufficient to deploy a set number of intraluminal devices, e.g., one intraluminal device, two intraluminal devices, three intraluminal device, or more intraluminal devices. The movement of the outer sheath can be continuous, such as a screw or linear motion. The deployment mechanism can have an actuator that is moved (e.g., rotated, translated, etc.)

by the user which causes the outer sheath to be moved. The deployment mechanism can have fluid ports through which fluid is delivered. The fluid can be used to maintain fluid between the inner shaft and the outer sheath. The fluid can be used to inflate a post deployment dilation device such as a balloon or inflatable member.

An intraluminal device deployment method can include one or more of the following steps. Advancing a delivery device with a plurality of intraluminal devices in a compressed state to a treatment area. Each of the plurality of intraluminal devices can comprise a plurality of struts and a radiopaque marker positioned in a central region of the intraluminal device. Each of the plurality of intraluminal devices can be a same size with the radiopaque marker positioned in a same location. The delivery device can comprise an inner shaft having a plurality of delivery platforms, each intraluminal device of the plurality of intraluminal devices positioned at a respective delivery platform of the plurality of delivery platforms, and an outer sheath covering at least a portion of the inner shaft and the plurality of delivery platforms, the outer sheath having a radiopaque marker band positioned proximally at or from a distal end of the outer sheath. Retracting the outer sheath until the radiopaque marker band on the outer sheath and radiopaque marker on a first intraluminal device to be delivered of the plurality of intraluminal devices are aligned. Aligning the aligned radiopaque marker band and the radiopaque marker with the treatment area before release of the first intraluminal device. Retracting the outer sheath to release the first intraluminal device. Retracting the outer sheath until the radiopaque marker band on the outer sheath and radiopaque marker on a second intraluminal device to be delivered of the plurality of intraluminal devices are aligned.

In some embodiments of the method, aligning the aligned radiopaque marker band and the radiopaque marker with the treatment area can comprise centering the aligned radiopaque marker band and the radiopaque marker at a tissue dissection before release of the first intraluminal device. In some embodiments of the method, retracting the outer sheath until the radiopaque marker band on the outer sheath and radiopaque marker on the first intraluminal device to be delivered of the plurality of intraluminal devices are aligned can comprise retracting the outer sheath until a distal-most end of the outer sheath and a distal-most end of the first intraluminal device are aligned. In some embodiments of the method, retracting the outer sheath until the radiopaque marker band on the outer sheath and radiopaque marker on the first intraluminal device to be delivered of the plurality of intraluminal devices are aligned can comprise retracting the outer sheath until the radiopaque marker band is positioned at a middle of the first intraluminal device. In some embodiments of the method, the first intraluminal device can have a single column of radiopaque markers and retracting the outer sheath until the radiopaque marker band on the outer sheath and radiopaque marker on the first intraluminal device to be delivered of the plurality of intraluminal devices are aligned can comprise retracting the outer sheath until the radiopaque marker band encircles the single column of radiopaque markers.

An intraluminal device deployment method can comprise advancing a delivery device with an intraluminal device in a compressed state to a target volume. The delivery device can comprise an inner shaft, a delivery platform, an outer sheath, and a post deployment dilation device. The inner shaft can have a first diameter. The delivery platform can have a distal and a proximal pusher band each having a second diameter larger than the first diameter (of the inner shaft). The delivery platform can be configured to receive the intraluminal device between the pusher bands and around the inner shaft for deployment from the delivery device into a volume. The outer sheath can be positioned about and movable with respect to (e.g., slidable over) at least a portion of the inner shaft and the delivery platform. The outer sheath can have a pre-deployment position, in which the outer sheath covers at least a portion of the delivery platform, and a deployment position, in which the outer sheath exposes at least a portion of the delivery platform. The post deployment dilation device can comprise a plurality of expansion filaments configured to be radially expanded upon activation of the post deployment dilation device so as to generate an outward radial force on an inner surface of the intraluminal device after release and expansion of the intraluminal device. The intraluminal device deployment method can further comprise: retracting the outer sheath to release the intraluminal device; expanding the intraluminal device; moving the delivery device so as to position at least a portion of the post deployment dilation device within the expanded intraluminal device; and activating the post deployment dilation device to cause at least a portion of the post deployment dilation device to radially expand and to generate an outward radial force on an inner surface of the expanded intraluminal device. The expanding step can comprise one of allowing the intraluminal device to expand and actively expanding at least a portion of the intraluminal device.

An intraluminal device deployment method can comprise advancing a delivery device with (e.g., containing, loaded with, etc.) an intraluminal device, e.g., in a compressed state, to a target volume. The delivery device can comprise an inner shaft, a delivery platform, an outer sheath, and a post deployment dilation device. The inner shaft can have a first diameter. The delivery platform can have a distal and a proximal pusher band each having a second diameter larger than the first diameter (of the inner shaft). The delivery platform can be configured to receive the intraluminal device between the pusher bands and around the inner shaft for deployment from the delivery device into a volume. The outer sheath can be positioned about and movable with respect to (e.g., slidable over) at least a portion of the inner shaft and the delivery platform. The outer sheath can have a pre-deployment position, in which the outer sheath covers at least a portion of the delivery platform, and a deployment position, in which the outer sheath exposes at least a portion of the delivery platform. The post deployment dilation device can comprise a balloon or inflatable member. The balloon or inflatable member can be configured to be radially expanded upon activation, e.g., inflated, so as to generate an outward radial force on an inner surface of the intraluminal device after release of the intraluminal device. The intraluminal device deployment method can further comprise: retracting or withdrawing the outer sheath to release the intraluminal device; expanding the intraluminal device (or allowing the intraluminal device to expand); moving the delivery device so as to position at least a portion of the post deployment dilation device within the expanded intraluminal device; and activating the post deployment dilation device to cause at least a portion of the post deployment dilation device to radially expand and to generate an outward radial force on an inner surface of the expanded intraluminal device. The expanding step can comprise one of allowing the intraluminal device to expand and actively expanding at least a portion of the intraluminal device.

In some embodiments of the method, one or more (e.g., two, three, four, five, etc.) intraluminal devices may be deployed followed by moving the delivery device so as to position at least a portion of the post deployment dilation device within an expanded intraluminal device; and activating the post deployment dilation device to cause at least a portion of the post deployment dilation device to radially expand and to generate an outward radial force on an inner surface of an expanded intraluminal device.

An intraluminal device deployment method can include one or more of the following steps. Advancing a delivery device with a plurality of intraluminal devices in a compressed state to a treatment area or target volume. Each of the plurality of intraluminal devices can comprise a plurality of struts and at least one radiopaque marker positioned in a central region of the intraluminal device. Each of the plurality of intraluminal devices can be the same size (e.g., approximately the same size) with the at least one radiopaque marker positioned in the same location (e.g., approximately the same location). The delivery device can comprise an inner shaft having a plurality of delivery platforms, each intraluminal device of the plurality of intraluminal devices positioned on, at, or within a respective delivery platform of the plurality of delivery platforms, and an outer sheath covering at least a portion of the inner shaft and the plurality of delivery platforms, the outer sheath having a radiopaque marker band positioned proximally at or from a distal end (e.g., a distal-most end) of the outer sheath. The delivery device can comprise a deployment mechanism. The deployment mechanism can contain an actuator. Aligning the intraluminal device radiopaque marker of the first intraluminal device with the treatment area before release of the first intraluminal device. Using the deployment mechanism to retract the outer sheath to release the first intraluminal device. If desired, using the deployment mechanism to deploy one or more additional intraluminal devices. In some embodiments of the method, a post deployment dilation device can be used, as previously described, to generate an outward radial force on an inner surface of the intraluminal device after release of the intraluminal device. The post deployment dilation may be conducted after the release of one or the release of more than one intraluminal device.

An intraluminal device deployment method can include one or more of the following steps. Advancing a delivery device with a plurality of intraluminal devices, e.g., in a compressed state, to a treatment area. Each of the plurality of intraluminal devices can comprise a plurality of struts and at least one radiopaque marker positioned in a central region of the intraluminal device. Each of the plurality of intraluminal devices can be the same size (e.g., approximately the same size) with the at least one radiopaque marker positioned in the same location (e.g., approximately the same location). The delivery device can comprise an inner shaft having a plurality of delivery platforms, each intraluminal device of the plurality of intraluminal devices positioned at a respective delivery platform of the plurality of delivery platforms, and an outer sheath covering at least a portion of the inner shaft and the plurality of delivery platforms, the outer sheath having a radiopaque marker band positioned proximally at or from a distal end (e.g., a distal-most end) of the outer sheath. The delivery device can comprise a deployment mechanism. The deployment mechanism can contain an actuator. Using the deployment mechanism to retract the outer sheath until the radiopaque marker band on the outer sheath and at least one radiopaque marker on a first intraluminal device to be delivered of the plurality of intraluminal devices are aligned. Aligning the aligned radiopaque marker band and the at least one radiopaque marker with the treatment area before release of the first intraluminal device. Using the deployment mechanism to retract the outer sheath to release the first intraluminal device (e.g., the distalmost intraluminal device) of the plurality of intraluminal devices. Optionally, using the deployment mechanism as previously described to deploy additional intraluminal devices. In some embodiments of the method, a post deployment dilation device can be used as previously described to generate an outward radial force on an inner surface of the intraluminal device after release of the intraluminal device. The post deployment dilation may be conducted after the release of one or the release of more than one of the plurality of intraluminal devices.

BRIEF DESCRIPTION OF THE DRAWINGS

Various embodiments are depicted in the accompanying drawings for illustrative purposes, and should in no way be interpreted as limiting the scope of the inventions, in which like reference characters denote corresponding features consistently throughout similar embodiments.

FIG. 1A is a side view of a delivery device that has been shortened to facilitate illustration.

FIG. 2 shows a view of the distal region of the delivery device with an outer sheath retracted.

FIGS. 7A-7C illustrate certain steps of a deployment method.

FIGS. 8A-8C are various views of a distal region of a delivery device with a post deployment dilation device comprising a plurality of expansion filaments.

FIGS. 8D-8G show steps in a method for using a post deployment dilation device comprising a plurality of expansion filaments.

FIGS. 9A-9B show cross sections of various inner shafts adapted to receive a plurality of expansion filaments.

FIGS. 10A-10C are various views of a distal region of a delivery device with a post deployment dilation device comprising a sliding sleeve and a plurality of expansion filaments.

FIGS. 10D-10F show steps in a method for using a post deployment dilation device comprising a sliding sleeve and a plurality of expansion filaments.

FIGS. 11A-11C are various views of a distal region of a delivery device with a post deployment dilation device comprising a sliding sleeve and a bellow.

FIGS. 11D-11F show steps in a method for using a post deployment dilation device comprising a sliding sleeve and a bellow.

FIGS. 12A-12C are various views of a distal region of a delivery device with a post deployment dilation device comprising an inner core balloon.

FIGS. 12D-12F show steps in a method for using a post deployment dilation device comprising an inner core balloon.

FIG. 16A is an enlarged view of a shaft region of the delivery device of FIG. 15.

FIGS. 16B-16C show cross sections of shaft regions of FIG. 16A.

FIG. 16D is an alternative cross section of a shaft region of FIG. 16A.

FIG. 17 is a side view of a delivery device that has been shortened to facilitate illustration, with a post deployment dilation device comprising an outer sheath balloon.

FIG. 18 shows a view of the distal region of the delivery device with a post deployment dilation device comprising an outer sheath balloon.

FIG. 19 is a side view of a delivery device that has been shortened to facilitate illustration, with a post deployment dilation device comprising an outer sheath balloon with a rapid exchange style configuration.

FIG. 20 shows a view of the distal region of the delivery device with a post deployment dilation device comprising an outer sheath balloon with a rapid exchange style configuration.

FIGS. 21A-21B show cross sectional views of an intraluminal device deployment mechanism.

FIGS. 22A-22B show sectional views of an alternative release engagement.

DETAILED DESCRIPTION

The following description of the preferred embodiments of the invention is not intended to limit the invention to these preferred embodiments, but rather to enable any person skilled in the art to make and use this invention.

A delivery device 10 can be used as part of a procedure in which it is or may be desirable to deploy one or more intraluminal devices 2, including those procedures which treat atherosclerotic occlusive and vascular disease. The delivery device 10 can be used to deliver one or more intraluminal devices 2 to a site, volume, target, or area, such as an area of plaque accumulation or a dissection. The intraluminal devices 2 can stabilize the site and/or hold pieces of plaque out of the way of blood flow. It will be understood that though the delivery devices and methods described herein are described primarily with reference to vascular procedures, they can also be used in treatments for other parts of the body.

FIGS. 1 and 2 illustrate an embodiment of delivery device 10 that can be used for sequential delivery of multiple intraluminal devices 2. The delivery device 10 can be used in procedures to treat atherosclerotic occlusive disease, though it is not limited to these procedures.

Figure 1B:
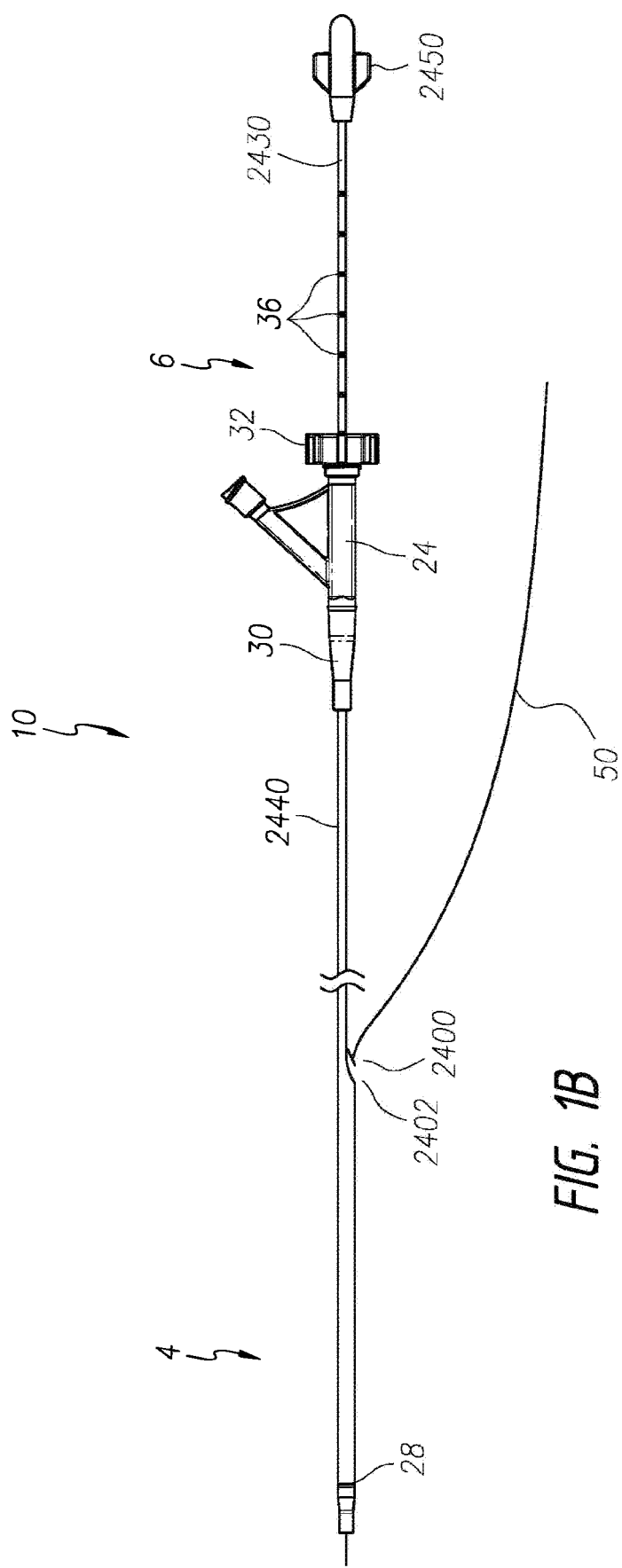
FIG. 1B is a side view of a rapid exchange style delivery device that has been shortened to facilitate illustration.

In another embodiment, the delivery device 10, which can be used for delivery, e.g., sequential delivery, of multiple intraluminal devices 2, may be of a rapid exchange style, e.g., only a portion of the delivery catheter of the delivery device 10 rides on or over the guidewire 50. A shortened version of an embodiment of a rapid exchange style delivery catheter 10 is shown in FIG. 1B. The rapid exchange style delivery catheter 10 can have apertures or ports such as a rapid exchange inner shaft guidewire port 2400 and/or a rapid exchange outer sheath guidewire port 2402 that allow the guidewire 50 to exit the inner shaft 26 (see, e.g., FIG. 4) at a point distal to the proximal outer sheath housing 24. The rapid exchange proximal inner shaft 2430 may be attached to the rapid exchange proximal inner shaft hub 2450. The portion of the delivery device 10 distal to the rapid exchange guidewire port 2400 may be similar to that shown in and described in connection with FIG. 2.

The delivery device 10 of FIG. 1, which has been shortened to facilitate illustration, highlights the distal region 4, e.g., including the distal end, and proximal region 6, e.g., including the proximal end. The proximal region 6 is relatively towards the user, e.g., a physician or other medical professional, while the distal region 4 is relatively away from the user, e.g., towards the patient. Distal and proximal can be relative to the feature being discussed, e.g., if discussing a post deployment dilation device such as a balloon, the balloon itself has distal and proximal aspects while the entire balloon can be located in the distal region of the delivery catheter. In some embodiments, the proximal end or region 6 of the delivery device can be held by a user during a medical procedure. Furthermore, the proximal end or region 6 of the delivery device may be used to control delivery of one or more intraluminal devices 2. FIG. 2 shows the distal region 4 with six (6) intraluminal devices 2, each positioned at a dedicated delivery platform 8. Comparing FIGS. 1 and 2, it can be seen that an outer sheath 12 has been retracted, e.g., withdrawn, from a more distal position in FIG. 2. This reveals the delivery platforms 8 and the respective intraluminal devices 2. The intraluminal devices 2 are preferably self-expandable and are shown in their compressed position to represent how they would fit in the delivery platforms 8. In typical use, the outer sheath 12 would be covering the intraluminal devices 2 when in this position. As will be discussed in more detail below, the outer sheath 12 can be retracted in a systematic manner to deploy one intraluminal device 2 at a time at a desired treatment location.

Figures 3, 3A:
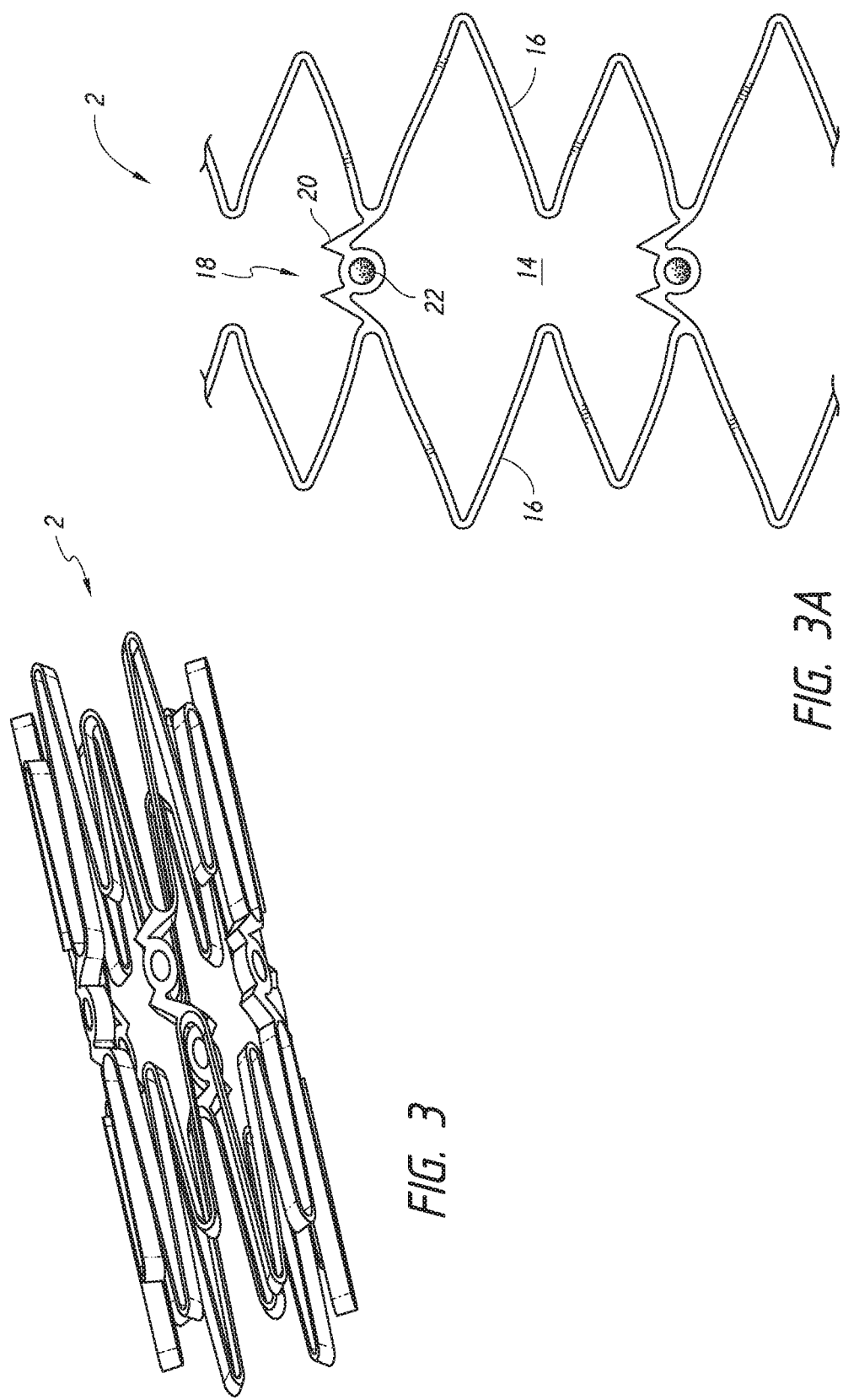
FIG. 3 shows an embodiment of an intraluminal device.
FIG. 3A shows a flattened section of the intraluminal device of FIG. 3.

Relatively small intraluminal devices 2, for example with only one (FIGS. 3 & 3A) or two columns of cells 14, can be delivered at precise sites or treatment locations. In some embodiments, the intraluminal devices 2 may be delivered and spaced appropriately and intentionally to not overlap. FIG. 3A shows a flattened section of the intraluminal device 2 of FIG. 3. It can be seen that a single column of cells 14 are formed by two concentric rings of undulating struts 16 connected by bridge members 18. The bridge members 18 have a pair of anchors 20 and a radiopaque marker 22. The intraluminal device 2 can also be comprised of two or more cells 14, or alternatively by other structures known in the art. Multiple small intraluminal devices 2 can be used to treat a single or multiple sites, e.g., lesions. This can minimize the amount of foreign material in the body, while providing needed holding forces. Various embodiments of intraluminal devices 2 and delivery devices 10 are described in more detail in Applicants' related patent application Ser. No.

13/179,458 filed Jul. 8, 2011, published as US 2012/0035705 and patent application. Ser. No. 13/749,643 filed Jan. 24, 2013, published as US 2013/0144375, both of which are incorporated by reference herein and made a part of this specification.

It will be understood, that the delivery devices 10 and methods can also be used for other intraluminal devices 2, including larger devices, and are not limited to use with intraluminal devices 2 having only one or two columns of cells 14.

Returning now to FIG. 1, the proximal region 6 of the illustrated embodiment will now be described. The delivery device 10 can include an outer sheath 12, a proximal outer sheath housing 24, and an inner shaft 26. The outer sheath 12 can be constructed as a laminate of polymer tubing(s) and may have braided wires embedded in the polymer tube(s). The polymer tubes can be formed by an extrusion process or other process(es). Flexibility and stiffness of the outer sheath can be controlled by altering or controlling one or more variables, including, but not limited to, the number of braid wires, the braid pattern and pitch of the braid, the type of polymer(s) used, and the various thicknesses and properties of the materials used. In other embodiments, the outer sheath 12 can be formed of or using a hypotube, such as a metal or plastic hypotube. Flexibility and stiffness of the outer sheath 12 can be controlled by many features such as the slope and frequency of a spiral cut along the length of the hypotube. The outer sheath 12 may also include an outer sheath radiopaque marker 28 at or near the distal end. In some embodiments, the outer sheath radiopaque marker 28 can be an annular band spaced from the distal-most end.

As shown, the outer sheath 12 is a braided shaft and the proximal outer sheath housing 24 may be a bifurcation luer that connects to the outer sheath 12 through an outer sheath strain relief 30. The outer sheath strain relief 30 can take any form, such as being made of polyolefin or other polymer material.

The proximal outer sheath housing 24, e.g., bifurcation luer, may have a main arm to receive the inner shaft 26 and a side arm. The proximal outer sheath housing 24 can be located relative to or disposed in the proximal region of the outer sheath 12. The side arm of the proximal outer sheath housing 24 may include a flush port 25 that may be used to introduce fluid(s) to flush out air and increase lubricity in the space between the outer sheath 12 and the inner shaft 26.

A hemostatic valve 32, which can be a tuohy borst adapter or other sealing arrangement, can be provided proximal of or integrated into the proximal outer sheath housing 24 to receive and seal the space between the inner shaft 26 and the outer sheath 12. The hemostatic valve 32 can also provide a locking interface, such as a screw lock, to secure the relationship between the outer sheath 12 and the inner shaft 26. This can allow the user to properly place the delivery device 10 within a patient without prematurely deploying an intraluminal device 2.

The inner shaft 26 is shown with a proximal inner shaft housing 34 and deployment reference marks 36. The deployment reference marks 36 can correspond with the delivery platforms 8, such that the spacing between each deployment reference mark 36 can be the same as the spacing between features of the delivery platforms 8. For example, the space between deployment reference marks 36 can be the same as the distance between the centers of the delivery platforms 8.

In some embodiments, a distal-most deployment reference mark 36, or a mark that is different from the others, such as having a wider band, or different color, can indicate a primary or home position. For example a deployment reference mark 36 with a wider band than the others can be aligned with the proximal end of the proximal outer sheath housing 24 or hemostatic valve 32. This can indicate to a user that the outer sheath 12 is in a position completely covering the inner shaft 26 proximal of the nose cone 38. In some embodiments, this alignment can also translate to alignment of the outer sheath radiopaque marker 28 on the outer sheath 12 to a radiopaque marker in the distal region of the inner shaft 26.

In some embodiments, one or more of the deployment reference marks 36 can represent the number of intraluminal devices 2 that are within the system. Thus, once an intraluminal device 2 is released, the deployment reference mark 36 will be covered up and the user can know that the remaining deployment reference marks 36 correspond with the remaining number of intraluminal devices 2 available for use. In such an embodiment, the proximal end of the proximal outer sheath housing 24 or hemostatic valve 32 can be advanced to be centered approximately between two deployment reference marks 36 to indicate deployment. The proximal outer sheath housing 24 or hemostatic valve 32 may also have an indicator (not shown) to or against which a deployment reference mark 36 can be aligned. In some embodiments, one or more of the deployment reference marks 36 can be numbered, e.g., numbers corresponding to the number of intraluminal devices 2 remaining in the deployment device, ready to be deployed, or the number of intraluminal devices 2 that have already been delivered. It will also be understood that the delivery device 10 could have a deployment mechanism, such as a handle or trigger assembly either separate or integrated into the delivery device 10 such as those described herein and in U.S. Provisional Appl. No. 62/109,550, filed Jan. 29, 2015, and U.S. Pat. No. 9,192,500, both of which are incorporated by reference herein and are to be considered a part of this specification.

Figure 4:
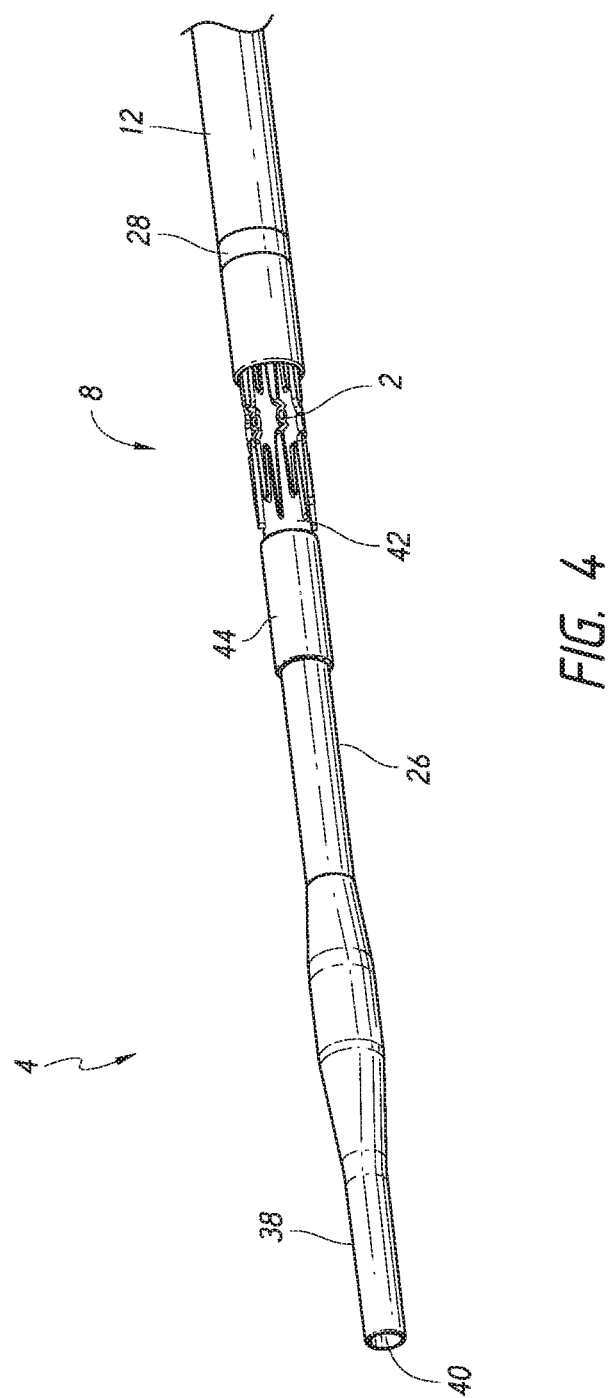
FIG. 4 illustrates a detail view of the distal region of the delivery device with the outer sheath partially retracted.

Looking now to FIG. 4, a detail view of a portion of the distal region 4 of the delivery device 10 is shown. Features of the illustrated embodiment include the inner shaft 26 with a distal soft tip. The tip can be a tapered nose cone 38. The nose cone 38 can serve as a dilating structure to atraumatically displace tissue and help to guide the delivery device 10 through the vasculature. The nose cone 38, itself, may be partially or entirely radiopaque, and/or a radiopaque element can be incorporated into or near the tip. The nose cone 38 may be formed from a distal portion of an inner core balloon 2110, which may incorporate an inner core balloon 2110 distal seal. A guidewire lumen 40 can be seen that extends through the inner shaft 26 to the proximal inner shaft housing 34 (FIG. 1). The guidewire lumen 40 is configured for receipt and advancement of a guidewire 50 therein.

Parts of a delivery platform 8 are also shown. The delivery platforms 8 are identical in the illustrated embodiment, though other embodiments can have different sizes and constructions between different delivery platforms 8. A crimped or compressed intraluminal device 2 is shown in the delivery platform 8.

Figure 5:
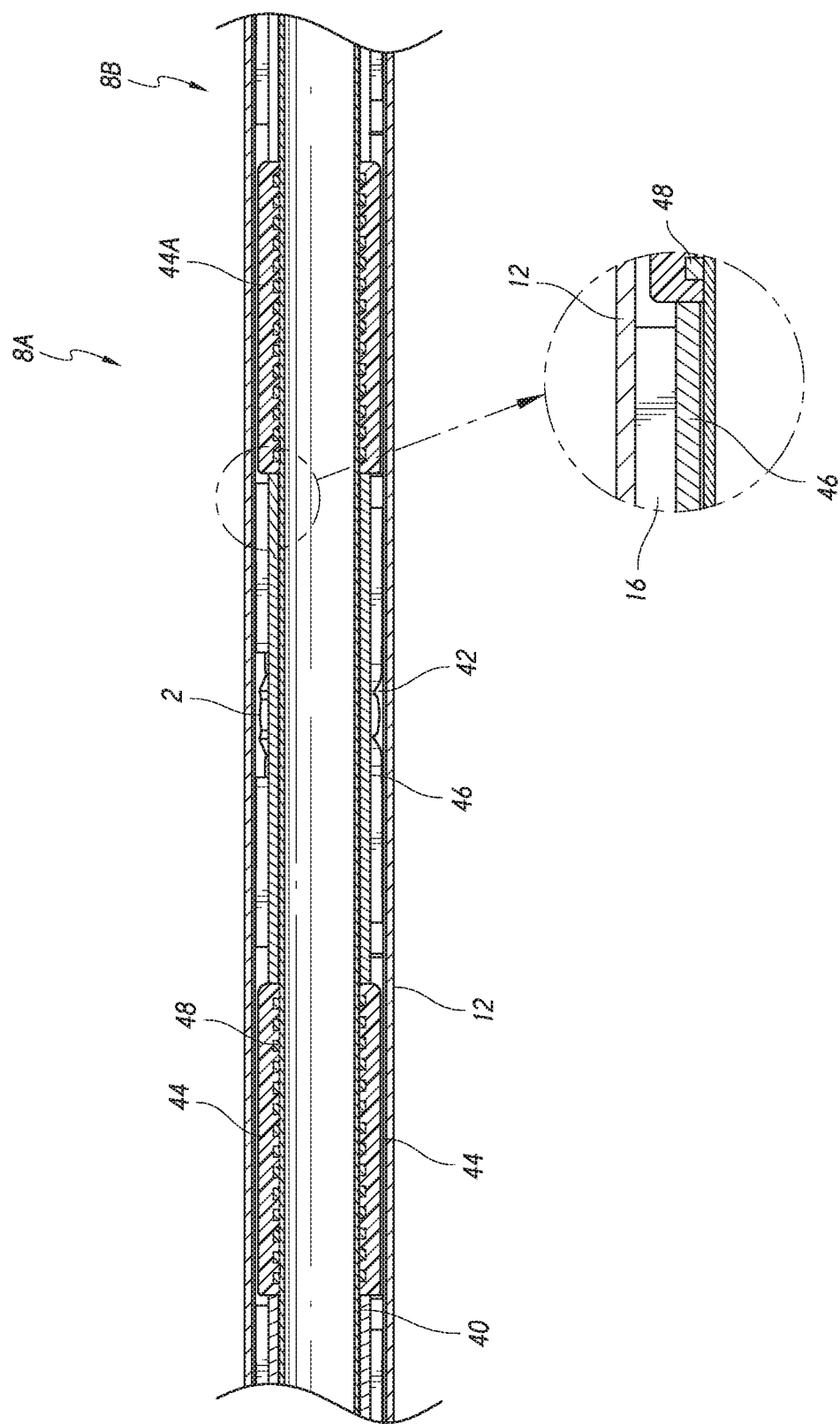
FIG. 5 is a cross section of a delivery device showing an embodiment of delivery platform.

As can be seen in FIGS. 2 and 4, one or more delivery platforms 8 can be disposed on the inner shaft 26 adjacent the distal region 4 of the delivery device 10. Each of the delivery platforms 8 can comprise a recess 42 positioned or extending between a pair of pusher bands 44. These pusher bands 44 may be annular, only extend a portion of the way around the inner shaft 26, or simply be one or more areas of increased diameter on the inner shaft 26. FIG. 5 shows a cross section of a delivery device at one embodiment of delivery platform 8A. In the illustrated embodiment, the proximal pusher band 44A of a first delivery platform 8A is also the distal pusher band 44A of a second delivery platform 8B located immediately proximal (only partially shown). The pusher band 44 has a larger outer diameter as compared to the delivery platforms 8A and 8B at the recess 42. In some embodiments, the recess 42 can be defined as the smaller diameter region next to, or between, one or two pusher bands 44 and/or an additional feature on the inner shaft 26.

One or more of the pusher bands 44 can be at least partially radiopaque. For example, proximal and distal radiopaque pusher bands 44 can be provided to make the ends of the delivery platform 8 visible using standard visualization techniques. The radiopaque pusher bands 44 can take any suitable form, for example including one more of tungsten, tantalum, iridium, platinum, palladium, rhenium, gold, $Bi_2O_3$, and $BaSO_4$. In some embodiments, the pusher bands 44 can be about 4 mm long with recesses about 6.75 mm between them. An intraluminal device 2 of about 6.5 mm can be positioned between the pusher bands 44. In some embodiments, the pusher bands 44 can be between 50-70% of the size of the recess 42 and/or the intraluminal device 2. In some embodiments, the pusher bands 44 are about 60%. In other embodiments, the pusher bands 44 can be much smaller, at between 10-20% of the size of the recess 42 and/or the intraluminal device 2. This may be the case especially with longer intraluminal devices 2. In some embodiments, at least the proximal ends of the pusher bands 44 can have a radius to help reduce potential for catching on deployed intraluminal devices 2 during movement, e.g., retraction, of the delivery device 10.

Reducing the difference in length between the recess 42 and the intraluminal device 2 can increase the precision of placement of the intraluminal device 2, especially with intraluminal devices 2 having only one or two columns of cells 14. In some embodiments, the recess 42 can be less than 1, 0.5, 0.4, 0.3, 0.25, or 0.2 mm longer than the intraluminal device 2. The intraluminal device 2 can be any number of different sizes, such as 4, 5, 6, 6.5, 8, 10, or 12 mm in length.

The outer sheath 12 can be made of polyether block amide (PEBA), a thermoplastic elastomer (TPE) available under the trade name PEBAX. In some embodiments, the outer sheath 12 can have a thinner inner liner made of a fluorinated polymer, such as, but not limited to, polytetrafluoroethylene (PTFE), which is also known as TEFLON. In some embodiments, the outer sheath 12 can incorporate a braid or coil. Any outer sheath radiopaque marker band(s) 28 or other radiopaque material may be positioned on top of, between, underneath, or incorporated into or embedded within the material or materials or layers of the outer sheath 12. In some embodiments, the outer sheath 12 has 1 outer sheath radiopaque marker band. In some embodiments, the outer sheath 12 has more than one outer sheath radiopaque marker band, for example 2 outer sheath radiopaque marker bands, 3 outer sheath radiopaque marker bands, 4 outer sheath radiopaque marker bands, 5 outer sheath radiopaque marker bands, or more than 5 outer sheath radiopaque marker bands. The outer sheath radiopaque marker band(s) 28 can range from 0.5 mm to 5 mm wide and be located from 0.5 mm to 10 mm proximal from the distal-most end 52. In some embodiments, the outer sheath radiopaque marker band(s) 28 can be 1 mm wide and 3 mm proximal from the distal-most end 52.

In the cross section of FIG. 5 it can be seen that a sleeve 46 is positioned around the inner shaft 26 between the two pusher bands 44. In some embodiments, a delivery platform 8 can comprise a sleeve 46 surrounding an inner shaft 26, where the sleeve 46 is made of a different material, or has different material properties, than the inner shaft 26. In some embodiments, the sleeve 46 provides a material having a tackiness, a grip, a tread pattern, and/or other features to help the intraluminal device 2 stay in place in the delivery platform 8. In some embodiments, the sleeve 46 can be made of PEBA. The inner shaft 26 according to some embodiments is a composite tube made of a PTFE/polyimide composite. The sleeve 46 can have a higher coefficient of friction (e.g., have a lower durometer or be softer) than the inner shaft 26 and/or the pusher bands 44. This may be the case even if made of similar types of materials. In some embodiments, the sleeve can be a material having a tackiness, a grip, a tread pattern, and/or other features to help the intraluminal device 2 stay in place (e.g., longitudinal position with respect to the inner shaft 26) while the outer sleeve 12 is retracted. This can increase the amount of control during deployment and reduce the likelihood that the intraluminal device 2 will shoot out distally from the delivery platform 8 (known in the industry as watermelon seeding). In some cases the outer sheath 12 can be partially removed thereby partially exposing an intraluminal device 2 whereby the intraluminal device 2 can partially expand while being securely retained by the delivery device 10 prior to full release.

The sleeve 46 can be sized so that with the intraluminal device 2 in the delivery platform 8 there is minimal to no space between the intraluminal device 2 and the outer sheath 12. In some embodiments, the sleeve 46 can be co-molded with or extruded onto the inner shaft 26. In some embodiments, the delivery device 10 can be formed with a single sleeve 46 extending over a length of the inner shaft 26. For example, the sleeve 46 can extend from the first delivery platform 8 to the last delivery platform 8. The pusher bands 44 may surround distinct sections of sleeve 46, or they may be encased by the sleeve 46. In some embodiments, the sleeve(s) 46 and the pusher band(s) 44 may be formed as a single unit. In some embodiments, each delivery platform 8 has a separate sleeve 46 positioned in the recess 42. The pusher bands 44 may be coated, may be encased by a different material, or may not be encased at all.

Figure 6A:
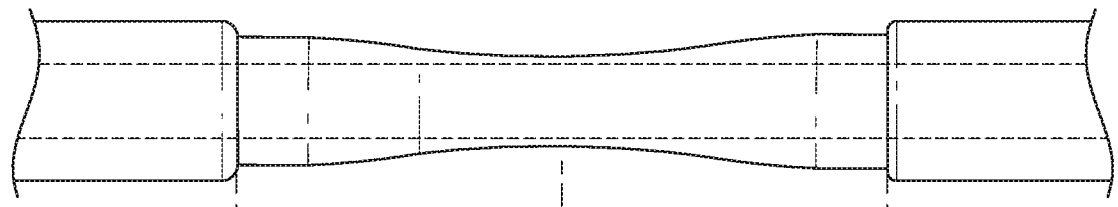
FIGS. 6A-6E illustrate various embodiments of delivery platforms having different shapes.
Figure 6B:
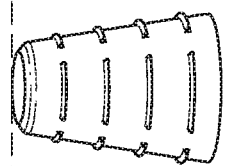
Figure 6C:
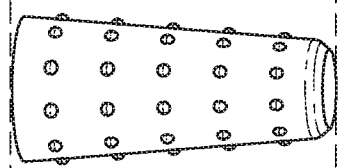
Figure 6D:
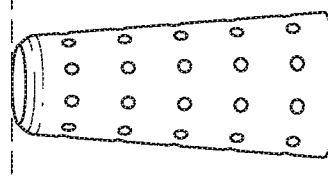

As will be understood from FIG. 5, the sleeve 46 can be cylindrical with a circular cross-section that is maintained across a portion of or the entire length of sleeve. In other embodiments, the sleeve 46 has a unique shape and may include one or more of the following: tapering (FIGS. 6A-6E), an hourglass shape (FIG. 6A), ridges (FIG. 6B), dimples (FIG. 6C), dots (FIG. 6D), two or more different diameters (FIG. 6E), etc. Features such as ridges, dots, and dimples can be positioned in any number of different patterns or groupings. In addition, the sleeve 46 (FIGS. 6B-6D), or a section of the sleeve 46 (FIG. 6E) can extend along less than the entire recess 42. In some embodiments, the length of the sleeve 46 or larger outer diameter section can correspond to the length of the intraluminal device 2. For example, the sleeve 46 or larger diameter section can extend ¾, ⅔, ½, ⅖, ⅓, ¼ of the recess and/or intraluminal device 2. The sleeve 46 or larger diameter section can extend across about 90%, about 80%, about 70%, about 60%, about 50%, about 40%, about 30%, about 20% of the recess and/or intraluminal device 2. The sleeve 46 may extend proximally across the recess 42, from the distal pusher band 44 (the sleeve 46 may or may not reach the proximal pusher band 44). The sleeve 46 may extend distally across the recess 42, from the proximal pusher band 44 (the sleeve may or may not reach the distal pusher band 44). The sleeve 46 may extend from the middle of the recess 42, equally or unevenly toward one or both of the proximal and distal pusher bands 44 (the sleeve 46 may or may not reach one or both of the proximal and distal pusher bands 44). Further, the length of the sleeve 46 or larger outer diameter section can be related to the size of the struts 16 of the undulating ring(s), such as a proximal most undulating ring. For example, it can extend along the entire, ⅘, ¾, ⅔, or ½ of the length of a strut or the length of the proximal most undulating ring. A short sleeve 46, or a larger outer diameter section of a sleeve 46, preferably extends from the proximal end of the recess 42 distally, as shown in FIGS. 6D-6E, but can also be centered in the recess 42, positioned about or at the distal end of the recess 42, as shown in FIG. 6C, or at other positions within the recess 42.

Figure 6E:
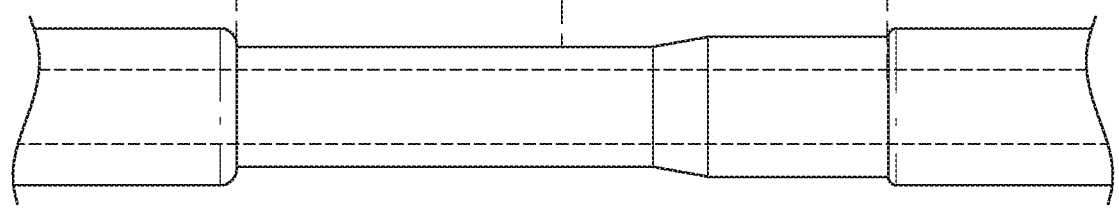

The sleeve 46 of FIG. 6E is shown having two different constant outer diameter sections with a short taper between them. The sleeve 46 can be formed from two separate sections that are thermally bonded together. The tapered portion can also be created by thermal processing (e.g., bonding) so that there is a smooth transition between the two constant outer diameter sections. As has been mentioned, the larger constant outer diameter section preferably extends from the proximal end of the recess 42 distally. This larger outer diameter section that may or may not have a constant outer diameter can extend along less than the entire recess 42 as discussed herein.

In some embodiments, an inner shaft 26 can have a higher coefficient of friction (or lower durometer) sleeve 46 between pusher bands 44. An intraluminal device 2 can be crimped onto the sleeve 46 and an outer sheath 12 can constrain the crimped intraluminal device 2 in place. The clearance between the sleeve 46 and the outer sheath 12 can result in a slight interference fit between the crimped intraluminal device 2 and the inner and outer elements. This slight interference allows the delivery system 10 to constrain the crimped intraluminal device 2 during deployment until it is almost completely unsheathed allowing the distal portion of the intraluminal device 2 to "flower petal" open and engage the vessel wall, reducing the potential for unwanted movement of an intraluminal device 2 during delivery or deployment (e.g., jumping or watermelon seeding).

According to some embodiments, the inner shaft 26 can be made of a polyimide-PEBA combination and the higher coefficient of friction (or lower durometer) PEBA sleeve 46 can be thermally bonded in between pusher bands 44. An intraluminal device 2 can be crimped onto the sleeve 46 and a PTFE lined outer sheath 12 can constrain the crimped intraluminal device 2 in place.

Returning to FIG. 5, a feature of certain embodiments of pusher band 44 is shown. In some embodiments, the pusher bands 44 are radiopaque. For example, the pusher bands 44 may be or incorporate one or more metallic materials. As discussed herein, the sleeve 46 may encase the pusher bands 44. Alternatively, another material can encase the pusher bands 44. The pusher bands 44 can be made using wire 48 or a piece of or multiple pieces of material, such as, but not limited to, plastic, metal, wire. The pusher bands 44 may be either rigid. The pusher bands 44 may be flexible. For example, the pusher bands may be constructed out of any material configured to be bendable/flexible (such as laser cut tubing), or of a length or sections of material to provide bendability/flexibility of the delivery device 10. The pusher bands can be formed out of a material that remains at least partially radiopaque. In some embodiments the wire 48 can form a helical coil that is wrapped around the inner shaft 26. In some embodiments, the pusher bands 44 need not completely encircle the inner shaft (e.g., be annular). For example, the pusher bands 44 may comprise one or more elements or features positioned about or formed on or into the inner shaft. In some embodiments, the pusher bands 44 are not bendable/flexible (e.g., they are rigid or stiff).

Moving now to FIGS. 7A-7C, certain methods of deployment will now be described. A delivery device 10 can be used as part of a procedure to treat atherosclerotic occlusive disease. The delivery device 10 can be used to deliver one or more intraluminal devices 2, such as tacks, to a site of plaque accumulation. The intraluminal devices 2 can stabilize the site and/or hold pieces of plaque out of the way of blood flow.

The intraluminal devices 2 are preferably self-expandable. Thus, retracting the sheath 12 to reveal an intraluminal device 2 allows the intraluminal device 2 to deploy from the delivery device 10 by self-expansion. The outer sheath 12 can be retracted in increments (e.g., small, equal lengths) to sequentially deliver intraluminal devices 2 at desired locations in a blood vessel. In some embodiments, the increments can correspond with the deployment reference marks 36. The deployment reference marks 36 can be spaced apart by at least the length of the intraluminal devices 2, so that each intraluminal device 2 can be deployed at once or in a two-step process, rather than the gradual release typical of a longer stent. This can allow for more precise placement of the intraluminal devices 2.

Balloon angioplasty is an accepted method of opening blocked or narrowed blood vessels in every vascular bed in the body. Balloon angioplasty is performed with a catheter, e.g., a balloon angioplasty catheter. The balloon angioplasty catheter consists of a cigar shaped, cylindrical balloon attached to a catheter shaft. The balloon angioplasty catheter is placed into the artery from a remote access site that is created either percutaneously or through open exposure of the artery. The balloon angioplasty catheter is passed along the inside of the blood vessel over a wire that guides the way of the balloon angioplasty catheter. The portion of the balloon angioplasty catheter with the angioplasty balloon attached is placed at the location of the atherosclerotic plaque that requires treatment. The angioplasty balloon is inflated to a size that is consistent with the original diameter of the artery prior to developing occlusive disease. In some instances, the angioplasty balloon is coated with, or otherwise configured to deliver, a drug or biologic to the tissue. When the balloon is inflated, the plaque is compressed. Frequently, a segment of the plaque is more resistant to dilation than the remainder of the plaque. When this occurs, greater pressure pumped into the balloon may result in full dilation of the balloon to its intended size. Upon full inflation, the plaque may break: cleavage planes may form within the plaque, permitting the plaque to expand in diameter with the expanding balloon. The angioplasty balloon may then be deflated and removed and the artery segment is re-examined. The process of balloon angioplasty is one of uncontrolled plaque disruption. The lumen of the blood vessel at the site of treatment is usually somewhat larger, but not always and not reliably.

Dilation of the plaque (e.g., some of the cleavage planes created by fracture) with balloon angioplasty can form a dissection. More generally, a dissection occurs when a portion of the plaque or tissue is lifted away from the artery, is not fully adherent to the artery, and may be mobile or loose. The plaque or tissue that has been disrupted by dissection protrudes into the blood flow stream. If the plaque or tissue lifts completely in the direction of blood flow, it may impede blood flow or cause acute occlusion of the blood vessel. There is evidence that dissection after balloon angioplasty must be treated to prevent occlusion and to resolve residual stenosis. There is also evidence that in some circumstances, it is beneficial to place a retaining structure, such as a stent or another intraluminal device, e.g., intraluminal device 2, to hold open the artery after angioplasty and/or force the dissected material back against the wall of the blood vessel to create an adequate lumen for blood flow.

A variety of delivery methodologies and devices can be used to deploy an intraluminal device 2, some of which are described below. For example, an intraluminal device 2 can be delivered into the blood vessel with an endovascular insertion. The delivery devices 10 for the different embodiments of intraluminal devices 2 can be different or the same and can have features specifically designed to deliver the specific intraluminal device 2. The tack and installation procedure may be designed in a number of ways that share a common methodology of utilizing an expansion force of the delivery mechanism (such as balloon expansion) and/or the expansion force of an undulating ring to enable the tack to be moved into position in the blood vessel, then released to an expanded state within the blood vessel. An intraluminal device 2 deployment method can include alignment of radiopaque markers on the outer sheath 12 and the intraluminal device 2 to be deployed prior to deployment.

Referring now FIG. 7A, a delivery device 10 with an outer sheath 12 is shown in a first pre-deployment state. Multiple intraluminal devices 2 can be held by the outer sheath 12 in a compressed state within the delivery device 10. In some embodiments, the intraluminal devices 2 are flash frozen in their compressed state to facilitate loading onto the delivery device 10. The intraluminal devices 2 can extend over a given length of the delivery device 10 as has been described.

The delivery device 10 can be advanced over a guidewire 50 in a patient's vasculature to a treatment site. The guidewire 50 can be the same guidewire 50 used in a prior step of a procedure, such as the guidewire 50 used to position an angioplasty balloon catheter. Once positioned at the treatment location, the outer sheath 12 can be withdrawn or retracted to a second pre-deployment position (FIG. 7B). The second pre-deployment position can be used to adjust the position of the outer sheath 12 to account for any stretching, tortuosity, etc. that may require some adjustment before releasing an intraluminal device 2. In the second pre-deployment position, the distal end 52 of the outer sheath 12 can be positioned at, or slightly distal of the distal end of an intraluminal device 2 to be deployed.

According to some embodiments, the outer sheath 12 can have an outer sheath radiopaque marker 28 (e.g., a radiopaque annular marker band) and the intraluminal device 2 can also have one or more intraluminal device radiopaque markers 22. The intraluminal device radiopaque markers 22 can be positioned in a column around the intraluminal device 2. The distance "L" from the distal end of the intraluminal device 2 to the intraluminal device radiopaque marker 22 can be the same as (e.g., approximately the same as) the distance from the distal end 52 of the outer sheath 12 to the outer sheath radiopaque marker 28. In some embodiments, this distance is to the center of the intraluminal device radiopaque markers 22 and the center of the outer sheath radiopaque marker 28. In some embodiments, the length "L" on the outer sheath 12 is at least as long as the length "L" on the intraluminal device 2, if not slightly longer. The outer sheath 12 can be free from other radiopaque markers. In addition, the intraluminal device 2 can also be free from other radiopaque markers or columns of radiopaque markers. Thus, the outer sheath 12 can have only a single outer sheath radiopaque marker 28 in the distal region that is spaced from the distal-most end 52 of the outer sheath 12 by at least the distance from the distal-most end of the intraluminal device 2 to a intraluminal device radiopaque marker 22 or column of intraluminal device radiopaque markers 22. In the illustrated embodiment, the intraluminal device radiopaque marker 22 or column of intraluminal device radiopaque markers 22 are positioned in the middle of the intraluminal device 2. The intraluminal device radiopaque markers 22 may be positioned on bridge members 18 that connect adjacent undulating rings comprising struts 16. In some embodiments, the intraluminal device radiopaque marker 22 or column of intraluminal device radiopaque markers 22 can be spaced from the distal-most end of the intraluminal device 2 by at least one undulating ring of struts 16. In the illustrated embodiment, the intraluminal device radiopaque marker 22 or column of intraluminal device radiopaque markers 22 is not at the distal-most end of the intraluminal device 2, but is spaced therefrom.

The presence of corresponding radiopaque markers, including intraluminal device radiopaque marker(s) 22 on the intraluminal device 2 and the outer sheath radiopaque marker 28 on the outer sheath 12, can allow the user to align these radiopaque markers prior to deployment of the intraluminal device 2. Further, the user can align these already-aligned radiopaque markers (or can align the radiopaque markers after only one of them has been aligned) with the area to be treated, e.g., the volume or area in which the user desires to deploy an intraluminal device. As will be understood, all of this alignment can be done using standard visualization techniques. As has been mentioned, the pusher bands 44 on the inner shaft 26 can also be radiopaque. In some embodiments, the pusher bands 44 can be identical and can appear different under visualization than both the outer sheath radiopaque marker 28 on the outer sheath 12 and the intraluminal device radiopaque marker(s) 22 on the intraluminal device 2. Thus, it can be clear to the user where all of the radiopaque markers are and which is which. For example, the pusher bands 44 can be axially longer than both or either of the outer sheath radiopaque marker 28 on the outer sheath 12 and the intraluminal device radiopaque marker 22 on the intraluminal device 2. Further, the radiopaque markers on the delivery device 10 (for example, but not limited to, the outer sheath radiopaque marker 28 on the outer sheath 12) can be bands, while the marker(s) on the intraluminal device 2 (for example, but not limited to, the intraluminal device radiopaque marker(s) 22 on the intraluminal device 2) can be dots.

Looking to FIG. 7B, it can be seen that the outer sheath radiopaque marker 28 on the outer sheath 12 and the intraluminal device radiopaque markers 22 on the first intraluminal device 2 are aligned and that the distal end 52 of the outer sheath 12 is positioned at the distal end of the first intraluminal device 2. The delivery device 10 can now be positioned with respect to the lesion for treatment, such as by centering the radiopaque markers at desired location. The outer sheath 12 can then be retracted to place the intraluminal device 2 in the desired location.

In some embodiments, the delivery device 10 can have a radiopaque marker on the outer sheath 12, e.g., the outer sheath radiopaque marker 28, positioned proximally from the distal end 52 at least half the length of the intraluminal device 2, the intraluminal device 2 having a single column of radiopaque markers at the middle of the intraluminal device 2, e.g., intraluminal device radiopaque markers 22. A method of deployment can include retracting the outer sheath 12 until the radiopaque marker on the outer sheath 12 and the radiopaque marker(s) on the intraluminal device 2 to be delivered are aligned, and then aligning these two, already-aligned radiopaque markers with the middle of the lesion to be treated (or other treatment area) before release of the intraluminal device 2, the release being affected by further retracting the outer sheath 12. It will be understood that radiopaque markers on the pusher bands 44 can also be used to help align the delivery device 10 before deployment.

The method can be repeated to deliver multiple intraluminal devices 2 (see FIG. 7B with an intraluminal device 2 shown in the compressed state for reference only). In between intraluminal device 2 deployment, the delivery device 10 may be moved to a completely different lesion or treatment area, or simply repositioned to ensure space between adjacent intraluminal devices 2 once placed.

As discussed previously, in some embodiments, simultaneous placement of the entire intraluminal device 2 can result upon release of the intraluminal device 2 from the delivery device 10. Further, multiple intraluminal devices 2 can placed as desired in a distal to proximal placement or random a random placement within the treatment segment of the vessel.

In some embodiments an expandable intraluminal device 2, such as that shown in FIGS. 3 & 3A, can exert a relatively constant force to a wide range of vessel lumen diameters, thereby allowing a single delivery device 10, e.g., delivery catheter, to deploy multiple intraluminal devices 2 to varying sized vessels. Ideally the intraluminal device 2 can be designed to treat vessels ranging in size, including, but not necessarily limited to, between about 2 mm to 8 mm, about, between about 1.5 mm to 8 mm, between about 1.5 mm to 4.5 mm, between about 2 mm to 6 mm, between about 4 mm to 8 mm, or any other sized intraluminal devices 2 that could advantageously be delivered. It is desirable that the force applied by the intraluminal device 2 to the vessel varies by about 5 N or less over a 3 mm expansion or working range. More ideally the force applied will vary by about 1.5 N or less over a 3 mm expansion or working range.

There are instances where drug coated balloons are being used as an alternative to placing a stent in the vessel. The drug coated balloons, e.g., angioplasty balloons, can dilate narrowing in the vessel and the drug helps to minimize post inflation inflammatory response, which can lead to a re-narrowing of the artery. There is clinical evidence that the combination of an angioplasty balloon and drug can provide an alternative to the implantation of a typical stent which have been historically used to provide both short term and long term scaffolding. Drug coated angioplasty balloons are desirable in that there is no long term implant placed in the vessel. There are instances however when the expansion of a drug coated angioplasty balloon may cause damage to the vessel in the form of a tissue dissection in which case a flap or piece of tissue extends into the lumen of the vessel. The dissection can occur within the angioplasty balloon treatment zone as well as outside of or adjacent to the treatment zone. In these instances it is helpful to tack the dissected tissue against the arterial wall. An intraluminal device 2 having a low outward force can beneficially be used to treat the dissection where a stent may not be appropriate, or desirable.

In some embodiments, the precise placement of the intraluminal device 2 can be set upon positioning of the delivery catheter 10 within the vessel based on the position of a radiopaque marker. Once positioned, one or more intraluminal devices 2 can then be deployed while maintaining the delivery catheter 10 in place and slowly retracting or withdrawing the outer sheath 12.

In some embodiments, one or more intraluminal devices 2 can be deployed at a dissection of tissue. When an angioplasty procedure is performed there are typically one of three outcomes: 1) an optimal outcome, no further stenting or over treatment needs to be performed, 2) residual stenosis, usually requiring the placement of a stent to prop open or scaffold the vessel so that it remains open and does not return to the prior occluded or partially occluded state, and 3) a tissue dissection. A tissue dissection can be where the vessel experiences trauma such as the disruption of an arterial wall resulting in separation of the intimal layer. This may or may not, itself, be flow limiting, but can lead to thrombus formation and flow limitation. One or more intraluminal devices 2 can beneficially be deployed at such a tissue dissection. Small intraluminal devices 2 allow for the treatment of a subset of the portion of the blood vessel treated by the balloon angioplasty procedure thereby providing a treatment therapy with does not require the implantation of long metal stents over the entire angioplasty treatment area. Ideally, one or more intraluminal devices 2 could be used to treat 60% or less of the length of vessel in the angioplasty treatment area. Small intraluminal devices 2 having a single (illustrated) or double column of cells 14, have been shown to cause less injury and to have shorter recovery times than commonly available stents in treating tissue dissections.

Upon placement of the intraluminal device 2, an intravascular construct is formed in situ. The in situ placement can be in any suitable vessel, such as in any peripheral artery. The construct need not be limited to just one or two intraluminal devices 2. In fact, a plurality of at least three intraluminal devices 2 can be provided in an intravascular construct formed in situ. In some embodiments, each intraluminal device 2 has a length of no more than about 8 mm, e.g., about 6 mm in an uncompressed state. In one configuration, at least one of, e.g., each of, the intraluminal devices 2 are spaced apart from an adjacent intraluminal device 2 by between about 1 mm and 4 mm, between about 4 mm and 8 mm, between about 6 mm and 8 mm. In one configuration, at least one of, e.g., each of, the intraluminal devices 2 are spaced apart from an adjacent intraluminal device 2 by at least about 2 mm, at least about 3 mm, at least about 4 mm, at least about 5 mm, at least about 6 mm, at least about 7 mm, at least about 8 mm, at least about 9 mm, at least about 10 mm, at least about 11 mm at least about 12 mm, at least about 13 mm, at least about 14 mm, at least about 15 mm, at least about the length of one intraluminal device 2, or any other spacing that advantageously treats the target volume. Although certain embodiments of the intraluminal devices disclosed herein have a length of 8 mm or less, other embodiments can be longer, e.g., up to about 12 mm or 15 mm long. Of course, it will be understood that, while embodiments are shown in which each intraluminal device of a plurality of intraluminal devices has the same physical size characteristics (e.g., are the same when fully expanded and unconstrained in length, diameter, etc.), one or more intraluminal device of a plurality of intraluminal devices may have a different physical size characteristics (e.g., may be different when fully expanded an unconstrained in terms of at least one of length and diameter). Also, neighboring intraluminal devices 2 can be positioned as close as 2 mm apart, particularly in vessels that are less prone to bending or other movements. In some embodiments, a delivery device 10 can be preloaded with six intraluminal devices 2, each about 6.5 mm long, and can be used to treat lesions up to 15 cm in length, or longer.

In the various delivery devices 10 described herein, the spacing between implanted intraluminal devices 2 can be controlled to maintain a set or a minimum distance between each intraluminal device 2. As can be seen, the delivery devices 10 and/or intraluminal devices 2 can include features that help maintain the desired distance between intraluminal devices 2. Maintaining proper spacing between intraluminal devices 2 can help ensure that the intraluminal devices 2 are distributed over a desired length without contacting each other or bunching up in a certain region of the treated vessel. This can help to prevent kinking of the vessel in which they are disposed. In one configuration, at least one of, e.g., each of, the intraluminal devices 2 are spaced apart from an adjacent intraluminal device 2 by between about 1 mm and 4 mm, between about 4 mm and 8 mm, between about 6 mm and 8 mm. In one configuration, at least one of, e.g., each of, the intraluminal devices 2 are spaced apart from an adjacent intraluminal device 2 by at least about 2 mm, at least about 3 mm, at least about 4 mm, at least about 5 mm, at least about 6 mm, at least about 7 mm, at least about 8 mm, at least about 9 mm, at least about 10 mm, at least about 11 mm at least about 12 mm, at least about 13 mm, at least about 14 mm, at least about 15 mm, at least about the length of one intraluminal device 2, or any other spacing that advantageously treats the target volume.

While a three or four intraluminal device 2 construct formed in situ may be suitable for certain indications, an intravascular construct having at least 5 intraluminal devices 2 may be advantageous for treating loose plaque, vessel flaps, dissections or other maladies that are significantly more elongated (non-focal). For example, while most dissections are focal (e.g., axially short), a series of dissections may be considered and treated as a more elongated malady.

In some cases, even shorter axial length intraluminal devices 2 can be used to treat even more spaced apart locations. For example, a plurality of intraluminal devices 2, each having a length of no more than about 7 mm, can be placed in a vessel to treat a tackable malady. At least some of the intraluminal devices 2 can be spaced apart from an adjacent intraluminal device 2 by at least about 5 mm. In some cases, it may be preferred to provide gaps between adjacent intraluminal devices 2 that can range from about 6 mm to about 10 mm.

Once the vascular implants, e.g., intraluminal devices 2, are placed, there may be areas of the implant that are not fully apposed to the native vessel wall. This may be due to inner lumen wall surface irregularities. Areas where an intraluminal device 2 is not fully apposed to the luminal surface may lead to suboptimal hemodynamic flow. Therefore, optionally, to ensure full apposition of the deployed vascular implant, e.g., intraluminal device 2, a device may be inserted to further expand the intraluminal device 2. For example, a balloon catheter, e.g., an angioplasty balloon catheter, properly sized for the diameter of the deployed intraluminal device 2, may be introduced for post-deployment dilation, positioned within the intraluminal device 2, and then dilated to gently force the intraluminal device 2 against the luminal wall.

Using a separate device, such as the original, or a new, angioplasty balloon, to expand the intraluminal devices 2 to the desired state of expansion, as just discussed, requires placing the intraluminal device 2 with the delivery device 10, removing the delivery device 10, inserting a new device (e.g., a new angioplasty balloon or the original angioplasty balloon, inflating the angioplasty balloon to expand the intraluminal device 2, deflating the angioplasty balloon, and removing the angioplasty balloon from within the vasculature. This additional angioplasty catheter exchange results in more procedure time and cost, and creates or increased the potential for undesirable interactions with the implanted intraluminal devices, such as dislodgement, and vessel wall injury. In addition, if multiple intraluminal devices are placed and deploy to different or diverse range working diameters (e.g., 3 mm to 6 mm), typical angioplasty balloons are not capable of being fully inflated without folds or creases and dilating to that range of working diameters. Therefore, multiple angioplasty balloon catheters would likely be necessary for post deployment dilation of intraluminal devices having varying, e.g., widely varying, deployed diameters.

Therefore, some embodiments of the delivery device 10 include a portion for post-deployment dilation of the intraluminal devices 2. Various embodiments of an intraluminal device delivery system are disclosed that comprise various post deployment dilation devices that provide an integrated dilation feature (e.g., a mechanical dilation feature). The dilation feature can have a wide range of working diameters when inflated (e.g., without folds or creases). For example the dilation feature can operate across a working range of diameters of greater than about 2 mm, greater than about 3 mm, greater than about 4 mm, greater than about 5 mm, greater than about 6 mm, or any other working range of diameters that advantageously facilitates post-deployment dilation of intraluminal devices as disclosed herein. The dilation feature can be used to ensure optimal implant anchoring and circumferential implant apposition to the vessel inner lumen following deployment of an intraluminal device 2, e.g., a self-expanding intraluminal device. Advantages offered by onboard post deployment dilation devices may include: deployment of a plurality of self-expanding intraluminal devices 2; elimination of angioplasty catheter exchanges needed for post-dilation of a self-expanding intraluminal devices 2 and the difficulties and risks associated with the exchange procedure; reduction or elimination of the cost associated with consuming an additional angioplasty balloon catheter(s) for post-dilation of the intraluminal devices 2; shortening procedure durations; and reducing ultimate costs.

The delivery device 10 can be the same as the other delivery devices 10 discussed herein with the addition of a post deployment dilation device. The post deployment dilation device can include an expansion element and an expansion control 1730. The expansion element can take a number of forms, including, for example, expansion filaments 1710, 1910, a bellow 2010, or inner core balloon 2110. In some embodiments, the expansion element comprises a movable frame where one end of the frame is configured to move towards the other end to thereby expand the frame. The frame can be made of expansion filaments 1710, 1910, or a bellow 2010, among other designs. The expansion element can be positioned in a deployment platform 8.

The expansion control 1730 can be positioned at or in the proximal region 6 of the delivery device 10 and may be actuated by a user to control expansion of the expansion element. In some embodiments, the expansion control 1730 can be a trigger, a cable, or an end region of one or more filaments.

The post deployment dilation device can include one or more radiopaque markers, such as bands or rings, such as the distal radiopaque ring 1720 and the proximal radiopaque ring 1722. The one or more radiopaque markers can be at one or more ends, the center, or at other locations of the post deployment dilation device. The one or more radiopaque markers may also be movable with the expansion of the expansion element. In some embodiments, the distal-most pusher band 44 on the inner shaft 26 can define the proximal end of the post deployment dilation device. The nose cone 38 can define the distal end of the post deployment dilation device. As both the nose cone 38 and the pusher band 44 can be radiopaque, the post deployment dilation device may not need to include any additional radiopaque markers.

Generally speaking, the delivery device 10 may include one or more delivery platforms 8, as described herein, which may be exposed by retraction, e.g., the proximal axial sliding, of an outer sheath 12 (they alternatively may be covered by the advancement, e.g., distal axial sliding, of an outer sheath 12). The delivery platforms 8 are configured to accept and hold one or more intraluminal devices (e.g., self-expanding intraluminal devices 2). The intraluminal devices 2 may be released or deployed within a volume, such as a blood vessel, by retracting or withdrawing the outer sheath 12 to expose the delivery platform 8. In addition to the delivery platforms 8 that are configured to hold and then release one or more (e.g., a plurality) intraluminal devices 2, the delivery device 10 may include a post deployment dilation device.

As disclosed herein, post deployment dilation devices are part of the delivery device 10, at least a portion of which may be positioned within a deployed or already-expanded intraluminal device 2 (e.g., a self-expanding intraluminal device 2 that has been allowed to expand). The post deployment dilation devices disclosed herein may have a first pre-deployment diameter that is substantially the same as or close to the diameter of an inner portion of the delivery device 10. They may also have a second deployment diameter that is larger than the first pre-deployment diameter. Once positioned within the intraluminal device 2, the post deployment dilation device may be radially expanded to push outwardly on the inner surface of the intraluminal device 2. Stated differently, the post deployment dilation device is configured such that at least a portion of the post deployment dilation device contacts at least a portion of the inner surface of an intraluminal device 2 and applies a radial force to that inner surface of the intraluminal device 2. By the application of an outward or radial force to the inside of the intraluminal device 2 (i.e., at least a portion of the inner surface of the intraluminal device 2), the post deployment dilation device may cause the intraluminal device 2 to expand even further and/or seat more evenly against the surface of the volume in which it is contained (e.g., the blood vessel). After the post deployment dilation device has expanded to exert an outward/radial force on the intraluminal device 2, it may be contracted and/or compressed so that it may be moved out (e.g., withdrawn or retracted) from underneath or within the deployed intraluminal device 2 without entanglement with the intraluminal device 2.

A delivery device 10 may include only one, or multiple, post deployment dilation devices. When only one post deployment dilation device is included, the post deployment dilation device may be located distal of the first delivery platform 8, between a first and second delivery platform 8, underneath a delivery platform 8, between any delivery platforms 8, or even proximal to all delivery platforms 8. A delivery device 10 may include more than one post deployment dilation device, for example, two, three, four, five, or six, post deployment dilation devices. When more than one post deployment dilation device is included, the post deployment dilation devices may be located distal and proximal to the delivery platforms 8, between two or more of the delivery platforms 8, or within two or more of the delivery platforms 8.

As described elsewhere herein, the delivery device 10 may be operated/actuated at its proximal region 6, for example to retract the outer sheath 12 and deploy one or more intraluminal devices 2. In much the same way, the post deployment dilation devices disclosed herein may be actuated from the proximal region 6 of the delivery device 10. That way, an operator may insert the delivery device 10 into a volume, e.g., a patient's blood vessel, advance the delivery device 10 to a target site, retract the outer sheath 12, deploy an intraluminal device 2, and use the post deployment dilation device, all from the proximal region 6 of the delivery device 10.

At least some embodiments of the post deployment dilation device include a plurality of expansion filaments 1710, and expansion filaments 1910 as shown in FIGS. 8A-10F. As will be explained in more detail below, the expansion filaments 1710, and expansion filaments 1910 can take many forms, such as being free floating or fixed with respect to either the proximal or the distal region of the post deployment dilation device. The expansion filaments 1710, and expansion filaments 1910 can be pre-bent, formed or shaped so that when expanded they can assume a cylindrical shape or other shape consistent with the desired shape of the vessel(s). For example, as shown in FIG. 8F, the expansion filaments 1710 have two bends on each end region to collectively form end caps that connect to longitudinal sections that are parallel with the longitudinal axis of the inner shaft 26.

When fixed with respect to the distal end region of the post deployment dilation device (FIGS. 8A-8G), the expansion filaments 1710 may be pushed or extended distally toward the distal end of the post deployment dilation device. Such pushing or extension can cause the expansion filaments 1710 to bow, or buckle outwards. Additional pushing or extension of the expansion filaments 1710 can cause the expansion filaments 1710 to bow or buckle even further outwards. When the post deployment dilation device is inside an intraluminal device 2, the expansion filaments 1710 can be pushed or extended far enough that they contact and exert an outward or radial force on the intraluminal device 2 (as discussed herein). Once the post deployment dilation device has been used (e.g., exerted a radial force on the inner surface of the intraluminal device 2), the expansion filaments 1710 may be retracted. Retraction of the expansion filaments 1710 can cause them to lie flat against the delivery device 10 so that the delivery device 10 may be moved, e.g., withdrawn, while reducing or eliminating the risk of getting caught on the intraluminal device 2.

Alternatively, the expansion filaments 1910 may be fixed with respect to the proximal end region of the post deployment dilation device (FIGS. 10A-10F). When fixed with respect to the proximal end region of the post deployment dilation device, the expansion filaments 1910 may be fixed at their distal end region to a slidable structure, for example, a sliding sleeve 1920, e.g., a ring configured to slide proximally and distally over, across, or along the inner shaft 26. When the slidable structure is slid (e.g., pulled or drawn) toward the proximal end region of the delivery device 10 (also toward the proximal fixation points of the expansion filaments 1910), the expansion filaments 1910 are caused to bow or buckle outwards. Additional proximal sliding of the slidable structure causes the expansion filaments 1910 to bow or buckle even further outwards. If the post deployment dilation device is inside an intraluminal device 2, the slidable structure can slide proximally far enough so that the expansion filaments 1910 bow outward to contact and exert an outward or radial force on the intraluminal device 2 (as discussed herein). Once the post deployment dilation device has been used (e.g., exerted a radial force on the inner surface of the intraluminal device 2), the slidable structure may be pushed distally. Pushing the slidable structure distally causes the expansion filaments 1910 to lie flat against the delivery device 10 so that the delivery device 10 may be moved, e.g., withdrawn, while reducing or eliminating the risk of getting caught on the intraluminal device 2. One expansion filament-based post deployment dilation device may be included, or more than one expansion filament-based post deployment dilation device may be included (e.g., one set of expansion filaments 1910 incorporated into each delivery platform 8).

In some embodiments, the expansion filaments 1910 can be positioned within a lumen in the inner shaft 26 and distal movement of the sliding sleeve 1920 can retract the expansion filaments 1910. The expansion filaments 1910 can then assume a pre-bent or shaped expanded form to further expand the intraluminal device 2.

Another post deployment dilation device disclosed herein includes a flexible bellow 2010 (FIGS. 11A-11F). Such flexible bellows 2010 may have a first configuration in which the bellow 2010 is extended and lies substantially flat against the delivery device 10. They may also have a second configuration in which the bellow 2010 is shortened or contracted or expanded. When in its second configuration, the bellow 2010 may have a diameter larger than when in its first configuration. Some of the bellows 2010 disclosed herein are shaped like an accordion so that when fully extended (in their pre-deployment configuration) they lie substantially flat. However, retraction of these bellows 2010 can cause them to fold on themselves, like an accordion. This accordion-like action causes the diameter of the bellow 2010 to increase as it is shortened. These bellows 2010 may be fixed with respect to the proximal end region of the post deployment dilation device (i.e., the proximal end region of the bellow 2010 is fixed with respect to the proximal end region of the post deployment dilation device), the distal end region of the post deployment dilation device (i.e., the distal end region of the bellow 2010 is fixed with respect to the distal end region of the post deployment dilation device), or, alternatively, both the proximal and distal end regions of the bellow 2010 may be independently movable. One bellow-based post deployment dilation device may be included or more than one bellow-based post deployment dilation device may be included (e.g., one bellow 2010 incorporated into each delivery platform 8).

Still other post deployment dilation devices disclosed herein include an inflatable balloon (e.g., an inner core balloon 2110, FIGS. 12A-12F). Such balloons may have a pre-deployment configuration having a first diameter which allows the inner core balloon 2110 to lie close to an inner portion of the delivery device 10 (such that the outer sheath 12 may fit over the inner core balloon 2110 when the inner core balloon 2110 is not inflated). Such balloons may have a preformed shape (e.g., bi-fold, tri-fold, quad-fold, spiral wrap, and the like) that assists the inner core balloon 2110 in maintaining a low profile in its uninflated state both pre-inflation and post-inflation. These shapes may, for example, be achieved by: forming the inner core balloon 2110 in that shape (e.g., a tri-fold shaped mold); post-processing the inner core balloon 2110 after forming (e.g., heat-set); using tubing with varying wall thickness around the tubing to form the inner core balloon 2110; forming the inner core balloon 2110 to have varying wall thickness at any part of the inner core balloon 2110, such as differences in thickness radially around the inner core balloon 2110, and/or differences in wall thickness at the tapers compared to the working length, and/or where attached to the inner shaft 26 or outer sheath 12. The inner core balloon 2110 properties and geometry including, but not limited to, formed diameter, minimum inflated diameter, compliance, working range, maximum inflated diameter, taper length and taper angle, thickness of the balloon material at all parts of the balloon, inherent material properties, post processing the balloon to modify the material or configuration of the balloon, and the like, can be tailored to achieve the desired deflated and inflated profile, flexibility, compliance, working diameter range, burst strength, lubricity, etc.

The inner core balloon 2110 may also have a deployment configuration having a second diameter or diameter range. For example, the inner core balloon 2110 may have an expanded diameter to which the inner core balloon 2110 may be inflated in the range of between about 1.5 mm to 8 mm, between about 1.5 mm to 4.5 mm, between about 2 mm to 6 mm, between about 4 mm to 8 mm. The inner core balloon 2110 may have an expanded diameter to which the inner core balloon 2110 may be inflated of at least about 2 mm, at least about 3 mm, at least about 4 mm, at least about 5 mm, at least about 6 mm, at least about 7 mm, at least about 8 mm, at least about 9 mm, at least about 10 mm, at least about 11 mm, at least about 12 mm, at least about 13 mm, at least about 14 mm, at least about 15 mm, or any other diameter that advantageously facilitates post deployment dilation as disclosed herein. As will be readily understood, when placed inside a substantially fixed volume, additional inflation of the inner core balloon 2110 will cause additional radial or outward pressure on the inner surface of the volume. One balloon-based post deployment dilation device may be included or more than one balloon-based post deployment dilation device may be included (e.g., one inner core balloon 2110 incorporated into each delivery platform 8). The inflatable inner core balloon 2110 can also be used to deliver drugs or biologic therapies to the vessel wall. Delivery of drugs or biologic therapies can be accomplished by, for example, but not limited to, coating the inner core balloon 2110 with the drugs or biologic therapies, a material that contains the drugs or biologic therapies, and/or an inner core balloon 2110 that is permeable to the drugs or biologic therapies through which the drugs or biologic therapies are delivered.

The inner core balloon 2110 may be coated to modify one or more properties of the underlying material. For example, a coating may be applied to advantageously increase or decrease the lubricity of the inner core balloon 2110. Coating types may include, but are not limited to, hydrophilic, hydrophobic, fluorinated polymer, and silicone-based coatings. The inner core balloon 2110 may have a surface that is not smooth (e.g., is textured) to enable the inner core balloon 2110 to resist movement of the inner core balloon 2110 (compared to a smooth inner core balloon 2110) when inflating within the deployed intraluminal device 2. The surface of the inner core balloon 2110 may, for example, be similar to the surfaces of the sleeve 46 as shown in FIGS. 6B-6D.

Figure 14A:
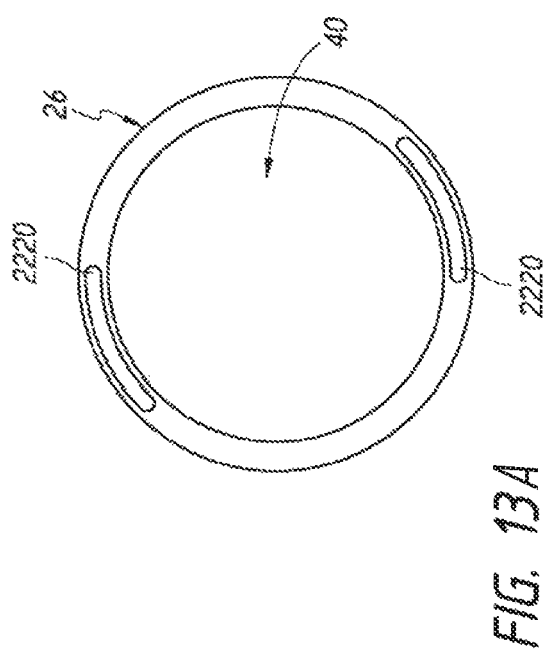
FIGS. 14A-14B show a helical filament system for capturing and confining a post-dilated inner core balloon.

One or more embodiments incorporating a balloon into the post deployment dilation device also includes a helical filament 2330 (FIG. 14B) to trap the balloon in its pre-deployment configuration. The helical filament 2330 may be extended from and retraced into a helical filament lumen 2320 (FIG. 14A). Retracting the helical filament 2330 into a lumen can cause it to release the balloon so that the balloon may be inflated. Extending the helical filament 2330 from a lumen can cause it to wrap helically around the balloon to trap it next to an inner portion of the delivery device 10. Trapping the balloon with the helical filament 2330 may be particularly useful after the balloon has been used (e.g., placed within an intraluminal device 2, inflated to deploy the intraluminal device 2, and deflated). Without the helical filament 2330, the deflated balloon may catch on biological structures or the deployed intraluminal device 2. However, the helical filament 2330 can cause the balloon to, once again, lie close against an inner portion of the delivery device 10.

FIGS. 8A-8G illustrate a delivery device 10 incorporating an embodiment of a post deployment dilation device. More specifically, the delivery system comprises an integrated distal expansion element used to dilate the intraluminal devices 2 after deployment to ensure ideal apposition between the intraluminal devices 2 and the vessel wall. Similar to the delivery device 10 shown in FIG. 7A, the delivery device 10 shown in FIG. 8A includes an outer sheath 12 in a first pre-deployment position. As has been described, multiple intraluminal devices 2 can be held by the outer sheath 12 in a compressed state within the delivery device 10 and can extend over a given length of the delivery device 10. The delivery device 10 includes a guidewire lumen 40 which can extend over a guidewire 50 so that the delivery device 10 can be advanced over the guidewire 50 in a patient's vasculature to a treatment site. As has already been described, the guidewire 50 can be the same guidewire 50 used in prior steps of a procedure. The outer sheath 12 can be withdrawn or retracted to a second pre-deployment position (shown in FIGS. 7B and 7C). In the second pre-deployment position, the distal end 52 of the outer sheath 12 can be positioned at, or slightly distal of the distal end of an intraluminal device 2 to be deployed.

Like the systems shown in prior figures, the outer sheath 12 can have an outer sheath radiopaque marker 28 and the intraluminal device 2 can also have one or more intraluminal device radiopaque markers 22. The intraluminal device radiopaque markers 22 can be positioned in a column around the intraluminal device 2. Having corresponding intraluminal device radiopaque markers 22 on the intraluminal device 2 and an outer sheath radiopaque marker 28 on the outer sheath 12 can allow the user to align the intraluminal device radiopaque markers 22 and outer sheath radiopaque marker 28 prior to deployment of the intraluminal device 2 as shown in FIG. 8C. Furthermore, the aligned intraluminal device radiopaque markers 22 and outer sheath radiopaque marker 28 may be aligned with the desired area to be treated. Alignment can be accomplished using standard visualization techniques. As has been mentioned, the pusher bands 44 on the inner shaft 26 can also be radiopaque.

With reference to FIG. 8B, it can be seen that the outer sheath radiopaque marker 28 on the outer sheath 12 and the intraluminal device radiopaque markers 22 on the first intraluminal device 2 are aligned and that the distal end of the outer sheath 12 is positioned at the distal end of the first intraluminal device 2. The delivery device 10 can now be positioned with respect to the target volume, e.g., the lesion for treatment, such as by centering the radiopaque markers at the desired location. The outer sheath 12 can then be retracted to place the intraluminal device 2 in the desired location. In addition to positioning the outer sheath 12 such that the intraluminal device 2 may be deployed, aligning the outer sheath radiopaque marker 28 on the outer sheath 12 with the intraluminal device radiopaque markers 22 on the first intraluminal device 2 at least partially exposes a first platform 8 incorporating a post deployment dilation device. In some embodiments, it is not necessary to have or achieve exact alignment between the intraluminal device radiopaque markers 22 and the outer sheath radiopaque marker 28. It may be desirable to have the intraluminal device radiopaque markers 22 positioned with respect to the target volume, e.g., the lesion for treatment.

FIGS. 8B and 8C illustrate the post deployment dilation device in a collapsed state. The post deployment dilation device includes a distal radiopaque ring 1720, a proximal radiopaque ring 1722, and a plurality of expansion filaments 1710. Distal radiopaque ring 1720 is generally positioned at or close to the distal end region of the post deployment dilation device's platform. By extension, proximal radiopaque ring 1722 is generally positioned at or close to the proximal end region of the post deployment dilation device's platform. The post deployment dilation device shown in FIG. 8 has a streamlined pre-deployment configuration and a deployment configuration, which will be discussed in further detail below. FIGS. 8B and 8C show the post deployment dilation device in its pre-deployment configuration.

As mentioned above, the post deployment dilation device includes a plurality of expansion filaments 1710. The expansion filaments 1710 can form a frame. In some embodiments, the post deployment dilation device has 3 expansion filaments 1710. In other embodiments, the post deployment dilation device has 4, 5, 6, 7, 8, 9, 10, 11, or 12 expansion filaments 1710. On still other embodiments, the post deployment dilation device has more than 12 expansion filaments 1710. The expansion filaments 1710 are fabricated out of a flexible material that retains enough rigidity that it can push radially outward, as will be discussed below. In some embodiments, the expansion filaments 1710 are made out of a polymer. In other embodiments, the expansion filaments 1710 are made out of a metal, such as a super-elastic metal (e.g., nitinol). The distal portion of each expansion filament 1710 can be pre-shaped to allow for optimal engagement with the inner surface of an intravascular device 2 and subsequent expansion of the intravascular device 2. In some embodiments, expansion filaments 1710 can be made out of a combination of materials (e.g., each expansion filament 1710 having a metal core with a polymer outer layer). In some embodiments, expansion filaments 1710 can be covered by a thin, flexible polymer film, which may or may not be coated as discussed herein. This may advantageously help distribute the expansion forces more equally over the surface area of the intravascular device 2. The polymer film may also help mitigate the potential for entanglement of the expansion filaments 1710 into the structure of the intravascular device 2 during dilation. The polymer film can also be used to deliver drugs or biologic therapies to the wall of the blood vessel. Alternatively, in other embodiments, the expansion filaments 1710 may be embedded in the wall of a very fine, very flexible, continuous, expandable structure, such as a balloon. Being so embedded advantageously prevents the expansion filaments 1710 from becoming entangled with and/or caught on the struts 16, anchors 20, or any other part of the intravascular device 2 that is being deployed.

As illustrated, the distal portion of each expansion filament 1710 in the plurality of expansion filaments 1710 is fixed with respect to the inner shaft 26 near the distal end region of the post deployment dilation device's platform (e.g., near the distal radiopaque ring 1720). They can be fixed in approximately equal divisions around the delivery device 10. For example, in an embodiment in which the post deployment dilation device has only 3 expansion filaments 1710, each expansion filament 1710 is separated from the next expansion filament 1710 by about 120°. In the same way, in an embodiment of the delivery device 10 in which the post deployment dilation device has 6 expansion filaments 1710, each expansion filament 1710 is separated from the next expansion filament 1710 by about 60°.

The expansion filaments 1710 extend proximally from their attachment points with respect to the inner shaft 26, over the post deployment dilation device's platform, and underneath, through, or along the marker bands 44 and the various delivery platforms 8, to a proximal region 6 of the delivery device 10. The various expansion filaments 1710 may each, individually extend all the way to a proximal region 6 of the delivery device 10. Alternatively, the various expansion filaments 1710 may join together, proximal of the post deployment dilation device's platform, to form a single cable that extends proximally to the proximal region 6 of the delivery device 10. A proximal portion of each expansion filament 1710 (or, as just discussed, the single cable comprising each and every expansion filament 1710), can be fixed to an expansion control 1730 at or in the proximal region 6 of the delivery device 10 that may be actuated by a user, e.g., the physician.

In some embodiments, the inner shaft 26 is formed to include a plurality of lumens through which the expansion filaments 1710 may travel from the post deployment dilation device to the proximal region 6 of the delivery device 10. The inner shaft 26 may consist of a multi-lumen tube as shown in FIG. 9A. FIG. 9A illustrates a cross-section of inner shaft 26 having a guidewire lumen 40 at its center as well as eight individual filament lumens 1810 within its wall (e.g., which may be substantially parallel to the guidewire lumen 40). An expansion filament 1710 may be run from the post deployment dilation device all the way to the proximal region 6 of the delivery device 10, through these filament lumens 1810. The filament lumens 1810 generally provide support and coaxial containment for the multiple expansion filaments 1710 that extend through the filament lumens 1810 from a proximal to distal portion of the delivery device 10.

As will be readily understood, the inner shaft 26 may include any number of filament lumens 1810, including 3 filament lumens 1810. In some embodiments, the inner shaft 26 has 4, 5, 6, 7, 8, 9, 10, 11, or 12 filament lumens 1810. In yet other embodiments, the inner shaft 26 has more than 12 filament lumens 1810. Each filament lumen 1810 may contain an expansion filament 1710. For example, an inner shaft 26 may contain a certain number of filament lumens 1810 (e.g., 8 filament lumens 1810) then the same number of expansion filaments 1710 (i.e., 8 expansion filaments 1710) are inserted into the filament lumens 1810. Such 1:1 ratios may be useful for highly tailored systems. However, by contrast, some of the filament lumens 1810 may not contain expansion filaments 1710. For example, an inner shaft 26 may contain a comparatively large number of filament lumens 1810 (e.g., 12 filament lumens 1810). Then, only the desired number of expansion filaments 1710 (e.g., 6 expansion filaments 1710) are inserted into the filament lumens 1810. This type of system is more modular and may decrease manufacturing costs as a single inner shaft 26 may accommodate various numbers of expansion filaments 1710 or the remaining expansion filament lumens 1810 may be used for other purposes (sensors, sensor wires, etc.).

As shown in FIG. 9B, the expansion filaments 1710 may exit the filament lumens 1810 to extend across the surface of the post deployment dilation device's platform (e.g., the outer surface of the inner shaft 26). In some embodiments, the distal section of the multi-lumen tube having the filament lumens 1810 incorporates several longitudinally oriented openings, or pockets, in the wall of the tubing (e.g., one opening or pocket for each filament lumen 1810). The windows or pockets are generally aligned with a distal portion of the filament lumens 1810 in the inner core multi-lumen tubing to enable exposure of a distal portion of the expansion filaments 1710 (e.g., the expansion filaments 1710 may exit these windows to travel across the surface of the post deployment dilation device's platform to their respective attachment points). Alternatively, as shown in FIG. 9B, the expansion filaments 1710 may reside in a plurality of filament recesses 1820, which are essentially open-top extensions of the filament lumens 1810. Using such filament recesses 1820 may advantageously save space, prevent the expansion filaments 1710 from interacting with each other, and prevent binding and/or excessive friction between the outer sheath 12, expansion filaments 1710, and the inner shaft 26.

In some embodiments, the expansion filaments 1710 can exit the filament lumens 1810 adjacent to a pusher band 44. In this way the pusher band 44 can be used to increase the rigidity and structural integrity of the inner shaft 26. The nose cone 38 can also be used in this manner. For example, metal radiopaque marker bands in the pusher band 44 and in the nose cone 38 can surround the filament lumens 1710 adjacent the exits locations of the expansion filaments 1710. This can help the delivery device 10 deal with the increased stress on the inner shaft 26 when the expansion filaments 1710 are in the expanded position. As has been mentioned, the pusher band and nose cone can define the respective proximal and distal ends of the post deployment dilation device.

As illustrated, in the post deployment dilation device's pre-deployment state, each expansion filament 1710 lies substantially flat against the inner shaft 26 (or in a filament recess 1820 of the inner shaft 26). In the pre-deployment state, there can be little, if any, slack in each expansion filament 1710. That is to say that the length of the expansion filament 1710 between its fixation point at the distal end region of the post deployment dilation device's platform and the distal end region of the filament lumen 1810 is about the same as the length of the post deployment dilation device's platform.

Activation of the expansion control 1730 causes the distal advancement of the expansion filaments 1710 through the lumens, which further results in the radial expansion of a distal portion of the expansion filaments 1710 through the openings in the wall of the tube. Deployment (i.e., activation of the expansion mechanism) is accomplished by pushing on the proximal end regions of the various expansion filaments 1710 (or the cable formed by the various expansion filaments 1710). This causes the expansion filament 1710 to extend out of the distal end region of its filament lumen 1810 (e.g., distal advancement of the expansion filaments 1710 through the lumens), thereby resulting in an extension and radial expansion of a distal portion of the expansion filaments 1710 through the filament lumens 1810, which further results in the radial expansion of a distal portion of the expansion filaments 1710 through the openings in the wall of the tube. Extension of the distal portion of an expansion filament 1710 increases the length of the expansion filament 1710 between the attachment point at the distal end region of the post deployment dilation device and the distal end region of the filament lumen 1810. As the length of the expansion filament 1710 above the post deployment dilation device increases, it will "buckle" outward. Pushing more of the expansion filament 1710 out of the filament lumen 1810 causes the expansion filament 1710 to buckle even further outward. That is to say, the expansion diameter of the expansion filaments 1710 is controlled by the longitudinal displacement of the proximal end region of the expansion filaments 1710.

FIGS. 8D-8G illustrate a method of using the post deployment dilation device just discussed. In FIG. 8D, the outer sheath 12 has been retracted, as discussed elsewhere herein, until the outer sheath radiopaque marker 28 overlies the intraluminal device radiopaque marker 22, ready to deploy the second intraluminal device 2. As can be seen, the first intraluminal device 2 has expanded to be substantially apposed to the intraluminal wall. When contained by the outer sheath 12, the intraluminal device radiopaque markers 22 are generally close together, in a tightly packed ring. By contrast, expansion of the intraluminal device 2 causes the intraluminal device radiopaque markers 22 to also expand outward, thereby forming a more disperse ring. Therefore, the user, using standard imaging techniques as discussed elsewhere herein, may observe the intraluminal device 2 unseating from its delivery platform 8 and expanding within the vessel. During deployment of the individual intraluminal devices 2, the expansion filaments 1710 are completely contained within the pockets/filament recesses 1820 and the inner shaft 26 wall (or filament recesses 1820).

Once the intraluminal device 2 has been deployed to its target location and stopped expanding within the vessel (i.e., no more or very little motion of the intraluminal device radiopaque markers 22 is observed), the delivery device 10 is moved either proximally or distally and repositioned such that the post deployment dilation device is moved underneath the intraluminal device 2, shown in FIG. 8E. In this position, the centers of the exposed distal end regions of the expansion filaments 1710 are located at the approximate center of the deployed intraluminal device 2.

A portion of the inner shaft 26 or a portion of the expansion filaments 1710, can include one or more radiopaque elements to allow for optimal longitudinal alignment of the expansion filaments 1710 within the deployed implant. For example, the post deployment dilation device may incorporate the distal radiopaque ring 1720 and the proximal radiopaque ring 1722, which can be used to center the post deployment dilation device approximately within the center of the intraluminal device 2. The distal radiopaque ring 1720 and the proximal radiopaque ring 1722 can be observed using conventional imaging techniques. Consequently, the user may advance or retract the delivery device 10 until the intraluminal device radiopaque markers 22 lie substantially in the middle of the distal radiopaque ring 1720 and the proximal radiopaque ring 1722. At that point, the intraluminal device 2 will be in approximately the center of the post deployment dilation device—the proper location for activation of the post deployment dilation device.

When the post deployment dilation device is approximately centered under the intraluminal device 2, the expansion mechanism may be activated by pushing distally on the proximal end region of the expansion filaments 1710, or the proximal end region of the cable comprising the expansion filaments 1710, at the proximal end region of the expansion filament 1710. As described above, this causes expansion of each expansion filament 1710 out of its distal sectioned filament recess 1820. The radial expansion of the expansion filaments 1710, or "buckling," causes the expansion filaments 1710 to engage with the inner surface of the intraluminal device 2, as shown in FIG. 8F. As the expansion filaments 1710 continue to expand radially, they continue to push radially outward on the inner surface of the intraluminal device 2, thereby fully dilating the deployed intraluminal device 2 against the inner wall of the vessel (vessel not shown).

Following radial expansion of the expansion filaments 1710 and complete deployment of the intraluminal device 2, the expansion mechanism can be deactivated by pulling proximally on the proximal end region of the expansion filaments 1710, or the proximal end region of the cable comprising the expansion filaments 1710, at the proximal end region of the expansion filament 1710. As described above, this causes each expansion filament 1710 to retract back into its distal sectioned pocket or filament recess 1820, to once again lie flat against the inner shaft 26, shown in FIG. 8G.

While the post deployment dilation device shown in FIGS. 8A-8F was described as being located at or in the distal region 4 of the delivery device 10, between the nose cone 38 and the distal-most intraluminal device 2, it should be understood that the post deployment dilation device can be placed elsewhere on the delivery device (e.g., proximal to one or more of the delivery platform(s) 8) and that a plurality of such post deployment dilation devices may be included in the delivery device 10. For example, one post deployment dilation device (e.g., plurality of expansion filaments 1710) may be incorporated under each intraluminal device 2, e.g., into the delivery platform 8 underlying the intraluminal device 2. In such embodiments, each post deployment dilation device may have controls accessible at or in the proximal region 6 of the delivery device 10. Therefore, a user may retract the outer sheath 12 to deploy an intraluminal device 2, and, without moving the delivery device 10, activate the post deployment dilation device underlying the intraluminal device 2 to post-dilate the intraluminal device 2. However, it should be understood that the post deployment dilation device can be placed on the outer sheath 12 using similar construction principles.

FIGS. 8A-8G illustrate a delivery device 10 having a post deployment dilation device incorporating expansion filaments 1710 that are fixed at the distal end region of the post deployment dilation device and translatable/extendable with reference to the proximal end region of the post deployment dilation device (and the delivery device 10 as a whole). The delivery device 10 of FIGS. 10A-10F is very similar to the delivery device 10 of FIGS. 8A-8G. However, in FIGS. 10A-10F the proximal end regions of the expansion filaments 1910 are fixed to the proximal end region of the post deployment dilation device. And, it is the distal end regions of the expansion filaments 1910 that translate to cause radial expansion of the expansion filaments 1910.

FIGS. 10A-10C show the post deployment dilation device in various stages of deployment: FIG. 10A illustrates the post deployment dilation device in a pre-deployment state (i.e., fully collapsed); FIG. 10B illustrates the post deployment dilation device in a state of partial deployment; and FIG. 10C illustrates the post deployment dilation device in a state of substantially full deployment.

The illustrated post deployment dilation device generally includes distal radiopaque ring 1720, a proximal radiopaque ring 1722, and a plurality of expansion filaments 1910. Distal radiopaque ring 1720 and proximal radiopaque ring 1722 may be the same as has already been described with respect to FIG. 8. In some embodiments, the post deployment dilation device has 3 expansion filaments 1910. In other embodiments, the post deployment dilation device has 4, 5, 6, 7, 8, 9, 10, 11, or 12 expansion filaments 1910. On still other embodiments, the post deployment dilation device has more than 12 expansion filaments 1910. The expansion filaments 1910 are fabricated out of a flexible material that retains enough rigidity that they can push radially outward, as will be discussed below. Similar to the expansion filaments 1710 of FIG. 8, the expansion filaments 1910 can be made out of a polymer, metal, a super-elastic metal (e.g., nitinol), or a combination thereof. The distal portion of each expansion filament 1910 can be pre-shaped to allow for optimal engagement with the inner surface of an intraluminal device 2 and subsequent expansion of the intraluminal device 2. In some embodiments, each expansion filament 1910 is covered by a thin, flexible polymer film, which may or may not be coated as discussed herein. This may advantageously help distribute the expansion forces more equally over the surface area of the intravascular device 2. The polymer film may also help mitigate the potential for entanglement of the expansion filaments 1910 into the structure of the intravascular device 2 during dilation. The polymer film can also be used to deliver drugs or biologic therapies to the wall of the blood vessel. Alternatively, in other embodiments, the expansion filaments 1910 may be embedded in the wall of a very fine, very flexible, continuous, expandable structure, such as a balloon. Thus, the expansion filaments 1910 can form a frame inside the balloon.

By contrast to FIG. 8, the proximal portion of each expansion filament 1910 in the plurality of expansion filaments 1910 is fixed with respect to the inner shaft 26 near the proximal end region of the post deployment dilation device's platform (e.g., near the proximal radiopaque ring 1722). They can be fixed in approximately equal divisions around the delivery device 10. For example, in an embodiment in which the post deployment dilation device has only 3 expansion filaments 1910, each expansion filament 1910 is separated from the next expansion filament 1910 by about 120°. In the same way, in an embodiment of the delivery device 10 in which the post deployment dilation device has 6 expansion filaments 1910, each expansion filament 1910 is separated from the next expansion filament 1910 by about 60°. In some embodiments, the proximal end regions of the expansion filaments 1910 are attached to the inner shaft 26 at the proximal end region of the post deployment dilation device's platform. In other embodiments, the expansion filaments 1910 extend back, some distance, into the wall of the inner shaft 26, such as through filament lumens 1810 as was described with respect to FIG. 9A. In such embodiments, the plurality of expansion filaments 1910 align with radially sectioned pockets (such as the filament lumens 1810 of FIG. 9A) around the circumference of the inner shaft 26 and terminate to a fixed position within the filament lumens 1810 in the wall of the inner shaft 26, proximal to the first crimped intraluminal device 2.

The expansion filaments 1910 extend distally from their attachment points with respect to the inner shaft 26, over the post deployment dilation device's platform, and attach to a sliding sleeve 1920. The expansion filaments 1910 may be contained within filament recesses 1810, when not deployed, as has already been described. The length of the expansion filaments 1910 (e.g., when straight and unbent) result in the sliding sleeve 1920 being positioned in its relative "home" position (e.g., near the distal radiopaque ring 1720) with no preload, shown in FIG. 10A. The sliding sleeve 1920 is operatively coupled to an expansion control 1730, such as a retractor, in the proximal region 6 of the delivery device 10. The retractor, e.g., expansion control 1730, allows a user to cause the sliding sleeve 1920 to slide, coaxially, along the inner shaft 26. In some embodiments, the retractor, e.g., expansion control 1730, may be simply one filament or a series of filaments attached to the sliding sleeve 1920, extending over the surface of the post deployment dilation device's platform, into the wall of the inner shaft 26 (e.g., through filament lumens 1810), and to the proximal region 6 of the delivery device 10.

In operation, the retractor, e.g., expansion control 1730, may be pulled proximally, thereby causing the sliding sleeve 1920 to slide proximally along the surface of the inner shaft 26. FIG. 10B shows a sliding sleeve 1920 that has been slid partially in the proximal direction. FIG. 10C shows a sliding sleeve 1920 that has been slid even further in the proximal direction. As discussed herein, the expansion filaments 1910 can have a fixed length. With a fixed length, sliding the sliding sleeve 1920 proximally, towards the expansion filaments' 1910 points of attachment to the inner shaft 26, causes the expansion filaments 1910 to "buckle" outward. Sliding the sliding sleeve 1920 even further proximally causes the expansion filaments 1910 to buckle even further outward. That is to say, the expansion diameter of the expansion filaments 1910 is controlled by the longitudinal displacement of the sliding sleeve 1920.

FIGS. 10D-10F illustrate a method of using the post deployment dilation device just discussed. In FIG. 10D, the outer sheath 12 has been retracted until the outer sheath radiopaque marker 28 overlies the intraluminal device radiopaque markers 22 (i.e., until the delivery device 10 is ready to deploy the second intraluminal device 2). As shown in FIG. 10D, the first self-expanding intraluminal device 2 has expanded to be substantially apposed to the intraluminal wall. During deployment of the individual self-expanding implants (e.g., intraluminal devices 2), the expansion filaments 1910 can be completely contained within the pockets/filament recesses 1820 and the inner core wall.

Once the intraluminal device 2 has been deployed to its target location and stopped expanding within the vessel (i.e., no more or very little motion of the intraluminal device radiopaque markers 22 is observed), the delivery device 10 is moved either proximally or distally and repositioned such that the post deployment dilation device is moved underneath the intraluminal device 2, shown in FIG. 10E. In this position, the centers of the exposed expansion filaments 1910 are located at the approximate center of the deployed intraluminal device 2.

Radiopaque markers, e.g., distal radiopaque ring 1720 and proximal radiopaque ring 1722 may be used to align the post deployment dilation device with the intraluminal device 2. In some embodiments, the distal radiopaque ring 1720 and the proximal radiopaque ring 1722 are used to align the intraluminal device 2 in the center of the post deployment dilation device. In other embodiments, the proximal radiopaque ring 1722 is positioned closer to the intraluminal device radiopaque markers 22 of the intraluminal device 2 (shown in FIG. 10E). Placing the proximal radiopaque ring 1722 closer to the intraluminal device radiopaque markers 22 may be useful because the post deployment dilation device's largest deployment diameter is biased toward the proximal radiopaque ring 1722 (by contrast to the systems shown in FIG. 8). As the sliding sleeve 1920 moves proximally, the deployment diameter increases. Consequently, the user may advance or retract the delivery device 10 until the intraluminal device radiopaque markers 22 lie just distal of the proximal radiopaque ring 1722. At that point, the intraluminal device 2 may be located where the deployment diameter is sufficiently large for the intraluminal device 2—the proper location for activation of the post deployment dilation device.

When the post deployment dilation device is located in the desired position under the intraluminal device 2, the expansion mechanism may be activated by proximal movement (such as pulling proximally on) of the retractor, e.g., expansion control 1730. As described above, this causes the sliding sleeve 1920 to slide proximally and the expansion filament 1910 to radially expand outwards, as shown in FIG. 10E. The radial expansion of the expansion filaments 1910, or "buckling," causes the expansion filaments 1910 to engage with the inner surface of the intraluminal device 2, as shown in FIG. 10E. As the expansion filaments 1910 continue to expand radially, they continue to push radially outward on the inner surface of the intraluminal device 2, thereby fully dilating the deployed intraluminal device 2 against the inner wall of the vessel.

Following radial expansion of the expansion filaments 1910 and complete deployment of the intraluminal device 2, the expansion mechanism can be deactivated by pushing distally on the retractor, e.g., inducing distal movement of the expansion control 1730, e.g., at or in the proximal region 6 of the delivery device 10. As described above, this causes each expansion filament 1910 to retract back into its distal sectioned pocket or filament recess 1820, to once again lie flat against the inner shaft 26.

While the post deployment dilation device shown in FIGS. 10A-10F was described as being located at or in the distal region 4 of the delivery device 10, between the nose cone 38 and the distal-most intraluminal device 2, it should be understood that a plurality of such post deployment dilation devices may be included in the delivery device 10. For example, one post deployment dilation device (e.g., sliding sleeve 1920 and plurality of expansion filaments 1910) may be incorporated under each intraluminal device 2, e.g., into the platform underlying the intraluminal device 2. In such embodiments, each post deployment dilation device may have controls accessible at or in the proximal region 6 of the delivery device 10. Therefore, a user may retract the outer sheath 12 to deploy an intraluminal device 2, and, without moving the delivery device 10, activate the post deployment dilation device underlying the intraluminal device 2 to post-dilate the intraluminal device 2.

FIGS. 11A-11F illustrate a delivery device 10 having a post deployment dilation device incorporating a pre-formed expandable frame. The frame can be a bellow 2010. This delivery device 10 is very similar to the delivery device 10 of FIGS. 10A-10G. However, whereas the post deployment dilation device shown in FIG. 10 incorporates a plurality of expansion filaments 1910 attached to a sliding sleeve 1920, the post deployment dilation device of FIG. 11 incorporates the expandable bellows 2010 attached to a sliding ring or sleeve 2020 (similar to the sliding sleeve 1920).

FIGS. 11A-11C show the post deployment dilation device in various stages of deployment: FIG. 11A illustrates the post deployment dilation device in a pre-deployment state (i.e., fully collapsed); FIG. 11B illustrates the post deployment dilation device in a state of partial deployment; and FIG. 11C illustrates the post deployment dilation device in a state of substantially full deployment.

The post deployment dilation device generally includes a bellow 2010. The proximal end region of the bellow 2010 is generally attached to the inner shaft 26 near or at the proximal end region of the post deployment dilation device's platform. The distal end region of the bellow 2010 is attached to a sliding sleeve or ring 2020. The sliding sleeve 2020 may be operatively coupled to an expansion control 1730 or retractor at or in the proximal region 6 of the delivery device 10. The retractor or expansion control 1730 allows a user to cause the sliding sleeve 2020 to slide, coaxially, along the inner shaft 26. In some embodiments, the retractor or expansion control 1730 is simply a series of filaments attached to the sliding sleeve 2020, extending over the surface of the post deployment dilation device's platform, into the wall of the inner shaft 26 (e.g., through filament lumens 1810), and to the proximal region 6 of the delivery device 10.

The sliding sleeve 2020 may be positioned in its relative "home" position (e.g., near the distal radiopaque ring 1720), shown in FIG. 11A. In some embodiments, some axial force is necessary to hold the sliding sleeve 2020 in its distal-most position. In such embodiments, the retractor or expansion control 1730 may be used to provide such an axial force in the distal direction. In the post deployment dilation device's undeployed state, when the sliding sleeve 2020 lies in its "home" position, the bellow 2010 lies substantially flat against the post deployment dilation device's platform.

In operation, the retractor or expansion control 1730 may be moved proximally, thereby causing the sliding sleeve 2020 to slide proximally along the surface of the inner shaft 26. In some embodiments, the retractor or expansion control 1730 is pulled proximally. However, in other embodiments, the axial force in the distal direction is merely decreased to allow the retractor or expansion control 1730 to move proximally. FIG. 11B shows a sliding sleeve 2020 that has been slid partially in the proximal direction. FIG. 11C shows a sliding sleeve 2020 that has been slid even further in the proximal direction. Sliding the sliding sleeve 2020 proximally, towards the bellow's 2010 point of attachment to the inner shaft 26, causes the bellow 2010 to accordion. As the bellow 2010 accordions, it will move from a substantially straight, sheath-like configuration, to an accordion-like configuration having a plurality of bellow recesses 2012 and a plurality of bellow ridges 2014 having a bellow diameter 2030. As can be seen with reference to FIGS. 11B and 11C, the bellow diameter 2030 is controlled by the longitudinal displacement of the sliding sleeve 2020. That is to say that as the sliding sleeve 2020 moves even further proximally, the bellow 2010 will accordion even more, causing the bellow diameter 2030 to increase even further. The bellow 2010 can be made of a number of filaments formed into a frame with a cover to create the bellow recesses 2012 and bellow ridges 2014. For example, the filament can be wound in a helical configuration. The frame can be moved so that one end region is moved closer to the other to expand the bellows 2010.

FIGS. 11D-11F illustrate a method of using the post deployment dilation device just discussed. The method is substantially the same as the method described with respect to FIGS. 10D-10F. In short, an intraluminal device 2 is deployed in the vasculature, then one or more radiopaque markers are used in concert with the intraluminal device radiopaque markers 22 of the intraluminal device 2 to align the post deployment dilation device with the intraluminal device 2. Once the intraluminal device 2 is aligned with the post deployment dilation device as desired, the post deployment dilation device is activated by using the retractor or expansion control 1730 to move the sliding sleeve 2020 in the proximal direction. As the sliding sleeve 2020 moves, the bellow 2010 accordions and increases its bellow diameter 2030 such that the bellow ridge 2014 contact the inner surface of the intraluminal device 2. As the bellow 2010 continues to expand radially (i.e., the bellow diameter 2030 continues to increase), it continues to push radially outward on the inner surface of the intraluminal device 2, thereby fully dilating the deployed intraluminal device 2 against the inner wall of the vessel.

While the post deployment dilation device shown in FIGS. 11A-11F was described as being located at or in the distal region 4 of the delivery device 10, between the nose cone 38 and the distal-most intraluminal device 2, it should be understood that the post deployment dilation device can be placed elsewhere on the delivery device (e.g., proximal to the delivery platform(s) 8) and that a plurality of such post deployment dilation device may be included in the delivery device 10. For example, one post deployment dilation device (e.g., bellow 2010) may be incorporated under each intraluminal device 2, e.g., into the delivery platform 8 underlying the intraluminal device 2. In such embodiments, each post deployment dilation device may have controls accessible at or in the proximal region 6 of the delivery device 10. Therefore, a user may retract the outer sheath 12 to deploy an intraluminal device 2, and, without moving the delivery device 10, activate the post deployment dilation device underlying the intraluminal device 2 to post-dilate the intraluminal device 2. However, it should be understood that the post deployment dilation device can be placed on the outer sheath 12 using similar construction principles.

Figure 12G:
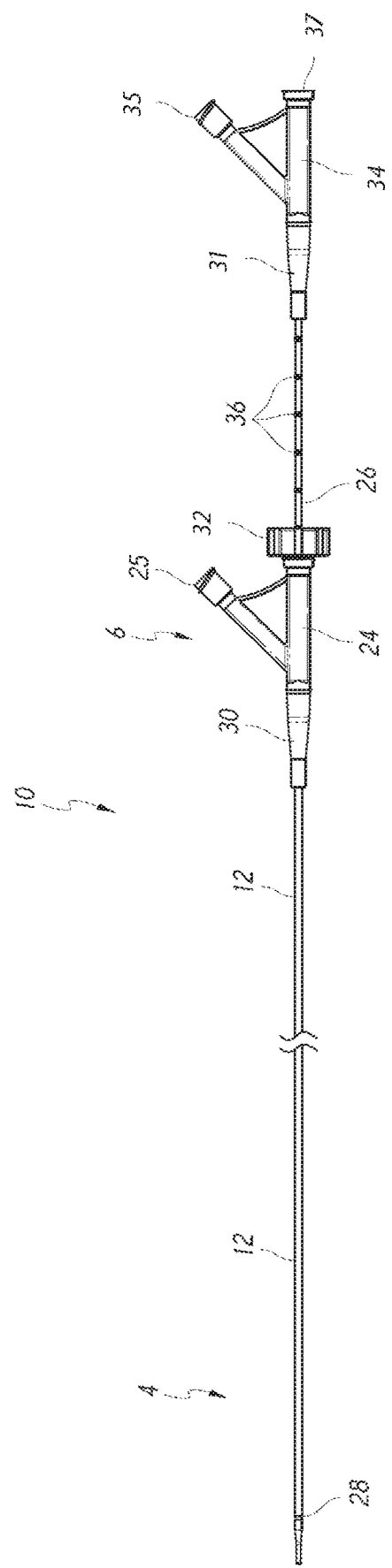
FIG. 12G is a side view of a delivery device that has been shortened to facilitate illustration, with a post deployment dilation device comprising an inner core balloon.

FIGS. 12A-12G illustrate another embodiment of a delivery device 10 having a post deployment dilation device incorporating an inner core balloon 2110. FIGS. 12A-12C show the post deployment dilation device in various stages of deployment: FIG. 12A illustrates the post deployment dilation device in a pre-deployment state (i.e., fully collapsed); FIG. 12B illustrates the post deployment dilation device in a state of partial deployment (i.e., only partially inflated); and FIG. 12C illustrates the post deployment dilation device in a state of substantially full deployment (i.e., fully inflated). FIG. 12G illustrates a shortened version of the delivery device 10 with one possible proximal adapter that may be configured to allow for inner core balloon 2110 inflation.

The post deployment dilation device can include a distal radiopaque ring 1720, a proximal radiopaque ring 1722, and an inner core balloon 2110. Distal radiopaque ring 1720 and proximal radiopaque ring 1722 may be the same as has already been described with respect to FIG. 8. The inner core balloon 2110 may be constructed from a compliant elastic material, semi-compliant material, or non-compliant material (e.g., synthetic polyisoprene, silicone, nylon, polyethylene, polyurethane, or various blends of materials). The inner core balloon 2110 may be fluoroscopically located using the distal radiopaque ring 1720 and the proximal radiopaque ring 1722, or there can be one or more radiopaque markers (not shown) under the inner core balloon 2110, or any combination thereof.

The inner core balloon 2110 may extend from about the distal radiopaque ring 1720 or the distal end of the post deployment dilation device's platform to about the proximal radiopaque ring 1722 or the proximal end of the post deployment dilation device's platform. As illustrated in FIGS. 12A-2G, the inner core balloon 2110 can be placed on the inner core shaft (e.g., the inner shaft 26), distal to the intravascular implants 2. However, it should be understood that the inner core balloon 2110 can be placed elsewhere on the delivery device (e.g., proximal to the delivery platform(s) 8) and can be placed on the outer sheath 12 using similar construction principles as will be discussed.

In some embodiments, the inner core balloon 2110 has a pre-deployment diameter that is only marginally larger than the underlying portion of the inner shaft 26 and may be smaller in diameter than the nose cone 38. In such embodiments, the pre-deployment diameter is sufficiently small that the inner core balloon 2110 may reside between the inner shaft 26 and the outer sheath 12, e.g., the outer sheath 12 is movable over the inner core balloon 2110. In some embodiments, the inner core balloon 2110 may have an expanded working diameter of up to about 8 mm. In other embodiments, the inner core balloon 2110 has an expanded working diameter of about 0.4, 0.6, 0.8, 1, 1.2, 1.4, 1.6, 1.8, 2, 2.2, 2.4, 2.6, 2.8, 3, 3.2, 3.4, 3.6, 3.8, 4, 4.2, 4.4, 4.6, 4.8, 5, 5.2, 5.4, 5.6, 5.8, 6, 6.2, 6.4, 6.6, 6.8, 7, 7.2, 7.4, 7.6, 7.8, 8, 8.2, 8.4, 8.6, 8.8, 9, 9.2, 9.4, 9.6, 9.8, or 10 mm. In other embodiments, the 2110 has any other expanded working diameter that is appropriate for fully deploying a vascular device within a subject's vasculature.

Figure 13A:
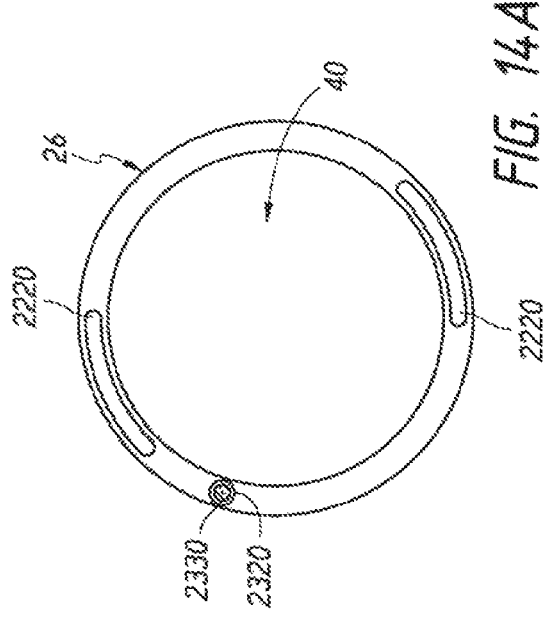
FIGS. 13A-13B show a cross section of an inner shaft having fluid lumens adapted to transmit fluid to/from an inner core balloon.
Figure 13B:
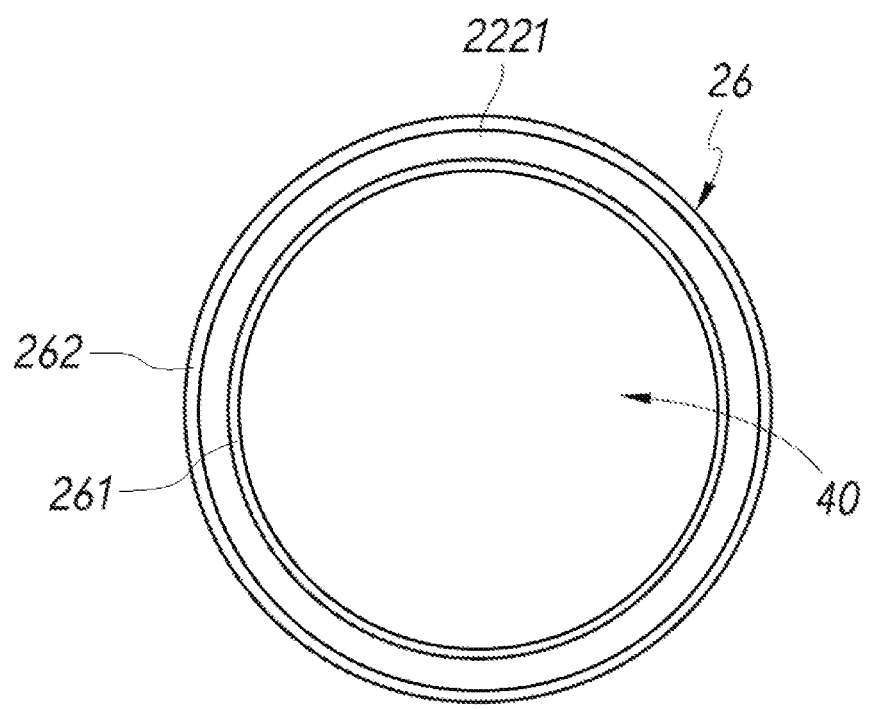

The inner core balloon 2110 can be inflated by a fluid transferred from an inflation port 35 on the proximal inner shaft housing 34 to the inner core balloon 2110 through one or more fluid lumens, e.g., lumens 2220, 2221. The proximal inner shaft housing 34 may have a guidewire port 37, which is in communication with the guidewire lumen 40. The proximal inner shaft housing 34 may also include an inner shaft strain relief 31. In some embodiments, the inner shaft 26 is formed to include one or more fluid lumens 2220 through which fluids may travel from one end of the delivery device 10 to the other. The inner shaft 26 may consist of a multi lumen tube as shown in FIG. 13A, which illustrates an inner shaft 26 having a guidewire lumen 40 at its center as well as two fluid lumens 2220 within its wall, substantially parallel to the guidewire lumen 40. Fluid (e.g., a gas or a liquid fluid) may be pumped from the proximal region 6 of the delivery device 10 to the distal region 6 of the delivery device 10. For example, fluid may be pumped from the proximal end of the delivery device 10 (e.g., inflation port 35) to the post deployment dilation device of FIGS. 12A-12G to inflate the inner core balloon 2110. Certain embodiments can include a coaxial tube system, an example of which is shown in FIG. 13B, rather than a multi-lumen tube, as discussed herein and shown in FIG. 13A. Coaxial tube systems may include multiple, coaxially arranged tubes, including, for example two or more coaxially arranged tubes as shown in the illustrated embodiment. In the illustrated embodiment, the outer tube 262 can extend over at least a portion of an inner tube 261. The inner tube 261 can define at least a portion of the guidewire lumen 40. At least a portion of the fluid lumen 2221 can be defined by an outer surface of the inner tube 261 and an inner surface of the outer tube 262. More than one coaxial fluid lumen may be formed by including more than two coaxially arranged tubes. For example, three tubes would define two fluid lumens and a guidewire lumen, which can be the central lumen. And, four tubes would define three fluid lumens and a guidewire lumen, which can be the central lumen. It will be understood that such multi-fluid lumen systems may be used to deliver different fluids to a single inflatable inner core balloon 2110, or they may be used to deliver the same fluid to multiple balloons, or they may be used to deliver different fluids to multiple balloons. The inner core balloon 2110 can be attached to such a coaxial tube system in several different manners. For example, in an embodiment, a distal region of the inner core balloon 2110 may be attached (in some embodiments with a fluid tight seal) to a distal region of the inner tube 261. A proximal region of the inner core balloon 2110 can be attached (in some embodiments with a fluid tight seal) to a distal region of the outer tube 262. In such a configuration, the inner tube 261 can form a guidewire lumen 40 which provides a passage for a guidewire 50, and the outer tube 262 can define an annular inflation fluid lumen 2221, which is in fluid communication with the interior of the inner core balloon 2110. The annular inflation fluid lumen 2221 can provide a passage for inflation fluid to inflate and deflate the inner core balloon 2110. In some embodiments, the outer tube 262 and the inner tube 261 are configured to move with respect to each other (e.g., telescope or rotate). For example, when the inner core balloon 2110 is in the deflated state (either pre- or post-inflation), the distance between where the inner core balloon 2110 is attached to the outer tube 262 and where it is attached to the inner tube 261 may be displaced longitudinally (e.g., moved apart or spaced a certain distance) such that the inner core balloon 2110 is stretched or held a position to enable a low, uninflated profile. Upon or during inflation of the inner core balloon 2110, the distance between where the inner core balloon 2110 is attached to the outer tube 262 and where it is attached to the inner tube 261 may be reduced compared to the uninflated state of the inner core balloon 2110. This can assist the inner core balloon 2110 in achieving the desired working diameter or working diameter range and/or maintain a low uninflated profile and easily be covered by the outer sheath 12 both pre-inflation and post-deflation. In some embodiments, when the inner core balloon 2110 is in the deflated state (pre-inflation or post-deflation), the respective rotational position between where the inner core balloon 2110 is attached to the outer tube 262 and where it is attached to the inner tube 261 changes (e.g., rotated by some angular amount). In this way, the inner core balloon 2110 is in effect twisted (e.g., about 45 degrees, about 90 degrees, about 180 degrees, about 360 degrees, about 540 degrees, or about 720 degrees) or held in a position to enable a low uninflated profile. Upon or during inflation of the inner core balloon 2110, the respective rotational position between where the inner core balloon 2110 is attached to the outer tube 262 and where it is attached to the inner tube 261 may remain the same or the rotation may be reduced (e.g., un-twisted or unwound) compared to the uninflated state. This can assist the inner core balloon 2110 in achieving the desired working diameter or working diameter range and/or maintain a low uninflated profile. Any combination of movement (e.g., displacement, rotation, etc.) can be used as well.

As will be readily understood, while two fluid lumens 2220 are shown, the inner shaft 26 may include only 1 fluid lumen 2220. In some embodiments, the inner shaft 26 include 3, 4, 5, 6, 7, or even 8 fluid lumens 2220. In other embodiments, the inner shaft 26 includes more than 8 fluid lumens 2220.

In operation, as shown in FIGS. 12A-12G with the outer sheath 12 retracted, fluid may be pumped into the inner core balloon 2110 through inflation port 35, e.g., from the proximal end of the delivery device 10, thereby causing the inner core balloon 2110 to inflate. Various amount of fluid pumped or injected into the inner core balloon 2110 can cause various amounts of radial pressure on the walls of the inner core balloon 2110. The amount of fluid pumped into the inner core balloon 2110 can affect the diameter of the inner core balloon 2110. When using a compliant inner core balloon 2110 material, increasing the amount of fluid within the inner core balloon 2110 may cause the inner core balloon 2110 to continue to expand (e.g., until it critically fails, or bursts). This enables the inner core balloon 2110 to be fully formed at one diameter (e.g., about 4 mm) allowing an intravascular device 2 to be substantially apposed to the intraluminal wall in a vessel having a first size (e.g., about 4 mm), while the same inner core balloon 2110 can be further inflated to a larger diameter (e.g., about 8 mm) allowing an intravascular device 2 to be substantially apposed to the intraluminal wall in a vessel having a second size (e.g., about 8 mm) different from the first size. This is beneficial in that both the intravascular devices 2 and the inner core balloon 2110 can be used in a wide range of vessel diameters without. In this way accurately pre-selecting the required diameter of intravascular device 2 and/or diameter of the inner core balloon 2110, as is common practice with current stents and dilation balloons (which have a more limited deployed and/or inflated working diameter range), might be advantageously avoided. In addition, given that the delivery device 10 can include multiple intravascular devices 2, it is even more beneficial to have an intravascular device 2 and an inner core balloon 2110 that can treat varying vessel diameters as not all intravascular devices 2 may be delivered to sites having the same diameter. In some embodiments, the delivery device 10 can have an inner core balloon 2110 with a working diameter range (e.g., usable over a range of pre-specified diameters) in the range of between about 2.5 mm to 6 mm, between about 4 mm to 8 mm, and between about 6 mm to 10 mm. In other embodiments, the inner core balloon 2110 may have other pre-specified working diameter ranges.

The compliance of the inner core balloon 2110 material may be selected to enable the inner core balloon 2110 to reach its full diameter at lower pressures than are typically used in or during a balloon angioplasty procedure. This is because high pressures may not be (e.g., generally are not) necessary to substantially or fully appose the intraluminal device 2 to the intraluminal wall. Lower pressures may be less traumatic to the vessel and may allow for the inner core balloon 2110 to be easily positioned within a deployed intraluminal device 2 for post deployment dilation, e.g., have a length that is advantageously longer than the intraluminal device 2. In a typical stent deployment, or post deployment stent dilation, the dilation balloon is inflated to high pressures. High inflation pressures may cause the ends of the stent and the vessel just beyond the stent may be over-dilated, thereby potentially damaging the vessel wall. Initial dilation and subsequent over-pressure/over-dilation of the vessel can cause dissections. If the intraluminal device 2 is being used to treat a dissection, it is generally advantageous to use as low a force as possible on the intraluminal device 2 and as low as possible pressure in the post deployment dilation device (e.g., balloons, bellows, filaments, etc.) to cause the intraluminal device 2 to be substantially apposed to the intraluminal wall, and thereby reduce the potential or risk of further damage to the vessel.

In balloon angioplasty with stent delivery, the dilation balloon working length is typically the same as the length of the stent; consequently, centering the balloon within the stent can be critical. With an inner core balloon 2110 that is fully dilated at a lower pressure, and a self-expanding intraluminal device 2 that can be substantially apposed to the intraluminal wall at or with low forces, there may be less concern for vessel damage (these pressures are typically below that originally used in the angioplasty balloon to dilate the vessel). The inner core balloon 2110 can reach its full diameter at for example 6 atmospheres, or lower pressures, such as about 1 atmosphere, about 2 atmospheres, about 3 atmospheres, about 4 atmospheres, or about 5 atmospheres. The inner core balloon 2110 may also reach its full diameter at higher pressures than 6 atmospheres.

FIG. 12A shows an inner core balloon 2110 in its pre-deployment state, almost completely collapsed against the inner shaft 26. Depending on the inner core balloon 2110 material, size, and configuration, the inner core balloon 2110 may be completely collapsed against the inner shaft 26. FIG. 12B shows an inner core balloon 2110 that has been only partially inflated. Finally, FIG. 12C shows an inner core balloon 2110 that has been inflated to a fully-formed (e.g., without notable folds or creases) diameter. In some embodiments, the inner core balloon 2110 may then be inflated further to increase the diameter of the inner core balloon 2110. Ultimately, expansion of the inner core balloon 2110 is controlled by the amount of fluid pumped into the inner core balloon 2110. In some embodiments, the delivery device 10 includes a pressure sensor capable of detecting the pressure within the inner core balloon 2110. In such embodiments, the pressure sensor may advantageously communicate with the pump, e.g., inflation device, (that is pumping the fluid from the proximal region 6 of the delivery device 10 into the inner core balloon 2110) such that the pump may automatically stop pumping before the burst pressure of the inner core balloon 2110 is reached. A pump can be manually operated, semi-automated, or fully-automated, and may include pressure and/or volume measurement or volume indicators such that a specific volume, diameter, or other metric of the inner core balloon 2110 can be reached. Additional diameters can be reached by changing the pressure/fluid volume within the inner core balloon 2110.

FIGS. 12D-12F illustrate a method of using the post deployment dilation device just discussed. In FIG. 12D, the outer sheath 12 has been retracted until the outer sheath radiopaque marker 28 overlies the intraluminal device radiopaque markers 22 (i.e., until the delivery device 10 is ready to deploy the second intraluminal device 2). As shown in FIG. 12D, the first self-expanding intraluminal device 2 has expanded to be substantially apposed to the intraluminal wall. During deployment of the individual self-expanding intraluminal devices 2, it may be desirable that the inner core balloon 2110 is deflated (e.g., partially, substantially, or completely deflated against the outer diameter of the inner shaft 26).

Once the intraluminal device 2 has been deployed to its target location and stopped expanding within the vessel (i.e., no more or very little motion of the intraluminal device radiopaque markers 22 is observed), the delivery device 10 is moved either proximally or distally and repositioned such that the post deployment dilation device is moved underneath the intraluminal device 2, shown in FIG. 12E with an inner core balloon 2110 that has been only partially inflated. In this position, the center of the inner core balloon 2110 is located at the approximate center of the deployed intraluminal device 2.

Radiopaque markers, e.g., distal radiopaque ring 1720 and proximal radiopaque ring 1722 may be used to align the post deployment dilation device with the intraluminal device 2, and/or one or more radiopaque markers under the inner core balloon 2110, as discussed previously. In some embodiments, the distal radiopaque ring 1720 and the proximal radiopaque ring 1722 are used to align the intraluminal device 2 at or near the center of the post deployment dilation device. In other embodiments, the proximal radiopaque ring 1722 is positioned closer to the radiopaque markers 22 of the intraluminal device 2. In other embodiments, one or more radiopaque markers (e.g., working length radiopaque markers or a central radiopaque marker) under the inner core balloon 2110 are used to align the intraluminal device 2 in the relative center of the post deployment dilation device.

When the post deployment dilation device is located in the desired position under the intraluminal device 2, the inner core balloon 2110 may be inflated by pumping fluid from the inflation port 35, e.g., through the one or more fluid lumens 2220, 2221, and into the inner core balloon 2110. As described above, this causes the inner core balloon 2110 to radially expand outwards, as shown in FIG. 12E (showing partial expansion) and FIG. 13E (showing further expansion). The radial expansion of the inner core balloon 2110 causes the outer surface of the inner core balloon 2110 to engage with the inner surface of the intraluminal device 2, as shown in FIG. 12E. As the inner core balloon 2110 continues to radially expand, it continues to push radially outward on the inner surface of the intraluminal device 2, thereby fully dilating the deployed intraluminal device 2 against the inner wall of the vessel. As discussed herein, an inner core balloon 2110 formed or constructed out of a compliant material can be expanded to a range of working diameters enabling a range of intraluminal device 2 working diameters to be achieved. Additionally, an inner core balloon 2110 formed or constructed out of a compliant material may allow some degree of longitudinal and or axial, e.g., rotational, movement of the inner tube 261 with respect to the outer tube 262.

Following radial expansion of the inner core balloon 2110 and complete deployment of the intraluminal device 2, the inner core balloon 2110 can be deflated, e.g., by removing the expansion fluid. In some embodiments, the expansion fluid is removed actively, such as by pumping the fluid out. In other embodiments, the expansion fluid is removed passively, such as by simply opening a purge valve and allowing the expansion fluid to flow out due to any pressure differential that exists. As described above, deflating the inner core balloon 2110 can cause the inner core balloon 2110 to recover (e.g., due to elastic properties of the inner core balloon 2110, preset folds, wall thickness variation, etc.) and to once again lie flat against the inner shaft 26 or at least have a reduced uninflated profile.

While the post deployment dilation device shown in FIGS. 12A-12F is described as being located at or in the distal region of the delivery device 10, between the nose cone 38 and the distal-most intraluminal device 2, it should be understood that the post deployment dilation device can be placed elsewhere on the delivery device (e.g., proximal to the delivery platform(s) 8) and that a plurality of such post deployment dilation devices may be included in the delivery device 10. For example, one post deployment dilation device (e.g., inner core balloon 2110) may be incorporated under each intraluminal device 2, e.g., into the delivery platform 8 underlying the intraluminal device 2. In such embodiments, each post deployment dilation device may have controls accessible at or in the proximal region 6 of the delivery device 10. Therefore, a user may retract the outer sheath 12 to deploy an intraluminal device 2, and, without moving the delivery device 10, activate the post deployment dilation device underlying the intraluminal device 2 to dilate the intraluminal device 2.

Figure 14B:
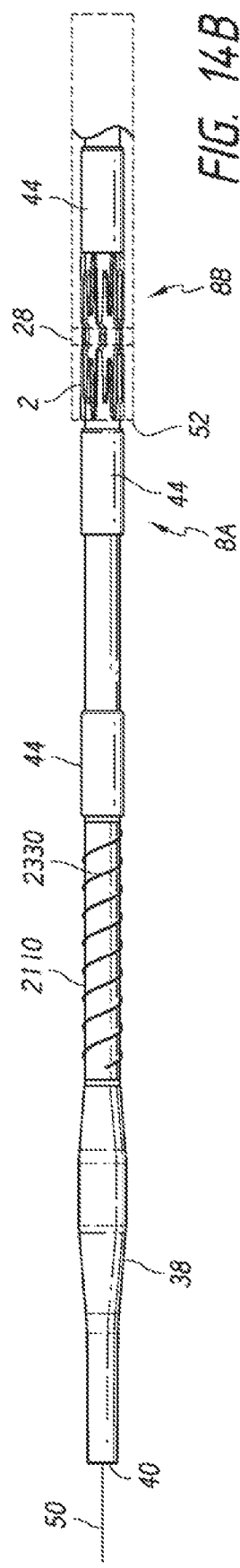

To help confine the inner core balloon 2110 against the inner shaft 26, both before and after use of the post deployment dilation device, a helical filament 2330 may be used. The helical filament 2330 may be an elongate filament having a distally located helical portion and a long, substantially straight, proximal portion. The helical portion of the helical filament 2330 need be helical only in the region of the inner core balloon 2110, as shown in FIG. 14B. The rest of the helical filament 2330 may be straight, extending back through the inner shaft 26 to the proximal region 6 of the delivery device 10.

FIG. 14A illustrates an inner shaft 26 which has been formed, e.g., extruded, to include multiple lumens, including a guidewire lumen 40 at its center, two fluid lumens 2220 and a helical filament lumen 2320 (shown containing the helical filament 2330). The helical filament 2330 may extend from the post deployment dilation device's platform all the way back to the proximal region 6 of the delivery device 10 through the helical filament lumen 2320. In an embodiment, a helical filament lumen 2320 can be included in the outer tube 262 of a coaxial tube system as discussed herein. In such an embodiment, the outer tube 262 can include the helical filament lumen 2320, both of which extend over a coaxially arranged inner tube 261. When using a coaxial tube system with a helical filament lumen 2320, the inner core balloon 2110 can be advantageously attached to the inner surface of the outer tube 262. In that way, the helical filament 2330 may easily and smoothly extend out of the helical filament lumen 2320 and over the inner core balloon 2110.

The helical filament 2330 is preferably made out of a flexible material or combination of materials that retains enough rigidity that it can regain its shape after deformation, as will be discussed below. In some embodiments, the helical filament 2330 is made out of a polymer. In other embodiments, the helical filament 2330 is made out of a metal, such as a super-elastic metal (e.g., nitinol). The helical filament 2330 may be coated to modify one or more properties of the underlying material, such as a coating to increase lubricity of the helical filament 2330 and thereby reduce friction during movement within the helical filament lumen 2320. Coating types may include but are not limited to hydrophilic, fluorinated polymer, and silicone-based.

In its pre-deployment state, shown in FIG. 14B, the helical filament 2330 is helically wound around the inner core balloon 2110. After the intraluminal device 2 has been deployed and the post deployment dilation device relatively or substantially centered under the deployed intraluminal device 2, the helical filament 2330 may be retracted from over the inner core balloon 2110 using one or more of a proximal pulling and a twisting motion to withdraw or retract the helical filament 2330 into the helical filament lumen 2320. As the helical filament 2330 is withdrawn or retracted into the helical filament lumen 2320, its helical portion will elastically deform. When the helical filament 2330 is fully withdrawn or retracted from over the inner core balloon 2110, the inner core balloon 2110 may be used as described above.

Following use of the inner core balloon 2110, the inner core balloon 2110 is deflated as described above. Then, the helical filament 2330 can be used to capture and contain the outer diameter of the post-deflated inner core balloon 2110 to minimize the inner core balloon 2110's uninflated profile, thereby mitigating potential interactions between an irregularly shaped post-deflated inner core balloon 2110 and deployed intraluminal devices 2 and the vessel. To re-capture the inner core balloon 2110, the helical filament 2330 is extended back out of the helical filament lumen 2320 using one or more of a distal pushing and a twisting motion. As the helical distal portion of the helical filament 2330 extends out of the helical filament lumen 2320, it regains its shape, due to its elastic properties, and helically wraps around the deflated inner core balloon 2110 to confine the inner core balloon 2110 and minimize its uninflated profile (shown in FIG. 14B). Some embodiments of the helical filament 2330 include a rounded, blunted, or atraumatically-shaped (e.g., looped) distal tip or distal region to prevent damaging, snagging, and/or catching on the material of the inner core balloon 2110.

After the helical filament 2330 has been extended back out of the helical filament lumen 2320, the delivery device 10 may be moved proximally or distally to post-dilate another intraluminal device 2. Because the helical filament 2330 confines the inner core balloon 2110, risk of interactions between the irregularly shaped post-deflated inner core balloon 2110 and other structures may be mitigated. Once the post deployment dilation device and inner core balloon 2110 have been position at a desired location relative to another implant (e.g., intraluminal device 2), the helical filament 2330 may be retracted into the helical filament lumen 2320 thereby allowing inflation of the inner core balloon 2110. This process may be repeated for successive post-dilations of multiple intraluminal devices 2.

In another embodiment, rather than retract the helical filament 2330, the helical filament 2330 can be advanced out of the helical filament lumen 2320 to increase its size. Alternatively, filling the inner core balloon 2110 with fluid can force the helical filament 2330 to expand with the inner core balloon 2110, pulling the helical filament 2330 out of the helical filament lumen 2320. Removing the fluid can allow the helical filament 2330 to cinch down on the inner core balloon 2110, retracting itself into the helical filament lumen 2320 as the inner core balloon 2110 decreases in size.

Figure 15A:
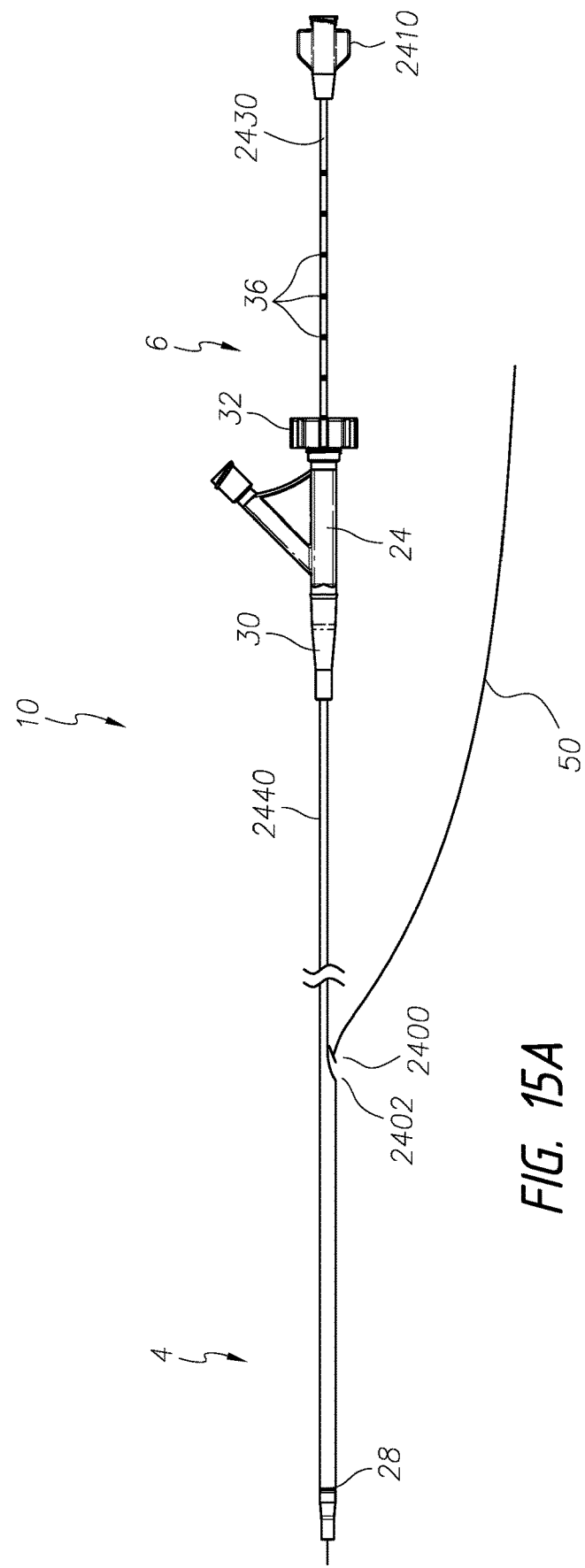
FIG. 15A is a side view of a delivery device that has been shortened to facilitate illustration, with a post deployment dilation device comprising an inner core balloon with a rapid exchange style configuration.

In another embodiment, the delivery device 10 can be of a rapid exchange style having a post deployment dilation device incorporating an inner core balloon 2110. That is, only a portion of the delivery device 10 rides on or over a guidewire 50. One embodiment of a rapid exchange style delivery device 10 is shown in FIG. 15. The rapid exchange style delivery device 10 may have apertures or ports, including, but not limited to, rapid exchange inner shaft guidewire port 2400 and rapid exchange outer sheath guidewire port 2402, which may allow the guidewire 50 to exit inner shaft 26 at a point distal to the proximal outer sheath housing 24. A rapid exchange proximal inner shaft 2430 may be attached to a rapid exchange proximal inflation port 2410. The delivery device 10 distal to the rapid exchange guidewire port 2400 may be similar to, or the same as, the delivery devices discussed elsewhere herein, e.g., in FIG. 2 and as described in connection therewith.

An enlarged view of the delivery device 10 region surrounding the rapid exchange guidewire ports is shown in FIG. 16A. FIGS. 16B-16C show cross sections of various portions of the delivery device 10 shown in FIG. 16A-FIG. 16B shows a cross section of the delivery device 10 of FIG. 16A taken along line 16B-16B and FIG. 16C shows a cross section of the same delivery device 10 taken along line 16C-16C. In FIG. 16A, a rapid exchange inner shaft guidewire port 2400 and a rapid exchange outer sheath guidewire port 2402 are shown slightly apart. These two ports can be close together or they can be separated by some distance. In some embodiments, the ports can be close together prior to delivery of intraluminal devices 2 and when the outer sheath 12 is retracted to deliver an intraluminal device 2, a portion of the outer sheath 12 distal to the rapid exchange outer sheath guidewire port 2402 will move over the guidewire 50 and rapid exchange proximal inner shaft 2430. In some embodiments, the rapid exchange outer sheath guidewire port 2402 can also be more proximal of the rapid exchange outer sheath guidewire port 2402 prior to delivery of any intraluminal devices 2.

In other embodiments, ports can be separated prior to delivery of intraluminal devices 2 by a distance equal to or greater than the distance the outer sheath 12 needs to be retracted to deliver all the intraluminal devices 2 contained in the delivery device 10. This could position a rapid exchange outer sheath guidewire port 2402 more distal than a rapid exchange inner shaft guidewire port 2400 prior to delivery of intraluminal devices 2. In this configuration, when the outer sheath 12 is retracted to deliver intraluminal devices 2, the portion of the outer sheath 12 distal to a rapid exchange outer sheath guidewire port 2402 will not move over the guidewire 50 and will only retract up to the region of a rapid exchange inner shaft guidewire port 2400.

In some embodiments, the distance between a rapid exchange inner shaft guidewire port 2400 and a rapid exchange outer sheath guidewire port 2402 prior to delivery of intraluminal devices 2 can be about equal to or less than about the distance the outer sheath 12 needs to be retracted to deliver all the intraluminal devices 2 contained in the delivery device 10. A rapid exchange inner shaft guidewire port 2400 and a rapid exchange outer sheath guidewire port 2402 can be identified by having one or more visual (e.g., colored band(s) or marking(s)) and/or radiopaque marker(s) or any combination thereof. Representative markers are shown as rapid exchange inner shaft guidewire port marker 2401 and rapid exchange outer sheath guidewire port marker 2404.

FIG. 16B shows an outer sheath 12 and a distal inner shaft 26. A distal inner shaft 26 is shown as a multi-lumen configuration with a guidewire lumen 40 and an inflation lumen 2220. FIG. 16C shows a rapid exchange proximal outer sheath shaft 2440 and a rapid exchange proximal inner shaft 2430. A rapid exchange proximal inner shaft 2430 contains a rapid exchange proximal inflation lumen 2420, which may be used to deliver inflation fluid from a rapid exchange inflation port 2410 (shown in FIG. 15), through the rapid exchange proximal inflation lumen 2420 and a distal inner shaft 26 fluid lumen 2220, and to an inner core balloon 2110. As described, a distal inner shaft 26 can also be of a coaxial configuration with the rapid exchange inflation port 2410 in fluid communication with the rapid exchange proximal inflation lumen 2420, a distal inner shaft 26 fluid lumen 2220, and an inner core balloon 2110. The profile of the outside of the rapid exchange inner shaft 2430 and the inside of the rapid exchange proximal outer sheath shaft 2440 may shapes other than round, e.g., "D" shaped as shown in FIG. 16D, so as to advantageously resist rotational movement of the two shafts with respect to each other, but not to resist longitudinal movement, thereby keeping the rapid exchange inner shaft guidewire port 2400 in sufficient radial alignment with the rapid exchange outer sheath guidewire port 2402.

FIGS. 17 and 18 illustrate another embodiment of a delivery device 10 having a post deployment dilation device incorporating an outer sheath balloon 2500. The delivery device 10 of FIG. 17, which has been shortened to facilitate illustration, highlights the distal region 4 and proximal region 6. FIG. 18 shows the distal region 4 with six intraluminal devices 2, each positioned at a dedicated or separate delivery platform 8. Comparing FIGS. 17 and 18, it can be seen that outer sheath 12 has been retracted (FIG. 18) from a more distal position (FIG. 17). This reveals/uncovers/exposes the delivery platforms 8 and their respective intraluminal devices 2. Both FIGS. 17 and 18 show an outer sheath balloon 2500.

An outer sheath balloon 2500 may be incorporated in a distal region 4 of the outer sheath 12. The outer sheath balloon 2500 may be constructed with some or all the properties and benefits discussed herein with respect to an inner core balloon 2110. The outer sheath 12 can contain one or more inflation lumens in configurations similar to those described in connection with FIGS. 13A-B and FIG. 14A.

Figure 15B:
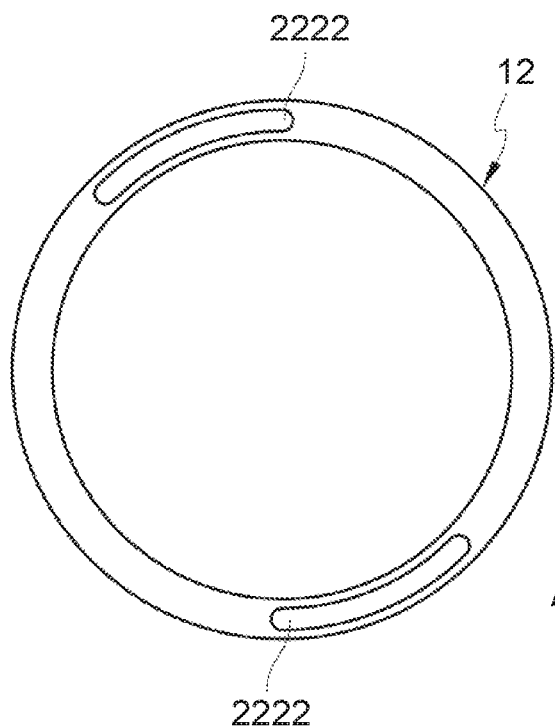
FIGS. 15B-15C show a cross section of an outer sheath having fluid lumens adapted to transmit fluid to/from an outer sheath balloon.
Figure 15C:
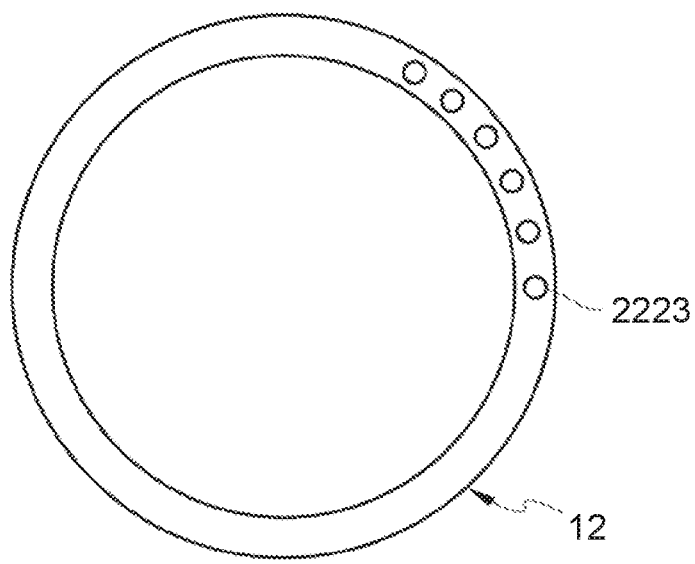

One of ordinary skill in the art will understand that many variations of possible inflation lumens in the outer sheath 12 exist. Various examples of such inflation lumens in a representative outer sheath 12 are shown in FIGS. 15B-15C. FIG. 15B shows an outer sheath 12 (with internal components, e.g., inner shaft 26, intraluminal devices, etc., removed for ease of explanation and illustration) having two oblong outer sheath inflation lumens 2222. The two outer sheath inflation lumens 2222 shown in FIG. 15B are oblong, but they may have other shapes. While FIG. 15B illustrates only two oblong outer sheath inflation lumens 2222, it may have only one oblong outer sheath inflation lumens 2222 or it may have three, four, five, six, or more oblong outer sheath inflation lumens 2222. The oblong outer sheath inflation lumens 2222 may be spaced evenly about the outer sheath 12, or they may be grouped (e.g., on one side, or together). FIG. 15C illustrates an outer sheath 12 (with internal components, e.g., inner shaft 26, intraluminal devices, etc., removed for ease of explanation and illustration) having six circular outer sheath inflation lumens 2223. It will be readily understood that the circular outer sheath inflation lumens 2223 may be grouped on one side of the outer sheath 12 or they may be spaced about the outer sheath 12. The number of circular outer sheath inflation lumens 2223 may be increased or decreased. For example, the outer sheath 12 may have 1 circular outer sheath inflation lumen 2223, or the outer sheath 12 may have 2, 3, 4, 5, 6, 7, 8, 9, 10, 11, 12, 13, 14, 15, or more circular outer sheath inflation lumens 2223. One of ordinary skill in the art will understand that the number, shape, and position of outer sheath inflation lumens may be changed as needed.

One or more outer sheath inflation lumen(s) can be in fluid communication with an outer sheath balloon inflation port 341 in a proximal outer sheath housing 241 and used to inflate the outer sheath balloon 2500. Expansion of the outer sheath balloon 2500 may be controlled by the amount or volume of fluid pumped into the outer sheath balloon 2500, e.g., through the outer sheath balloon inflation port 341. In some embodiments, as discussed previously, the delivery device 10 includes a pressure sensor capable of detecting the pressure within outer sheath balloon 2500. The pressure sensor may advantageously communicate with the pump, or other inflation device, that is pumping the fluid from the proximal region 6 of the delivery device 10 into outer sheath balloon 2500 such that the pump may automatically stop pumping before the outer sheath balloon 2500 reaches its burst pressure and/or a set fluid volume is delivered. A pump can be manual, semi-automated, or fully-automated and may include volume measurement or volume indicators such that a specific working diameter of the outer sheath balloon 2500 can be reached or achieved. Additional working diameters can be reached by changing the pressure within the balloon and/or fluid volume in the balloon. An outer sheath balloon 2500 may be fluoroscopically located using one or more radiopaque markers adjacent the outer sheath balloon 2500, such as an outer sheath balloon distal radiopaque marker 2520 and/or an outer sheath balloon proximal radiopaque marker 2522, or one or more radiopaque markers located under the outer sheath balloon 2500 (e.g., working length radiopaque markers or a central radiopaque marker), or any combination thereof.

In some embodiments, an outer sheath 12 can be constructed with coaxial tubes, e.g., outer sheath inner tube and outer sheath outer tube (not shown), that can be configured to move with respect to each other (e.g., telescope). For example, when the outer sheath balloon 2500 is deflated (e.g., pre-inflation or post-deflation), the distance between where the outer sheath balloon 2500 is attached to an outer sheath outer tube and where it is attached to the outer sheath inner tube may increase (e.g., moved apart or spaced a certain distance) such that the outer sheath balloon 2500 is stretched or held a position to enable a low, uninflated profile. Upon or during inflation of the outer sheath balloon 2500, the distance between where the outer sheath balloon 2500 is attached to the outer sheath outer tube and where it is attached to the outer sheath inner tube may be comparatively reduced. In some embodiments, when the outer sheath balloon 2500 is in its deflated state (pre-inflation or post-deflation), the rotational position between where the outer sheath balloon 2500 is attached to the outer sheath outer tube and where it is attached to the outer sheath inner tube changes (e.g., rotated some angular amount). In this way, the outer sheath balloon 2500 is, in effect, twisted (e.g., about 45 degrees, about 90 degrees, about 180 degrees, about 360 degrees, about 540 degrees, or about 720 degrees) or held in a position to enable a low uninflated profile. Upon or during inflation of the outer sheath balloon 2500, the respective rotational position between where the outer sheath balloon 2500 is attached to the outer sheath outer tube and where it is attached to the outer sheath inner tube may remain the same or the rotation may be reduced (e.g., un-twisted or unwound) compared to the uninflated state. This can assist the outer sheath balloon 2500 in achieving the desired working diameter or working diameter range and/or maintain a low uninflated profile. Any combination of movement (e.g., displacement, rotation, etc.) can be used as well.

The method of using the delivery device 10 incorporating an outer sheath balloon 2500 is similar to that discussed previously and as depicted in FIGS. 12A-G. Post deployment of the intraluminal device 2, and location and alignment of the outer sheath balloon 2500 with respect to the intraluminal device 2 can be accomplished using an outer sheath balloon distal radiopaque marker 2520 and an outer sheath balloon proximal radiopaque marker 2522, which function similarly to a distal radiopaque ring 1720 and proximal radiopaque ring 1722, and/or by using one or more radiopaque markers under the outer sheath balloon 2500 (e.g., working length radiopaque markers or a central radiopaque marker), or any combination thereof.

When the post deployment dilation device is located in the desired position under the intraluminal device 2, the outer sheath balloon 2500 may be inflated by pumping fluid from an outer sheath balloon inflation port 341 through the one or more fluid lumens, and into the outer sheath balloon 2500. As described above with reference to an inner core balloon 2110, this causes the outer sheath balloon 2500 to radially expand outwards. The radial expansion of the outer sheath balloon 2500 may cause an outer surface of the outer sheath balloon 2500 to engage an inner surface of the intraluminal device 2. As outer sheath balloon 2500 continues to radially expand, it continues to push radially outward on the inner surface of the intraluminal device 2, thereby causing the intraluminal device 2 to expand and substantially appose the intraluminal wall. As discussed elsewhere herein, when a compliant material is used to construct the outer sheath balloon 2500, the outer sheath balloon 2500 can be expanded throughout a range of working diameters enabling a range of intraluminal device 2 working diameters or diameters of full implant apposition to be achieved. In some embodiments, at least some portion an outer sheath outer tube and an outer sheath inner tube may be movable with respect to each other.

Following radial expansion of the outer sheath balloon 2500 and deployment of the intraluminal device 2, the outer sheath balloon 2500 may be deflated, e.g., by removing the expansion fluid. In some embodiments, as discussed previously, an outer sheath outer tube and an outer sheath inner tube may be moved. In some embodiments, the expansion fluid is removed actively, such as by pumping the fluid out. In other embodiments, the expansion fluid is removed passively, such as by simply opening a purge valve and allowing the expansion to flow out due to any pressure differential that exists. Deflating the outer sheath balloon 2500 can cause the outer sheath balloon 2500 to recover (e.g., due to elastic properties of the outer sheath balloon 2500, preset folds, wall thickness variation, etc.). Alternatively and or additionally, moving the outer sheath inner shaft and/or outer sheath outer shaft, e.g., telescoping the two with respect to each other, may help reduced uninflated profile of the outer sheath balloon 2500. One or more intraluminal device 2 dilations or deployments and then dilations may be conducted.

FIGS. 19 and 20 illustrate another embodiment of a delivery device 10 of a rapid exchange style having a post deployment dilation device incorporating an outer sheath balloon 2500. The delivery device 10 of FIG. 19, which has been shortened to facilitate illustration, highlights the distal region 4 and proximal region 6. FIG. 20 shows the distal region 4 with six intraluminal devices 2, each positioned at a dedicated or separate delivery platform 8. Comparing FIGS. 19 and 20, it can be seen that an outer sheath 12 has been withdrawn from a more distal position in FIG. 20. This reveals/uncovers/exposes the delivery platforms 8 and the respective intraluminal devices 2. Both FIGS. 19 and 20 show an outer sheath balloon 2500.

The inner shaft 26 may incorporate an aperture or port such as a rapid exchange inner shaft guidewire port 2400. The outer sheath 12 may contain one or more inflation lumens, e.g., of a multi-lumen, coaxial, or other design, which can be in fluid communication with an outer sheath balloon inflation port 341 and enable fluid transfer to and from the outer sheath balloon 2500. Outer sheath 12 can have an aperture or port such as a rapid exchange outer sheath guidewire port 2402 through which a guidewire 50 can pass. The outer sheath 12 can have different diameters along its length. For example, the proximal region 6 may have a section of outer sheath 12 that is smaller in diameter than a section of outer sheath 12 in a distal region 4.

In some embodiments, a helical filament 2330 may be used to constrain the outer sheath balloon 2500, similar to the helical filament described with respect to inner core balloon 211.

FIGS. 21A-21B show cross sections of an embodiment of an intraluminal device deployment mechanism. The deployment mechanism enables a user to deploy one intraluminal device 2 at a time. The deployment mechanism can include a deployment housing 3000 and may function in conjunction with the proximal outer sheath housing with mechanism 3010, which may be similar in one or more aspects to the proximal outer sheath housing 24 or proximal outer sheath housing 241. The proximal outer sheath housing with mechanism 3010 may be directly or indirectly connected to the outer sheath 12. The deployment housing 3000 is configured to be moved in general along the longitudinal axis of the inner shaft extension 3050, e.g., the distance that the outer sheath 12 must be retracted or withdrawn to deliver one intraluminal device 2. To move the deployment housing 3000 in the proximal direction (e.g., which may be a step in preparing the deployment mechanism for an intraluminal device 2 deployment), the release 3020 is depressed against the spring 3070, which disengages the lock 3080 and the deployment housing engagement 3030 from the inner shaft extension engagement 3040. The inner shaft extension engagement 3040 is part of or operates with the inner shaft 26 or inner shaft extension 3050. The deployment housing 3000 and internal components are then moved proximally the deployment distance 3060 as shown in FIG. 21A. Releasing the release 3020 re-engages the deployment housing engagement 3030 with the inner shaft extension engagement 3040. The deployment housing 3000 is then held stationary, e.g., held by the user, while the proximal outer sheath housing with mechanism 3010 is retracted, as shown in FIG. 21B, deploying one intraluminal device 2. When the final intraluminal device is deployed, the inner shaft extension 3050 can stop when the inner shaft strain relief 31 or other strain relief or housing as previously described (e.g., inflation port 35, rapid exchange proximal inner shaft hub 2450) meets the deployment housing 3000, some other stop, or simply not have a final stop.

FIGS. 21A-21B show the deployment mechanism configured for deployment of five intraluminal devices 2, e.g., the deployment mechanism comprises five inner shaft extension engagements 3040. It should be understood that the deployment mechanism can be configured to deploy any number of intraluminal devices by changing the number of inner shaft extension engagements 3040. Preferred number of intraluminal devices 2 on the delivery device 10 may be 4, 5, 6, 7, 8, 9, 10, 11, 12, 13, 14, 15, or more than 15 or less than 4 intraluminal devices 2. The inner shaft 26 or inner shaft extension 3050 can be fluid sealed with the proximal outer sheath housing with mechanism 3010, for example, using a seal 3090.

FIGS. 22A-22B show sectional views of an alternative release engagement. In some embodiments, the release 3020 has a release slot 3110 that, when depressed (as shown in FIG. 22A) against the spring 3070, allows proximal movement of the deployment housing 3000 without moving the inner shaft extension 3050 as the inner shaft extension 3050 slides/moves/translates through the release slot 3110. Releasing the release 3020 re-engages the release 3020 with the inner shaft extension engagement 3040. The deployment housing 3000 may then be held by the user while the proximal outer sheath housing with mechanism 3010 is retracted, thereby deploying one intraluminal device 2. The spring 3070 may be held in place, for example, by a spring retainer 3100.

Figure 23:
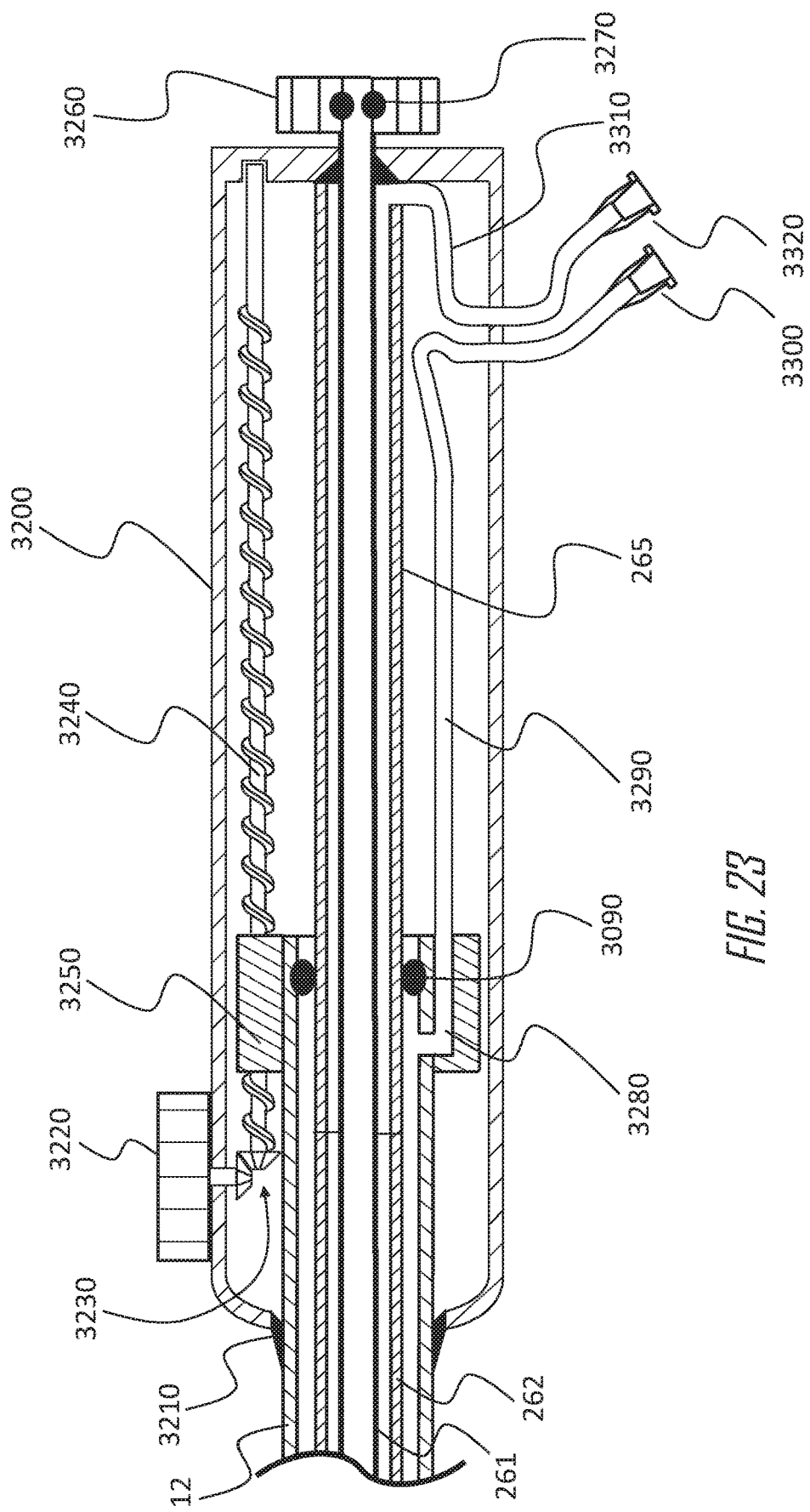
FIG. 23 shows a cross sectional view of an intraluminal device deployment mechanism.

FIG. 23 shows a deployment mechanism, including, for example, a handle, that may be used as part of the delivery device 10. FIG. 23 shows a handle with a coaxial inner shaft 26 arranged for incorporation of a post deployment dilation device incorporating an inner core balloon 2110. Similar handle configurations may be used with a multi-lumen outer shaft 12, with a rapid exchange style, and with or without a post deployment dilation device. In some embodiments, the deployment mechanism can have an actuator 3220, such as a slide, trigger, button, knob, thumbwheel, or any rotatory or linear based control, which directly or indirectly moves (e.g., retracts) the outer sheath 12 with respect to the inner shaft 26 to deploy one or more intraluminal devices 2. This may be accomplished, for example, by linear drive(s), screw(s), rack(s), gear(s), pull wire(s) or pull element(s), pulley(s), etc. or any combination thereof. For example, the actuator 3220 may be attached to an outer sheath drive engagement 3250, directly or through one or more intermediary components such as a drive engagement 3230, which has a drive 3240. For example, one rotation of the actuator 3220 (or more than one rotation or less than one rotation) retracts the outer sheath 12 the required distance to deploy one intraluminal device 2. The actuator 3220 may have one or more priority positions, for example, half of one rotation of the actuator 3220 may be the optimum position for the initial part of the deployment of an intraluminal device 2 with an indicator (e.g., tactile and/or visual indication to the user) at that location, while continuing to one full rotation may complete deployment of the intraluminal device 2, which may also serve as the starting position for deployment of the next intraluminal device 2, with an indicator.

As shown in FIG. 23, a coaxial configuration with a post deployment dilation device, the inner tube or shaft 261 may be coaxial with the outer tube 262. The configuration of the inner shaft 261 may also be of a multi-lumen or rapid exchange configuration as discussed herein. The outer tube 262 may have an outer tube handle extension 265. Such an outer tube handle extension 265 may be made from a material that is more rigid than the outer tube 262 (e.g., a metal) and configured to provide a better sealing surface with the seal 3090. There can be a handle seal 3210 that works with the handle housing 3200 and reduces or eliminates liquids, debris, or unwanted contaminants (e.g., blood, saline, dirt, etc.) from entering the handle, both when in a stationary position and when the outer sheath 12 is moved with respect to the outer tube 262 or the inner shaft 261. The area between the outer sheath 12 and the outer tube 262 or inner shaft 261 may be flushed to maintain lubricity and reduce or eliminate air and/or blood from entering the area. Fluid(s) may be introduced to this area from an outer sheath flush fitting 3300, through an outer sheath flush tube 3290 and into the outer sheath flush lumen 3280. Any pathway to provide fluid to this area is anticipated. To seal the inflation lumen against the guidewire 50, a guidewire seal knob 3260 may be used to compress a guidewire seal 3270, such as by rotation of the guidewire seal knob 3260. An inner core balloon 2110 can be inflated by a fluid transferred from an inflation lumen fitting 3320 to the inner core balloon 2110 through one or more inflation lumen tube(s) 3310 and/or channels as discussed herein. The handle may incorporate a strain relief similar to those discussed herein.

Figure 24:
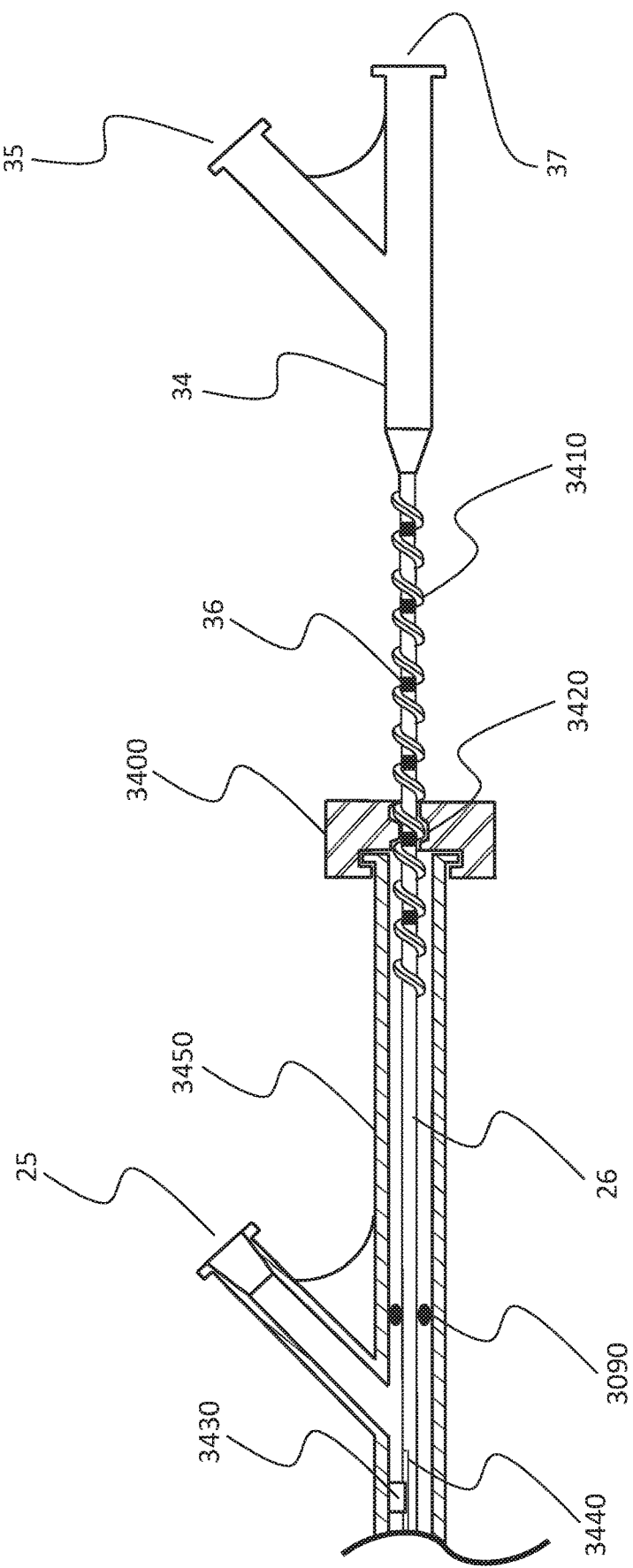
FIG. 24 shows a partial cross sectional view of a delivery device and deployment mechanism.

FIG. 24 is a similar delivery device 10 as shown in FIG. 12G, with the inclusion of a deployment mechanism. In some embodiments, the inner shaft 26 may have a region, e.g., inner shaft threaded extension 3410, which engages with the retraction actuator threads 3420 of the retraction actuator 3400 to retract the outer sheath 12 with respect to the inner shaft 26 when the retraction actuator 3400 is rotated. As shown in this example, each 360° rotation of the retraction actuator 3400 retracts the inner shaft 26 approximately one half the length of a delivery platform 8. A discussed herein, this allows one rotation to prepare the intraluminal device 2 for delivery, and a second rotation to complete the delivery of the intraluminal device 2. A detent, not shown, may be used to provide tactile feedback and/or a stopping point at each rotation, or each part of a rotation, of the rotation actuator 3400 with respect to the proximal outer sheath housing with rotation actuator 3450. To maintain rotational alignment between the proximal inner shaft housing 34 and the proximal outer sheath housing with rotation actuator 3450, an anti-rotation guide 3430 and corresponding anti-rotation guide engagement 3440 may be used. These can be any number of constructions, such as a tongue and groove, conformal shapes, a flat on the inner shaft 26, any construction that maintains relative rotational alignment between the proximal inner shaft housing 34 and the proximal outer sheath housing with rotation actuator 3450 when rotating the rotation actuator 3400. To re-sheath the inner shaft 26 with the outer sheath 12, the rotation actuator 3400 may be rotated in the opposite direction that it is rotated for deployment. The deployment mechanism shown in FIG. 24 may be easily adaptable to any and all discussed configurations with and without post deployment dilation devices and/or helical filament 2330.

In some embodiments, any of the deployment mechanisms discussed herein may have or incorporate a counter, position indicator, indicator, or display configured to show the number of intraluminal devices 2 delivered, to show the number of intraluminal devices 2 remaining, or any combination thereof.

In some embodiments, any of the deployment mechanisms discussed herein are an integrated part of the device (e.g., permanently attached to the device). In some embodiments, any of the deployment mechanisms discussed herein are a separate component(s) which is attached pre-procedure or during the procedure and may be reversibly attached, or stand alone and may be used adjacent the delivery device 10.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

The foregoing description and examples has been set forth merely to illustrate the disclosure and are not intended as being limiting. Each of the disclosed aspects and embodiments of the present disclosure may be considered individually or in combination with other aspects, embodiments, and variations of the disclosure. In addition, unless otherwise specified, none of the steps of the methods of the present disclosure are confined to any particular order of performance. Modifications of the disclosed embodiments incorporating the spirit and substance of the disclosure may occur to persons skilled in the art and such modifications are within the scope of the present disclosure. Furthermore, all references cited herein are incorporated by reference in their entirety.

Terms of orientation used herein, such as "top," "bottom," "horizontal," "vertical," "longitudinal," "lateral," and "end" are used in the context of the illustrated embodiment. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that can be measured from side-to-side. Terms relating to shapes generally, such as "circular" or "cylindrical" or "semi-circular" or "semi-cylindrical" or any related or similar terms, are not required to conform strictly to the mathematical definitions of circles or cylinders or other structures, but can encompass structures that are reasonably close approximations.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

The terms "approximately," "about," and "substantially" as used herein represent an amount close to the stated amount that still performs a desired function or achieves a desired result. For example, in some embodiments, as the context may dictate, the terms "approximately", "about", and "substantially" may refer to an amount that is within less than or equal to 10% of the stated amount. The term "generally" as used herein represents a value, amount, or characteristic that predominantly includes or tends toward a particular value, amount, or characteristic. As an example, in certain embodiments, as the context may dictate, the term "generally parallel" can refer to something that departs from exactly parallel by less than or equal to 20 degrees.

Unless otherwise explicitly stated, articles such as "a" or "an" should generally be interpreted to include one or more described items. Accordingly, phrases such as "a device configured to" are intended to include one or more recited devices. Such one or more recited devices can be collectively configured to carry out the stated recitations. For example, "a processor configured to carry out recitations A, B, and C" can include a first processor configured to carry out recitation A working in conjunction with a second processor configured to carry out recitations B and C.

The terms "comprising," "including," "having," and the like are synonymous and are used inclusively, in an open-ended fashion, and do not exclude additional elements, features, acts, operations, and so forth. Likewise, the terms "some," "certain," and the like are synonymous and are used in an open-ended fashion. Also, the term "or" is used in its inclusive sense (and not in its exclusive sense) so that when used, for example, to connect a list of elements, the term "or" means one, some, or all of the elements in the list.

Overall, the language of the claims is to be interpreted broadly based on the language employed in the claims. The language of the claims is not to be limited to the non-exclusive embodiments and examples that are illustrated and described in this disclosure, or that are discussed during the prosecution of the application.

Although systems and methods for deploying intraluminal devices and post deployment dilation thereof have been disclosed in the context of certain embodiments and examples, this disclosure extends beyond the specifically disclosed embodiments to other alternative embodiments and/or uses of the embodiments and certain modifications and equivalents thereof. Various features and aspects of the disclosed embodiments can be combined with or substituted for one another in order to form varying modes of systems and methods for deploying intraluminal devices and post deployment dilation thereof. The scope of this disclosure should not be limited by the particular disclosed embodiments described herein.

Certain features that are described in this disclosure in the context of separate implementations can be implemented in combination in a single implementation. Conversely, various features that are described in the context of a single implementation can be implemented in multiple implementations separately or in any suitable subcombination. Although features may be described herein as acting in certain combinations, one or more features from a claimed combination can, in some cases, be excised from the combination, and the combination may be claimed as any subcombination or variation of any subcombination.

While the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various embodiments described and the appended claims. Further, the disclosure herein of any particular feature, aspect, method, property, characteristic, quality, attribute, element, or the like in connection with an embodiment can be used in all other embodiments set forth herein. Any methods disclosed herein need not be performed in the order recited. Depending on the embodiment, one or more acts, events, or functions of any of the algorithms, methods, or processes described herein can be performed in a different sequence, can be added, merged, or left out altogether (e.g., not all described acts or events are necessary for the practice of the algorithm). In some embodiments, acts or events can be performed concurrently, e.g., through multi-threaded processing, interrupt processing, or multiple processors or processor cores or on other parallel architectures, rather than sequentially. Further, no element, feature, block, or step, or group of elements, features, blocks, or steps, are necessary or indispensable to each embodiment. Additionally, all possible combinations, subcombinations, and rearrangements of systems, methods, features, elements, modules, blocks, and so forth are within the scope of this disclosure. The use of sequential, or time-ordered language, such as "then," "next," "after," "subsequently," and the like, unless specifically stated otherwise, or otherwise understood within the context as used, is generally intended to facilitate the flow of the text and is not intended to limit the sequence of operations performed. Thus, some embodiments may be performed using the sequence of operations described herein, while other embodiments may be performed following a different sequence of operations.

Moreover, while operations may be depicted in the drawings or described in the specification in a particular order, such operations need not be performed in the particular order shown or in sequential order, and all operations need not be performed, to achieve the desirable results. Other operations that are not depicted or described can be incorporated in the example methods and processes. For example, one or more additional operations can be performed before, after, simultaneously, or between any of the described operations. Further, the operations may be rearranged or reordered in other implementations. Also, the separation of various system components in the implementations described herein should not be understood as requiring such separation in all implementations, and it should be understood that the described components and systems can generally be integrated together in a single product or packaged into multiple products. Additionally, other implementations are within the scope of this disclosure.

Some embodiments have been described in connection with the accompanying figures. Certain figures are drawn and/or shown to scale, but such scale should not be limiting, since dimensions and proportions other than what are shown are contemplated and are within the scope of the embodiments disclosed herein. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, any methods described herein may be practiced using any device suitable for performing the recited steps.

The methods disclosed herein may include certain actions taken by a practitioner; however, the methods can also include any third-party instruction of those actions, either expressly or by implication. For example, actions such as "positioning an electrode" include "instructing positioning of an electrode."

In summary, various embodiments and examples of systems and methods for deploying intraluminal devices and post deployment dilation thereof have been disclosed. Although the systems and methods for deploying intraluminal devices and post deployment dilation thereof have been disclosed in the context of those embodiments and examples, this disclosure extends beyond the specifically disclosed embodiments to other alternative embodiments and/or other uses of the embodiments, as well as to certain modifications and equivalents thereof. This disclosure expressly contemplates that various features and aspects of the disclosed embodiments can be combined with, or substituted for, one another. Thus, the scope of this disclosure should not be limited by the particular disclosed embodiments described herein, but should be determined only by a fair reading of the claims that follow.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1 V" includes "1 V." Phrases preceded by a term such as "substantially" include the recited phrase and should be interpreted based on the circumstances (e.g., as much as reasonably possible under the circumstances). For example, "substantially perpendicular" includes "perpendicular." Unless stated otherwise, all measurements are at standard conditions including temperature and pressure.

What is claimed is:

1. A delivery device comprising:
an inner shaft configured to receive a self-expanding intraluminal device for deployment from the delivery device into a vessel;
an outer sheath outward of the inner shaft and movable with respect to the inner shaft, the outer sheath having a pre-deployment position in which the self-expanding intraluminal device is covered and a delivery position in which the self-expanding intraluminal device is uncovered to release the self-expanding intraluminal device from the delivery device;
a post-deployment dilation device comprising:
a balloon attached to the outer sheath of the delivery device, the balloon having a pre-actuated configuration having a pre-deployment diameter and an actuated configuration having a deployment diameter larger than the pre-deployment diameter;
a single helical filament wrapped around the balloon in a pre-deployment configuration; and
one or more inflation lumens contained in the outer sheath and in fluid communication with the balloon;
a distal radiopaque marker adjacent a distal end of the balloon, wherein the distal radiopaque marker is spaced from a distal end of the outer sheath; and
a proximal radiopaque marker adjacent a proximal end of the balloon;
wherein the post deployment dilation device is configured to apply a radial force to an inner surface of the self-expanding intraluminal device after deployment of the self expanding intraluminal device to improve at least one of expansion of the self-expanding intraluminal device or seating of the self-expanding intraluminal device in the vessel, and
wherein the inner shaft includes a helical filament lumen, the single helical filament configured to be retracted into the helical filament lumen to release the balloon of the post-deployment dilation device.

2. The delivery device of claim 1, further comprising a pressure sensor configured to detect a pressure within the balloon and configured to communicate with an inflation device in fluid communication with the balloon and provide instructions to the inflation device such that the inflation device does not inflate the balloon past a set threshold.

3. The delivery device of claim 1, wherein a length of the balloon is the same as a length of the self-expanding intraluminal device.

4. The delivery device of claim 1, wherein the outer sheath comprises a guidewire lumen comprising an exit aperture distal to a proximal end of the outer sheath.

5. The delivery device of claim 1, wherein the one or more inflation lumens comprise two inflation lumens, the delivery device further comprising a pressure sensor configured to detect a pressure within the balloon and configured to communicate with an inflation device in fluid communication with the balloon and provide instructions to the inflation device such that the inflation device does not inflate the balloon past a set threshold, wherein a length of the balloon is the same as a length of the self-expanding intraluminal device, wherein the outer sheath comprises a guidewire lumen comprising an exit aperture distal to a proximal end of the outer sheath, and wherein each of the two inflation lumens is oblong.

6. The delivery device of claim 1, wherein the single helical filament is configured to release the balloon in a deployment configuration in which the balloon is inflated.

7. The delivery device of claim 1, wherein the outer sheath includes an outer sheath inner tube and an outer sheath outer tube and the balloon is attached to both the outer sheath inner tube and the outer sheath outer tube.

8. The delivery device of claim 1, wherein the single helical filament is further configured to be extended out of the helical filament lumen to cause the single helical filament to wrap helically around the balloon to trap the balloon.

9. A delivery device comprising:
an inner shaft configured to receive a self-expanding intraluminal device for deployment from the delivery device into a vessel;
an outer sheath outward of the inner shaft and movable with respect to the inner shaft, the outer sheath having a pre-deployment position in which the self-expanding intraluminal device is covered and a delivery position in which the self-expanding intraluminal device is uncovered to release the self-expanding intraluminal device from the delivery device;
a post-deployment dilation device comprising:
a balloon attached to the outer sheath of the delivery device, the balloon having a pre-actuated configuration having a pre-deployment diameter and an actuated configuration having a deployment diameter larger than the pre-deployment diameter;
a helical filament wrapped around the balloon in a pre-deployment configuration and retractable into a helical filament lumen of the inner shaft to release the balloon in a deployment configuration in which the balloon is inflated; and
one or more inflation lumens contained in the outer sheath and in fluid communication with the balloon;
a distal radiopaque marker adjacent a distal end of the balloon, wherein the distal radiopaque marker is spaced from a distal end of the outer sheath; and
a proximal radiopaque marker adjacent a proximal end of the balloon;
wherein the post deployment dilation device is configured to apply a radial force to an inner surface of the self-expanding intraluminal device after deployment of the self-expanding intraluminal device to improve at least one of expansion of the self-expanding intraluminal device or seating of the self-expanding intraluminal device in the vessel.

10. The delivery device of claim 9, wherein the helical filament is further configured to be extended out of the helical filament lumen to cause the helical filament to wrap helically around the balloon to trap the balloon.

11. A delivery device comprising:
an inner shaft configured to receive a self-expanding intraluminal device for deployment from the delivery device into a vessel;
an outer sheath outward of the inner shaft and movable with respect to the inner shaft, the outer sheath having a pre-deployment position in which the self-expanding intraluminal device is covered and a delivery position in which the self-expanding intraluminal device is uncovered to release the self-expanding intraluminal device from the delivery device; and
a post-deployment dilation device comprising:
a balloon attached to the outer sheath of the delivery device, the balloon having a pre-actuated configuration having a pre-deployment diameter and an actuated configuration having a deployment diameter larger than the pre-deployment diameter;
a helical filament wrapped around the balloon in a pre-deployment configuration and retractable into a helical filament lumen of the inner shaft to release the balloon in a deployment configuration in which the balloon is inflated; and
one or more inflation lumens contained in the outer sheath and in fluid communication with the balloon.

12. The delivery device of claim 11, wherein the helical filament is further configured to be extended out of the helical filament lumen to cause the helical filament to wrap helically around the balloon to trap the balloon.

13. The delivery device of claim 11 wherein the post deployment dilation device is configured to apply a radial force to an inner surface of the self-expanding intraluminal device after deployment of the self-expanding intraluminal device to improve at least one of expansion of the self-expanding intraluminal device or seating of the self-expanding intraluminal device in the vessel.

14. The delivery device of claim 11 further comprising:
a distal radiopaque marker adjacent a distal end of the balloon, wherein the distal radiopaque marker is spaced from a distal end of the outer sheath; and
a proximal radiopaque marker adjacent a proximal end of the balloon.

* * * * *